United States Patent
Wang et al.

(10) Patent No.: US 12,129,266 B2
(45) Date of Patent: Oct. 29, 2024

(54) SUBSTITUTED PYRAZOLO[1,5-A]PYRIDINE COMPOUND, COMPOSITION CONTAINING THE SAME AND USE THEREOF

(71) Applicant: Shenzhen TargetRx, Inc., Guangdong (CN)

(72) Inventors: Yihan Wang, Guangdong (CN); Xingye Ren, Guangdong (CN)

(73) Assignee: Shenzhen TargetRx, Inc., Shenzhen (CN)

(*) Notice: Subject to any disclaimer, the term of this patent is extended or adjusted under 35 U.S.C. 154(b) by 714 days.

(21) Appl. No.: 17/299,999

(22) PCT Filed: Dec. 3, 2019

(86) PCT No.: PCT/CN2019/122674
§ 371 (c)(1),
(2) Date: Jun. 4, 2021

(87) PCT Pub. No.: WO2020/114388
PCT Pub. Date: Jun. 11, 2020

(65) Prior Publication Data
US 2022/0017539 A1    Jan. 20, 2022

(30) Foreign Application Priority Data

Dec. 6, 2018  (CN) .......................... 201811488548.X
Dec. 13, 2018 (CN) .......................... 201811527134.3

(51) Int. Cl.
C07D 519/00    (2006.01)
C07D 471/04    (2006.01)

(52) U.S. Cl.
CPC ......... *C07D 519/00* (2013.01); *C07D 471/04* (2013.01)

(58) Field of Classification Search
None
See application file for complete search history.

(56) References Cited

FOREIGN PATENT DOCUMENTS

| | | | |
|---|---|---|---|
| CN | 108349969 A | 7/2018 | |
| JP | 2018-532690 A | 11/2018 | |
| JP | 2020-503247 A | 1/2020 | |
| WO | WO-2017011776 A1 * | 1/2017 | ............ A61K 31/437 |
| WO | WO-2018071447 A1 * | 4/2018 | ............ A61K 31/444 |

OTHER PUBLICATIONS

Office Action for Chinese Application No. 201911221106.3 Jun. 29, 2022.
Office Action for Japanese Application No. 2021-532190, mailed Jul. 26, 2022.
Harbeson et al., Chapter 24—Deuterium in Drug Discovery and Development. Annual Reports in Medicinal Chemistry. 2011; 46: 403-417.
Jiang et al., Application of deuteration in drug research. Qilu Pharmaceutical Affairs. 2010;29(11):682-4.
Kushner et al., Pharmacological uses and perspectives of heavy water and deuterated compounds. Can J Physiol Pharmacol. Feb. 1999;77(2):79-88.
Extended European Search Report for Application No. EP19892345.0, mailed Nov. 17, 2021.
Foster, Deuterium isotope effects in the metabolism of drugs and xenobiotics: implications for drug design, Chapter 1 to Chapter 2.1. Advances in Drug Research. Jan. 1, 1985;14: 1-40. ISSN:0065-2490.
International Search Report and Written Opinion for Application No. PCT/CN2019/122674, mailed Mar. 6, 2020.
International Preliminary Report on Patentability for Application No. PCT/CN2019/122674, mailed Jun. 17, 2021.
Berge et al., Pharmaceutical Salts. J Pharm Sci. Jan. 1977;66(1):1-19. doi: 10.1002/jps.2600660104.
Mulligan, Ret revisited: expanding the oncogenic portfolio. Nat Rev Cancer. Mar. 2014;14(3):173-86. doi: 10.1038/nrc3680.

* cited by examiner

*Primary Examiner* — Jeffrey S Lundgren
*Assistant Examiner* — Anthony Joseph Seitz
(74) *Attorney, Agent, or Firm* — Wolf, Greenfield & Sacks, P.C.

(57) ABSTRACT

The present disclosure provides a substituted pyrazolo[1,5-a]pyridine compound, a composition including the same, and a use thereof. The substituted pyrazolo[1,5-a]pyridine compounds is a compound represented by formula (I) or the tautomers, stereoisomers, prodrugs, crystal forms, pharmaceutically acceptable salts, hydrates or solvates thereof. The compound of the present disclosure and composition thereof are useful for treating RET kinase-mediated diseases or conditions and have more excellent pharmacokinetic properties.

(I)

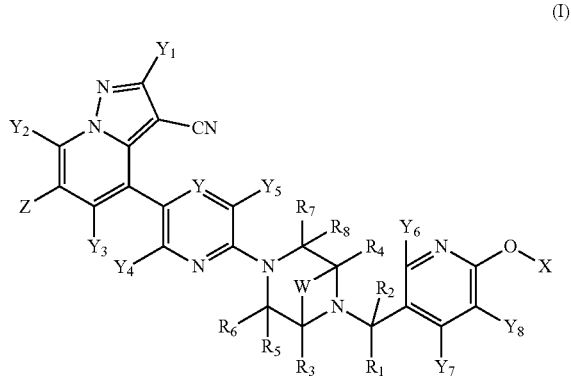

20 Claims, No Drawings

SUBSTITUTED PYRAZOLO[1,5-A]PYRIDINE COMPOUND, COMPOSITION CONTAINING THE SAME AND USE THEREOF

CROSS REFERENCE TO RELATED APPLICATIONS

The present application is a national stage filing under 35 U.S.C. § 371 of International PCT Application PCT/CN2019/122674, filed Dec. 3, 2019, which claims priority to Chinese Patent Application No. 201811488548.X, filed Dec. 6, 2018, and to Chinese Patent Application No. 201811527134.3, filed Dec. 13, 2018, the entire contents of each of which are incorporated herein by reference.

TECHNICAL FIELD

The present disclosure belongs to the pharmaceutical technical field, and particularly relates to a substituted pyrazolo[1,5-a]pyridine compound, composition containing the same and use thereof. More specifically, the present disclosure relates to some deuterium substituted pyrazolo[1,5-a]pyridine compound, these deuterium-substituted compounds and compositions thereof can be used to treat RET kinase mediated diseases or disorders, and these deuterium-substituted compounds have better pharmacokinetic properties.

BACKGROUND OF THE INVENTION

RET (Rearranged during transfection) belongs to the receptor tyrosine kinase protein family, is a cell surface molecule that transduces signals for cell growth and differentiation. The extracellular part of RET kinase contains four calcium-dependent cadherin-like repeats involved in ligand binding and proximal membrane cysteine-rich region necessary for correct folding of RET extracellular domain, and the cytoplasmic part of the receptor includes two tyrosine kinase subdomains.

The main ligand of the RET protein belongs to the glial cell line derived neurotrophic factor (GDNF) family, including GDNF, Neurturin (NTRN, nerve growth factor), artemin (ARTN, artemin factor) and persephin (PSPN, persephin factor). After the RET receptor binds to its ligand, the intracellular tyrosine kinase is phosphorylated, which in turn induces RET dimerization, autophosphorylation, and substrate phosphorylation, thereby activating multiple downstream signaling pathways in the cell, including Ras-MAPK and PI3K-Akt/mTOR pathway, or leads to the recruitment of the CBL family of ubiquitin ligases that play a role in the RET downregulation of RET-mediated functions.

RET gene mutation or RET gene fusion has been identified as a driving factor for certain cancers. The incidence of RET gene fusion in non-small cell lung cancer is about 2%, and the incidence in Papillary Thyroid Cancers (PTCs) is 10% to 20%. The most common fusion partners include KIF5B, TRIM33, CCDC6 and NCOA4. The incidence of RET gene mutation in Medullary Thyroid Cancers (MTCs) is about 60%, and the most common mutation site is M918T. RET inhibitor resistance mutations include but are not limited to amino acid position 804 (V804M, V804L, V804E), amino acid position 805 (E805K), and amino acid position 806 (Y806C, Y806E).

International publication No. WO 2017/011776 A1 and WO 2018/071447 A1 disclosed a series of substituted pyrazolo[1,5-a]pyridine compounds as RET kinase inhibitors, which can be used to treat and prevent RET kinase-mediated diseases or disorder.

Poor absorption, distribution, metabolism, and/or excretion (ADME) properties are known to be the primary causes of clinical trial failure of many drug candidates. At present, many marketed drugs have limitations on their application due to their poor ADME properties. The rapid metabolism makes many drugs, which could have been effective in treating diseases otherwise, difficult to be used as drugs due to their rapid clearance from the body. Although a frequent or high-dose administration may solve the problem of rapid drug clearance, this approach will bring about problems such as poor compliance of patients, side effects caused by high-dose administration, and increased treatment costs. In addition, drugs that are rapidly metabolized may also expose the patients to undesirable toxic or reactive metabolites.

So far, no RET inhibitor has been approved for marketing, so there are still serious unmet clinical needs in this field. It is still challenging to discover new compounds that can treat RET-associated diseases and have good oral bioavailability and druggability. Therefore, there is still a need in the art to develop compounds that have selective inhibitory activity and/or better pharmacodynamics/pharmacokinetics for use as RET inhibitors, and the present disclosure provides such compounds.

SUMMARY OF THE INVENTION

In view of the above technical problems, the present disclosure discloses a novel deuterium-substituted pyrazolo[1,5-a]pyridine compound and a composition containing the compound and use thereof, which has the activity of inhibiting a RET, a RET gene mutation and a RET gene fusion in cells or patients, and has lower side effects and better pharmacokinetic properties at the same time, and can be used to treat related diseases or disorders mediated by the RET kinase.

As used herein, the term "compounds of the present disclosure" refers to compounds represented by formulae (I) and (II) (including subsets of each formula, such as formula (II-A), formula (II-B-a)). The term also includes tautomers, stereoisomers, prodrugs, crystal forms, pharmaceutically acceptable salts, hydrates or solvates thereof.

In this regard, the present disclosure adopts the following technical solutions:

In the first aspect, the present disclosure provides a compound of formula (I):

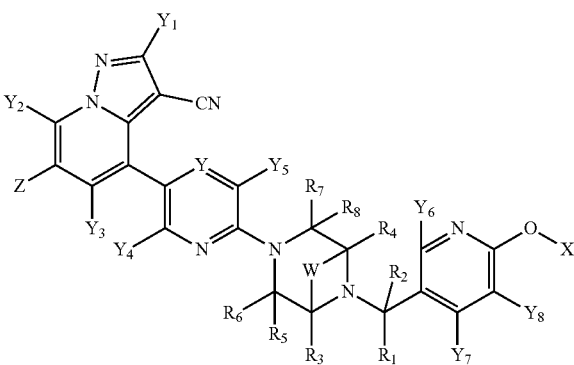

formula (I)

wherein,
Y is selected from CH or N, which is optionally substituted by deuterium, halogen or trifluoromethyl;
W is $CR_9R_{10}$;
$R_1$, $R_2$, $R_3$, $R_4$, $R_5$, $R_6$, $R_7$, $R_8$, $R_9$ and $R_{10}$ are each independently selected from hydrogen or deuterium;
$Y_1$, $Y_2$, $Y_3$, $Y_4$, $Y_5$, $Y_6$, $Y_7$ and $Y_8$ are each independently selected from hydrogen, deuterium, halogen or trifluoromethyl;
X is selected from $CH_3$, $CD_3$, $CHD_2$ or $CH_2D$;
Z is selected from:

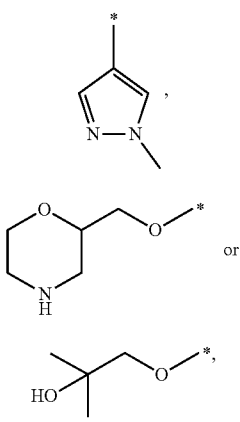

which is optionally substituted by 1, 2, 3, 4, 5, 6, 7, 8 or 9 deuterium;
*represents the bond connected to the core;
provided that the above compound has at least one deuterium atom;
or the tautomers, stereoisomers, prodrugs, crystal forms, pharmaceutically acceptable salts, hydrates or solvates thereof.

In another aspect, the present disclosure provides a pharmaceutical composition containing a compound of the present disclosure and pharmaceutically acceptable excipient(s). In a specific embodiment, the compound of the present disclosure is provided in the pharmaceutical composition in an effective amount. In a specific embodiment, the compound of the present disclosure is provided in a therapeutically effective amount. In a specific embodiment, the compound of the present disclosure is provided in a prophylactically effective amount. In a specific embodiment, the pharmaceutical composition further contains additional therapeutic agent(s). In a specific embodiment, the additional therapeutic agent is selected from cytotoxic chemotherapeutics, kinase targeted therapeutic agents, apoptosis regulators or signal transduction inhibitors. In a specific embodiment, the additional therapeutic agent is selected from one or more kinase targeted therapeutic agents.

In another aspect, the present disclosure provides a method for preparing the pharmaceutical composition as described above, including the following steps: pharmaceutically acceptable excipient(s) is(are) mixed with the compound of the present disclosure to form a pharmaceutical composition.

In another aspect, the present disclosure also refers to the use of the compounds of the present disclosure or the tautomers, stereoisomers, prodrugs, crystal forms, pharmaceutically acceptable salts, hydrates or solvates thereof, or the above-mentioned pharmaceutical composition in the preparation of a medicament for the treatment of RET-associated cancers. In a specific embodiment, RET-associated cancers are cancers in which a RET gene, a RET kinase, or the expression or activity or level of any of the same is dysregulated. In a specific embodiment, dysregulation of a RET gene, a RET kinase protein, or the expression or activity or level of any of the same is one or more point mutations in the RET gene. In a specific embodiment, one or more point mutations in the RET gene result in the translation of RET proteins with one or more of the following amino acid substitutions: S32L, D34S, L40P, P64L, R67H, R114H, V145G, V292M, G321R, R330Q, T338I, R360W, F393L, A510V, E511K, C515S, C531R, G533C, G533S, G550E, V591I, G593E, I602V, R600Q, K603Q, K603E, Y606C, C609Y, C609S, C609G, C609R, C609F, C609W, C611R, C611S, C611G, C611Y, C611F, C611W, C618S, C618Y, C618R, C618Y, C618G, C618F, C618W, F619F, C620S, C620W, C620R, C620G, C620L, C620Y, C620F, E623K, D624N, C630A, C630R, C630S, C630Y, C630F, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, S686N, G691S, R694Q, M700L, V706M, V706A, E713K, G736R, G748C, A750P, S765P, P766S, P766M, E768Q, E768D, L769L, R770Q, D771N, N777S, V778I, Q781R, L790F, Y791F, V804L, V804M, V804E, E805K, Y806E, Y806F, Y806S, Y806G, Y806C, E818K, S819I, G823E, Y826M, R833C, P841L, P841P, E843D, R844W, R844Q, R844L, M848T, I852M, A866W, R873W, A876V, L881V, A883F, A883S, A883T, E884K, R886W, S891A, R897Q, D898V, E901K, S904F, S904C, K907E, K907M, R908K, G911D, R912P, R912Q, M918T, M918V, M918L, A919V, E921K, S922P, S922Y, T930M, F961L, R972G, R982C, M1009V, D1017N, V1041G or M1064T. In a specific embodiment, dysregulation of a RET gene, a RET kinase, or the expression or activity or level of any of the same is RET gene fusion. In a specific embodiment, the RET gene fusion is selected from: BCR-RET, CLIP1-RET, KIF5B-RET, CCDC6-RET, NCOA4-RET, TRIM33-RET, ERC1-RET, ELKS-RET, RET-ELKS, FGFR1OP-RET, RET-MBD1, RET-RAB61P2, RET-PCM1, RET-PPKAR1A, RET-TRIM24, RET-RFG9, RFP-RET, RET-GOLGA5, HOOKS-RET, KTN1-RET, TRIM27-RET, AKAP13-RET, FKBP15-RET, SPECC1L-RET, TBL1XR1/RET, CEP55-RET, CUX1-RET, KIAA1468-RET, PPKAR1A-RET, RFG8/RET, RET/RFG8, H4-RET, ACBD5-RET, PTCex9-RET, MYH13-RET, PIBF1-RET, KIAA1217-RET or MPRIP-RET. In a specific embodiment, the RET-associated cancer is selected from lung cancer, papillary thyroid cancer, medullary thyroid cancer, differentiated thyroid cancer, recurrent thyroid cancer, refractory differentiated thyroid cancer, multiple endocrine tumors of type 2A or 2B (MEN2A or MEN2B, respectively), pheochromocytoma, parathyroid hyperplasia, breast cancer, colorectal cancer, papillary renal cell carcinoma, gastrointestinal mucosal gangliocytoma and cervical cancer. In a specific embodiment, the compound is administered orally, subcutaneously, intravenously or intramuscularly. In a specific embodiment, the compound is administrated for a long period of time.

From the following specific embodiments, examples and claims, other objects and advantages of the present disclosure will be obvious to those skilled in the art.

DETAILED DESCRIPTION OF THE INVENTION

Definition

Herein, unless otherwise specified, "deuterated" refers to that one or more hydrogens in a compound or group are replaced by deuterium; deuteration can be mono-substitution, di-substitution, multi-substitution or per-substitution. The terms "one or more deuterated" and "deuterated one or more times" are used interchangeably.

Herein, unless otherwise specified, "non-deuterated compound" refers to a compound wherein the content of the deuterium atom is not higher than the natural content of the deuterium isotope (0.015%).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66: 1-19. Pharmaceutically acceptable salts of the compounds of the present disclosure include those derived from suitable inorganic and organic acids and inorganic and organic bases.

The compounds of the present disclosure may be in amorphous or crystalline form. In addition, the compounds of the present disclosure may exist in one or more crystalline forms. Therefore, the present disclosure includes all amorphous or crystalline forms of the compounds of the present disclosure within its scope. The term "crystal form" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

As used herein, the term "subject" includes, but is not limited to, humans (i.e., a male or female of any age group, e.g., a pediatric subject (e.g., infant, child, adolescent) or adult subject (e.g., young adult, middle-aged adult or elderly adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

"Disease", "disorder" and "condition" are used interchangeably herein.

As used herein, unless otherwise specified, the terms "treat", "treating", and "treatment" contemplate an action that occurs while a subject is suffering from a particular disease, disorder, or condition, which reduces the severity of the disease, disorder or condition, or retards or slows the progression of the disease, disorder or condition ("therapeutic treatment"). The terms also contemplate an action that occurs before a subject begins to suffer from a specific disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically and prophylactically effective amount.

As used herein, unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a compound of the present disclosure. For example, a compound disclosed herein may be administered simultaneously or sequentially with another therapeutic agent in separate unit dosage forms, or together with another therapeutic agent in a single unit dosage form.

Compound

In one embodiment, the present disclosure relates to a compound of formula (I), or the tautomers, stereoisomers, prodrugs, crystal forms, pharmaceutically acceptable salts, hydrates or solvates thereof:

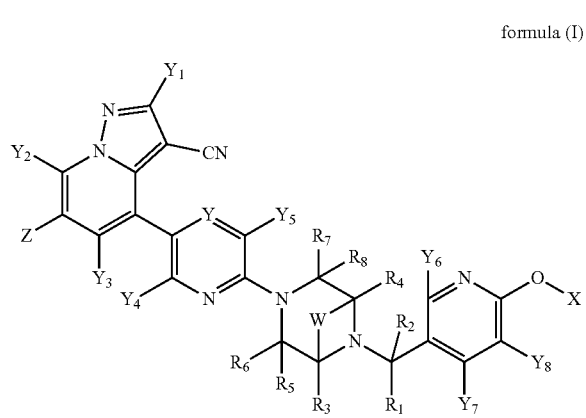

formula (I)

wherein,
Y is selected from CH or N, which is optionally substituted by deuterium, halogen or trifluoromethyl;
W is $CR_9R_{10}$;
$R_1$, $R_2$, $R_3$, $R_4$, $R_5$, $R_6$, $R_7$, $R_8$, $R_9$ and $R_{10}$ are each independently selected from hydrogen or deuterium;
$Y_1$, $Y_2$, $Y_3$, $Y_4$, $Y_5$, $Y_6$, $Y_7$ and $Y_8$ are each independently selected from hydrogen, deuterium, halogen or trifluoromethyl;
X is selected from $CH_3$, $CD_3$, $CHD_2$ or $CH_2D$;

Z is selected from:

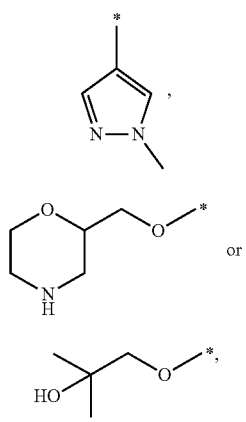

which is optionally substituted by 1, 2, 3, 4, 5, 6, 7, 8 or 9 deuterium;
*represents the bond connected to the core;
provided that the above compound has at least one deuterium atom.

As a preferred embodiment of the present disclosure, the isotope content of deuterium at the deuterated position is at least greater than the 0.015% natural isotope content of deuterium, alternatively greater than 30%, alternatively greater than 50%, alternatively greater than 75%, alternatively greater than 95%, alternatively greater than 99%.

As a preferred embodiment of the present disclosure, the present disclosure contains at least one deuterium atom, alternatively contains two deuterium atoms, alternatively contains three deuterium atoms, alternatively contains four deuterium atoms, alternatively contains five deuterium atoms, alternatively contains six deuterium atoms, alternatively contains seven deuterium atoms, alternatively contains eight deuterium atoms, alternatively contains nine deuterium atoms, alternatively contains ten deuterium atoms, alternatively contains eleven deuterium atoms, alternatively contains twelve deuterium atoms, alternatively contains thirteen deuterium atoms, alternatively contains fourteen deuterium atoms, alternatively contains fifteen deuterium atoms, alternatively contains sixteen deuterium atoms, alternatively contains seventeen deuterium atoms, alternatively contains eighteen deuterium atoms, alternatively contains nineteen deuterium atoms, alternatively contains twenty deuterium atoms, In some embodiments, Y is selected from CH or N, which is optionally substituted by deuterium, halogen or trifluoromethyl; in some other embodiments, Y is selected from CH, N, CD, CF or CCF3; in some other embodiments, Y is selected from CH; in some other embodiments, Y is selected from N.

In some embodiments, $Y_1$, $Y_2$, $Y_3$, $Y_4$, $Y_5$, $Y_6$, $Y_7$ and $Y_8$ are each independently selected from hydrogen, deuterium, halogen or trifluoromethyl; in some other embodiments, $Y_1$, $Y_2$, $Y_3$, $Y_4$, $Y_5$, $Y_6$, $Y_7$ and $Y_8$ are each independently selected from hydrogen, deuterium, F or trifluoromethyl; in some other embodiments, $Y_1$, $Y_2$, $Y_3$, $Y_4$, $Y_5$, $Y_6$, $Y_7$ and $Y_8$ are each independently hydrogen; in some other embodiments, $Y_1$, $Y_2$, $Y_3$, $Y_4$, $Y_5$, $Y_6$, $Y_7$ and $Y_8$ are each independently deuterium.

In some embodiments, $R_1$, $R_2$, $R_3$, $R_4$, $R_5$, $R_6$, $R_7$, $R_8$, $R_9$ and $R_{10}$ are each independently selected from hydrogen or deuterium; in some other embodiments, $R_1$ is hydrogen; in some other embodiments, $R_1$ is deuterium; in some other embodiments, $R_2$ is hydrogen; in some other embodiments, $R_2$ is deuterium; in some other embodiments, $R_3$ is hydrogen; in some other embodiments, $R_3$ is deuterium; in some other embodiments, $R_4$ is hydrogen; in some other embodiments, $R_4$ is deuterium; in some other embodiments, $R_5$ is hydrogen; in some other embodiments, $R_5$ is deuterium; in some other embodiments, $R_6$ is hydrogen; in some other embodiments, $R_6$ is deuterium; in some other embodiments, $R_7$ is hydrogen; in some other embodiments, $R_7$ is deuterium; in some other embodiments, $R_8$ is hydrogen; in some other embodiments, $R_8$ is deuterium; in some other embodiments, $R_9$ is hydrogen; in some other embodiments, $R_9$ is deuterium; in some other embodiments, $R_{10}$ is hydrogen; in some other embodiments, $R_{10}$ is deuterium.

In some embodiments, X is selected from $CH_3$, $CD_3$, $CHD_2$ or $CH_2D$; in some other embodiments, X is $CH_3$; in some other embodiments, X is $CD_3$; in some other embodiments, X is $CHD_2$; in some other embodiments, X is $CH_2D$.

In some embodiments, Z is

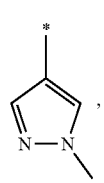

which is optionally substituted by 1, 2, 3, 4 or 5 deuterium; in some embodiments, Z is selected from

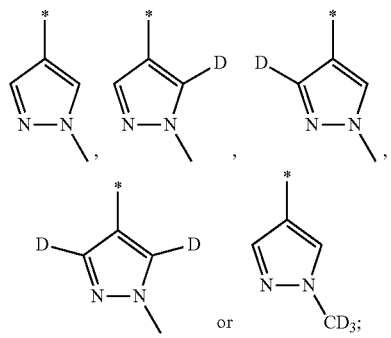

in some other embodiments, Z is

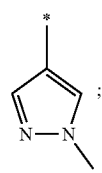

in some other embodiments, Z is

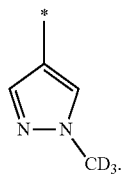

In some embodiments, Z is

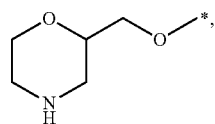

which is optionally substituted by 1, 2, 3, 4, 5, 6, 7, 8 or 9 deuterium; in some other embodiments, Z is selected from

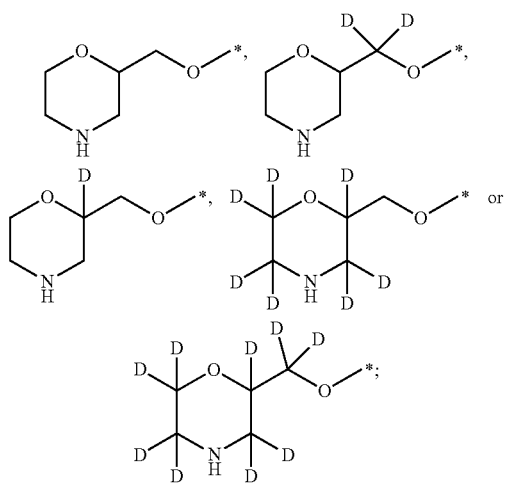

in some other embodiments, Z is selected from

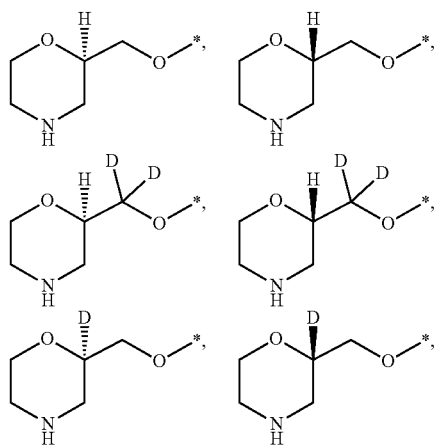

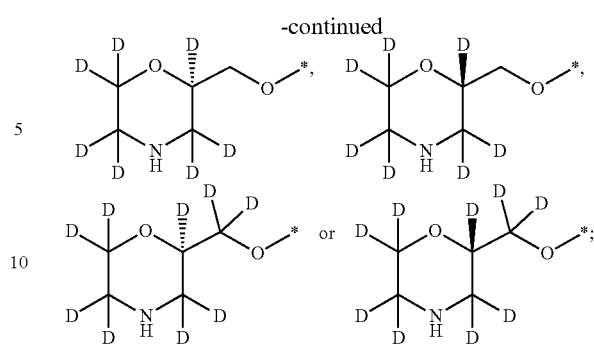

in some other embodiments, Z is selected from

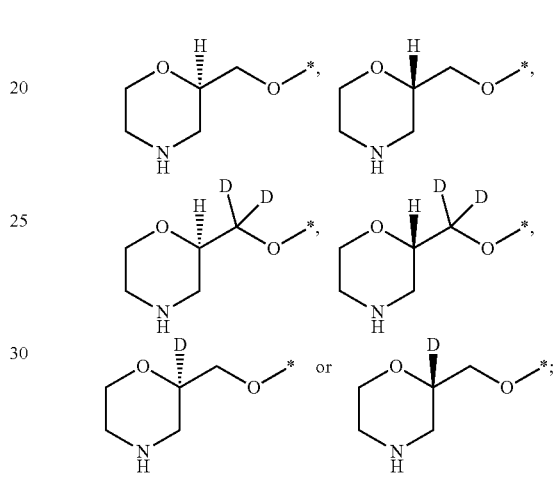

in some other embodiments, Z is selected from

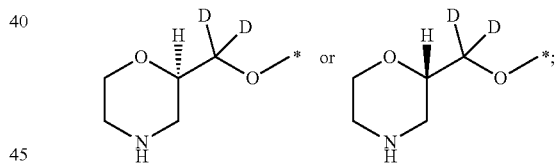

in some other embodiments, Z is selected from

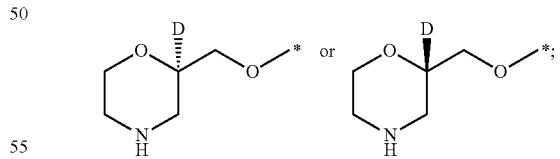

in some other embodiments, Z is selected from

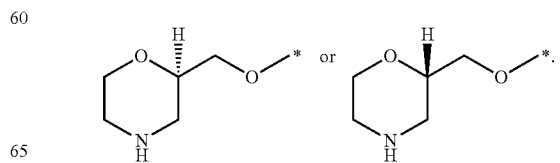

In some embodiments, Z is

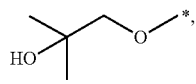
(c)

which is optionally substituted by 1, 2, 3, 4, 5, 6, 7 or 8 deuterium; in some other embodiments, Z is selected from

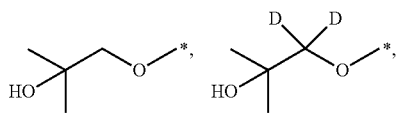

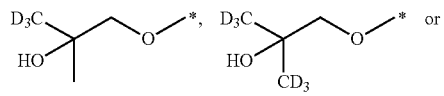 or

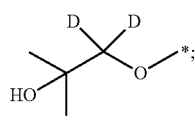;

in some other embodiments, Z is,

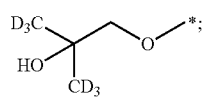;

in some other embodiments, Z is

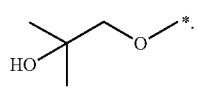;

in some other embodiments, Z is

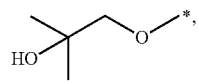.

In another embodiment, the present disclosure relates to a compound of formula (II), or the tautomers, stereoisomers, prodrugs, crystal forms, pharmaceutically acceptable salts, hydrates or solvates thereof:

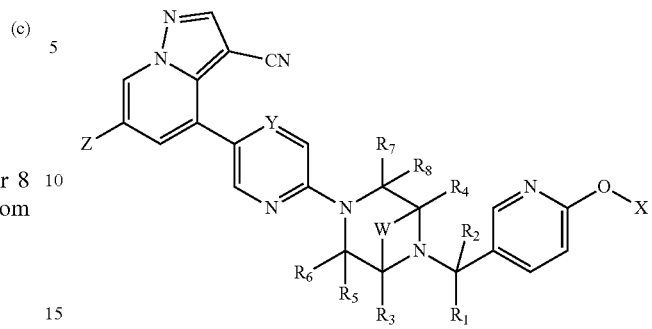
formula (II)

wherein,

Y is selected from CH or N;

W is $CR_9R_{10}$;

$R_1$, $R_2$, $R_3$, $R_4$, $R_5$, $R_6$, $R_7$, $R_8$, $R_9$ and $R_{10}$ are each independently selected from hydrogen or deuterium;

X is selected from $CH_3$, $CD_3$, $CHD_2$ or $CH_2D$;

Z is selected from:

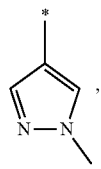
(a)

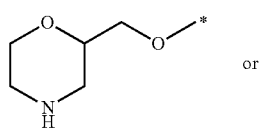 or
(b)

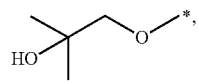,
(c)

which is optionally substituted by 1, 2, 3, 4, 5, 6, 7, 8 or 9 deuterium;

*represents the bond connected to the core;

provided that the above compound has at least one deuterium atom.

In another embodiment, the present disclosure relates to a compound of formula (I-A), or the tautomers, stereoisomers, prodrugs, crystal forms, pharmaceutically acceptable salts, hydrates or solvates thereof:

formula (I-A)

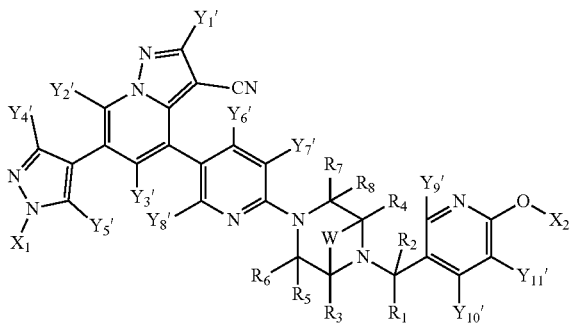

wherein,

W is $CR_9R_{10}$;

$R_1$, $R_2$, $R_3$, $R_4$, $R_5$, $R_6$, $R_7$, $R_8$, $R_9$ and $R_{10}$ are each independently selected from hydrogen or deuterium;

$Y_1'$, $Y_2'$, $Y_3'$, $Y_4'$, $Y_5'$, $Y_6'$, $Y_7'$, $Y_8'$, $Y_9'$, $Y_{10}'$ and $Y_{11}'$ are each independently selected from hydrogen, deuterium, halogen or trifluoromethyl;

$X_1$ and $X_2$ are each independently selected from $CH_3$, $CD_3$, $CHD_2$ or $CH_2D$;

provided that the above compound has at least one deuterium atom.

As a preferred embodiment of the present disclosure, the isotope content of deuterium at the deuterated position is at least greater than the 0.015% natural isotope content of deuterium, alternatively greater than 30%, alternatively greater than 50%, alternatively greater than 75%, alternatively greater than 95%, alternatively greater than 99%.

In a specific embodiment, "$R_1$, $R_2$, $R_3$, $R_4$, $R_5$, $R_6$, $R_7$, $R_8$, $R_9$ and $R_{10}$ are each independently selected from hydrogen or deuterium" includes the technical solutions wherein, $R_1$ is selected from hydrogen or deuterium, $R_2$ is selected from hydrogen or deuterium, $R_3$ is selected from hydrogen or deuterium, and so on, until $R_{10}$ is selected from hydrogen or deuterium. More specifically, the technical solutions wherein, $R_1$ is hydrogen or $R_1$ is deuterium, $R_2$ is hydrogen or $R_2$ is deuterium, $R_3$ is hydrogen or $R_3$ is deuterium, and so on, until $R_{10}$ is hydrogen or $R_{10}$ is deuterium, are included.

In another specific embodiment, "$Y_1'$, $Y_2'$, $Y_3'$, $Y_4'$, $Y_5'$, $Y_6'$, $Y_7'$, $Y_8'$, $Y_9'$, $Y_{10}'$ and $Y_{11}'$ are each independently selected from hydrogen, deuterium, halogen or trifluoromethyl" includes the technical solutions wherein, $Y_1'$ is selected from hydrogen, deuterium, halogen or trifluoromethyl, $Y_2'$ is selected from hydrogen, deuterium, halogen or trifluoromethyl, $Y_3'$ is selected from hydrogen, deuterium, halogen or trifluoromethyl, and so on, until $Y_{11}'$ is selected from hydrogen, deuterium, halogen or trifluoromethyl. More specifically, the technical solutions wherein, $Y_1'$ is hydrogen, $Y_1'$ is deuterium, $Y_1'$ is halogen (F, Cl, Br or I), or $Y_1'$ is trifluoromethyl, $Y_2'$ is hydrogen, $Y_2'$ is deuterium, $Y_2'$ is halogen (F, Cl, Br or I), or $Y_2'$ is trifluoromethyl, $Y_3$ is hydrogen, $Y_3$ is deuterium, $Y_3$ is halogen (F, Cl, Br or I), or $Y_3$ is trifluoromethyl, and so on, until $Y_{11}'$ is hydrogen, $Y_{11}'$ is deuterium, $Y_{11}'$ is halogen (F, Cl, Br or I), or $Y_{11}'$ is trifluoromethyl, are included.

In another specific embodiment, "$X_1$ and $X_2$ are each independently selected from $CH_3$, $CD_3$, $CHD_2$ or $CH_2D$" includes the technical solutions wherein, $X_1$ is selected from $CH_3$, $CD_3$, $CHD_2$ or $CH_2D$, $X_2$ is selected from $CH_3$, $CD_3$, $CHD_2$ or $CH_2D$. More specifically, the technical solutions wherein, $X_1$ is $CH_3$, $X_1$ is $CD_3$, $X_1$ is $CHD_2$ or $X_1$ is $CH_2D$, $X_2$ is $CH_3$, $X_2$ is $CD_3$, $X_2$ is $CHD_2$ or $X_2$ is $CH_2D$, are included.

In some embodiments, alternatively, $Y_1'$, $Y_2'$, $Y_3'$, $Y_4'$, $Y_5'$, $Y_6'$, $Y_7'$, $Y_8'$, $Y_9'$, $Y_{10}'$ and $Y_{11}'$ are each independently selected from hydrogen or deuterium.

In some embodiments, alternatively, $X_1$ and $X_2$ are each independently selected from $CH_3$ or $CD_3$.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_1$-$R_{10}$ are each independently selected from hydrogen or deuterium, $X_1$ and $X_2$ are each independently selected from $CH_3$, $CD_3$, $CHD_2$ or $CH_2D$, provided that the above compound has at least one deuterium atom.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_8$ are deuterium, $R_1$, $R_2$, $R_9$ and $R_{10}$ are each independently selected from hydrogen or deuterium, $X_1$ and $X_2$ are each independently selected from $CH_3$, $CD_3$, $CHD_2$ or $CH_2D$.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_9$ and $R_{10}$ are deuterium, $R_1$-$R_8$ are each independently selected from hydrogen or deuterium, $X_1$ and $X_2$ are each independently selected from $CH_3$, $CD_3$, $CHD_2$ or $CH_2D$.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_{10}$ are hydrogen, $R_1$ and $R_2$ are each independently selected from hydrogen or deuterium, $X_1$ and $X_2$ are each independently selected from $CH_3$, $CD_3$, $CHD_2$ or $CH_2D$, provided that the above compound has at least one deuterium atom.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_{10}$ are hydrogen, $R_1$ and $R_2$ are each independently selected from hydrogen or deuterium, $X_1$ and $X_2$ are each independently selected from $CH_3$ or $CD_3$, provided that the above compound has at least one deuterium atom.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_{10}$ are hydrogen, $X_1$ is $CD_3$, $R_1$ and $R_2$ are each independently selected from hydrogen or deuterium, $X_2$ are each independently selected from $CH_3$ or $CD_3$.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_{10}$ are hydrogen, $X_2$ is $CD_3$, $R_1$ and $R_2$ are each independently selected from hydrogen or deuterium, $X_1$ are each independently selected from $CH_3$ or $CD_3$.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_{10}$ are hydrogen, $R_1$ is deuterium, $R_2$ are each independently selected from hydrogen or deuterium, $X_1$ and $X_2$ are each independently selected from $CH_3$ or $CD_3$.

In some embodiments, alternatively, the present disclosure relates to a compound of formula (I-A), or the tautomers, stereoisomers, prodrugs, crystal forms, pharmaceutically acceptable salts, hydrates or solvates thereof, wherein, $Y_1'$-$Y_{11}'$ are hydrogen, $R_3$-$R_{10}$ are hydrogen, $R_1$ and $R_2$ are deuterium, $X_1$ and $X_2$ are each independently selected from $CH_3$ or $CD_3$.

In another embodiment, the present disclosure relates to a compound of formula (II-A), or the tautomers, stereoisomers, prodrugs, crystal forms, pharmaceutically acceptable salts, hydrates or solvates thereof:

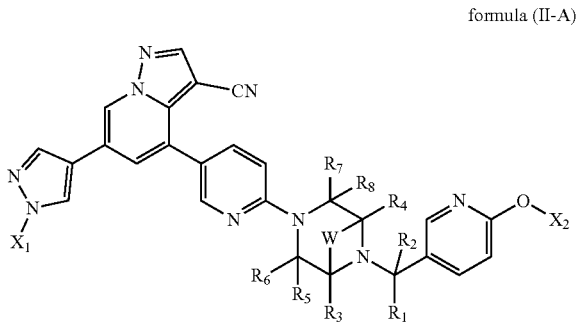

formula (II-A)

wherein,
W is $CR_9R_{10}$;
$R_1$, $R_2$, $R_3$, $R_4$, $R_5$, $R_6$, $R_7$, $R_8$, $R_9$ and $R_{10}$ are each independently selected from hydrogen or deuterium;
$X_1$ and $X_2$ are each independently selected from $CH_3$, $CD_3$, $CHD_2$ or $CH_2D$;
provided that the above compound has at least one deuterium atom.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_8$ are deuterium, $R_1$, $R_2$, $R_9$ and $R_{10}$ are each independently selected from hydrogen or deuterium, $X_1$ and $X_2$ are each independently selected from $CH_3$, $CD_3$, $CHD_2$ or $CH_2D$.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_9$ and $R_{10}$ are deuterium, $R_1$-$R_8$ are each independently selected from hydrogen or deuterium, $X_1$ and $X_2$ are each independently selected from $CH_3$, $CD_3$, $CHD_2$ or $CH_2D$.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_{10}$ are hydrogen, $R_1$ and $R_2$ are each independently selected from hydrogen or deuterium, $X_1$ and $X_2$ are each independently selected from $CH_3$, $CD_3$, $CHD_2$ or $CH_2D$, provided that the above compound has at least one deuterium atom.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_{10}$ are hydrogen, $R_1$ and $R_2$ are each independently selected from hydrogen or deuterium, $X_1$ and $X_2$ are each independently selected from $CH_3$ or $CD_3$, provided that the above compound has at least one deuterium atom.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_{10}$ are hydrogen, $X_1$ is $CD_3$, $R_1$ and $R_2$ are each independently selected from hydrogen or deuterium, $X_2$ are each independently selected from $CH_3$ or $CD_3$.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_{10}$ are hydrogen, $X_2$ is $CD_3$, $R_1$ and $R_2$ are each independently selected from hydrogen or deuterium, $X_1$ are each independently selected from $CH_3$ or $CD_3$.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_{10}$ are hydrogen, $R_1$ is deuterium, $R_2$ are each independently selected from hydrogen or deuterium, $X_1$ and $X_2$ are each independently selected from $CH_3$ or $CD_3$.

In some embodiments, alternatively, the present disclosure relates to a compound of formula (II-A), or the tautomers, stereoisomers, prodrugs, crystal forms, pharmaceutically acceptable salts, hydrates or solvates thereof, wherein, $R_3$-$R_{10}$ are hydrogen, $R_1$ and $R_2$ are deuterium, $X_1$ and $X_2$ are each independently selected from $CH_3$ or $CD_3$.

In an alternative embodiment, $R_1$ is deuterium; in an alternative embodiment, $R_1$ is hydrogen.

In an alternative embodiment, $R_2$ is deuterium; in an alternative embodiment, $R_2$ is hydrogen.

In an alternative embodiment, $R_1$ and $R_2$ are deuterium; in an alternative embodiment, $R_1$ and $R_2$ are hydrogen.

In an alternative embodiment, $R_3$ and $R_4$ are deuterium; in an alternative embodiment, $R_3$ and $R_4$ are hydrogen.

In an alternative embodiment, $R_5$-$R_8$ are deuterium; in an alternative embodiment, $R_5$-$R_8$ are hydrogen.

In an alternative embodiment, $R_9$ and $R_{10}$ are deuterium; in an alternative embodiment, $R_9$ and $R_{10}$ are hydrogen.

In an alternative embodiment, $X_1$ is $CH_3$; in an alternative embodiment, $X_1$ is $CD_3$.

In an alternative embodiment, $X_2$ is $CH_3$; in an alternative embodiment, $X_2$ is $CD_3$.

In another embodiment, the present disclosure relates to a compound of formula (I-B), or the tautomers, stereoisomers, prodrugs, crystal forms, pharmaceutically acceptable salts, hydrates or solvates thereof:

formula (I-B)

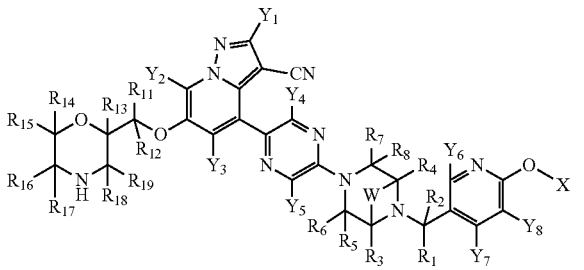

wherein,

W is $CR_9R_{10}$;

$R_1, R_2, R_3, R_4, R_5, R_6, R_7, R_8, R_9, R_{10}, R_{11}, R_{12}, R_{13}, R_{14}, R_{15}, R_{16}, R_{17}, R_{18}$ and $R_{19}$ are each independently selected from hydrogen or deuterium;

$Y_1, Y_2, Y_3, Y_4, Y_5, Y_6, Y_7$ and $Y_8$ are each independently selected from hydrogen, deuterium, halogen or trifluoromethyl;

X is selected from $CH_3$, $CD_3$, $CHD_2$ or $CH_2D$;

provided that the above compound has at least one deuterium atom.

As a preferred embodiment of the present disclosure, the isotope content of deuterium at the deuterated position is at least greater than the 0.015% natural isotope content of deuterium, alternatively greater than 30%, alternatively greater than 50%, alternatively greater than 75%, alternatively greater than 95%, alternatively greater than 99%.

In a specific embodiment, "$R_1, R_2, R_3, R_4, R_5, R_6, R_7, R_8, R_9, R_{10}, R_{11}, R_{12}, R_{13}, R_{14}, R_{15}, R_{16}, R_{17}, R_{18}$ and $R_{19}$ are each independently selected from hydrogen or deuterium" includes the technical solutions wherein, $R_1$ is selected from hydrogen or deuterium, $R_2$ is selected from hydrogen or deuterium, $R_3$ is selected from hydrogen or deuterium, and so on, until $R_{19}$ is selected from hydrogen or deuterium. More specifically, the technical solutions wherein, $R_1$ is hydrogen or $R_1$ is deuterium, $R_2$ is hydrogen or $R_2$ is deuterium, $R_3$ is hydrogen or $R_3$ is deuterium, and so on, until $R_{19}$ is hydrogen or $R_{19}$ is deuterium, are included.

In another specific embodiment, "$Y_1, Y_2, Y_3, Y_4, Y_5, Y_6, Y_7$ and $Y_8$ are each independently selected from hydrogen, deuterium, halogen or trifluoromethyl" includes the technical solutions wherein, $Y_1$ is selected from hydrogen, deuterium, halogen or trifluoromethyl, $Y_2$ is selected from hydrogen, deuterium, halogen or trifluoromethyl, $Y_3$ is selected from hydrogen, deuterium, halogen or trifluoromethyl, and so on, until $Y_8$ is selected from hydrogen, deuterium, halogen or trifluoromethyl. More specifically, the technical solutions wherein, $Y_1$ is hydrogen, $Y_1$ is deuterium, $Y_1$ is halogen (F, Cl, Br or I), or $Y_1$ is trifluoromethyl, $Y_2$ is hydrogen, $Y_2$ is deuterium, $Y_2$ is halogen (F, Cl, Br or I), or $Y_2$ is trifluoromethyl, $Y_3$ is hydrogen, $Y_3$ is deuterium, $Y_3$ is halogen (F, Cl, Br or I), or $Y_3$ is trifluoromethyl, and so on, until $Y_8$ is hydrogen, $Y_8$ is deuterium, $Y_8$ is halogen (F, Cl, Br or I), or $Y_8$ is trifluoromethyl, are included.

In another specific embodiment, "X is selected from $CH_3$, $CD_3$, $CHD_2$ or $CH_2D$" includes the technical solutions wherein, X is selected from $CH_3$, $CD_3$, $CHD_2$ or $CH_2D$. More specifically, the technical solutions wherein, X is $CH_3$, X is $CD_3$, X is $CHD_2$ or X is $CH_2D$, are included.

In another specific embodiment, the present disclosure relates to a compound of formula (I-B-a) or formula (I-B-b), or the tautomers, stereoisomers, prodrugs, crystal forms, pharmaceutically acceptable salts, hydrates or solvates thereof:

formula (I-B-a)

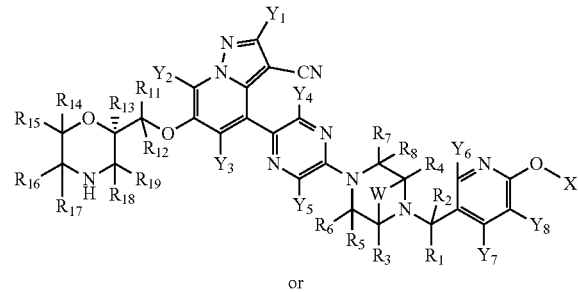

or formula (I-B-b)

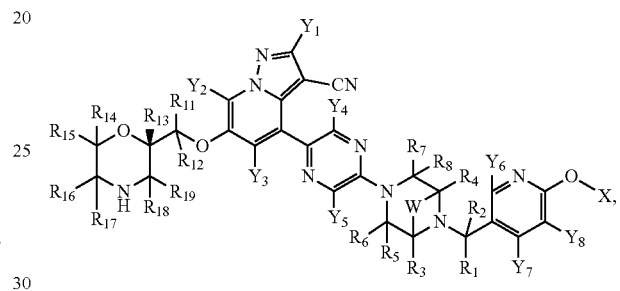

wherein,

W is $CR_9R_{10}$;

$R_1, R_2, R_3, R_4, R_5, R_6, R_7, R_8, R_9, R_{10}, R_{11}, R_{12}, R_{13}, R_{14}, R_{15}, R_{16}, R_{17}, R_{18}$ and $R_{19}$ are each independently selected from hydrogen or deuterium;

$Y_1, Y_2, Y_3, Y_4, Y_5, Y_6, Y_7$ and $Y_8$ are each independently selected from hydrogen, deuterium, halogen or trifluoromethyl;

X is selected from $CH_3$, $CD_3$, $CHD_2$ or $CH_2D$;

provided that the above compound has at least one deuterium atom.

In some embodiments of formula (I-B), (I-B-a) and (I-B-b), alternatively, $Y_1, Y_2, Y_3, Y_4, Y_5, Y_6, Y_7$ and $Y_8$ are each independently selected from hydrogen or deuterium.

In some embodiments of formula (I-B), (I-B-a) and (I-B-b), alternatively, X is selected from $CH_3$ or $CD_3$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_1$-$R_{19}$ are each independently selected from hydrogen or deuterium, X is selected from $CH_3$, $CD_3$, $CHD_2$ or $CH_2D$, provided that the above compound has at least one deuterium atom.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are deuterium, $R_1$, $R_2$ and $R_{11}$-$R_{19}$ are each independently selected from hydrogen or deuterium, X is selected from $CH_3$, $CD_3$, $CHD_2$ or $CH_2D$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are deuterium, $R_1$, $R_2$ and $R_{11}$-$R_{19}$ are each independently selected from hydrogen or deuterium, X is selected from $CH_3$ or $CD_3$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_{13}$-$R_{19}$ are deuterium, $R_1$-$R_{12}$ are each independently selected from hydrogen or deuterium, X is selected from $CH_3$, $CD_3$, $CHD_2$ or $CH_2D$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_{13}$-$R_{19}$ are deuterium, $R_1$-$R_{12}$ are each independently selected from hydrogen or deuterium, X is selected from $CH_3$ or $CD_3$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are hydrogen, $R_1$, $R_2$ and $R_{11}$-$R_{19}$ are each independently selected from hydrogen or deuterium, X is selected from $CH_3$, $CD_3$, $CHD_2$ or $CH_2D$, provided that the above compound has at least one deuterium atom.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are hydrogen, $R_1$, $R_2$ and $R_{11}$-$R_{19}$ are each independently selected from hydrogen or deuterium, X is selected from $CH_3$ or $CD_3$, provided that the above compound has at least one deuterium atom.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are hydrogen, X is selected from $CD_3$, $R_1$, $R_2$ and $R_{11}$-$R_{19}$ are each independently selected from hydrogen or deuterium.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are hydrogen, $R_1$ and $R_2$ are deuterium, $R_{11}$-$R_{19}$ are each independently selected from hydrogen or deuterium, X is selected from $CH_3$ or $CD_3$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_3$-$R_{10}$ are hydrogen, $R_{11}$ 1 and $R_{12}$ are deuterium, $R_1$, $R_2$ and $R_{13}$-$R_{19}$ are each independently selected from hydrogen or deuterium, X is selected from $CH_3$ or $CD_3$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_u$-$Y_8$ are hydrogen, $R_{13}$-$R_{19}$ are hydrogen, $R_{11}$-$R_{12}$ are each independently selected from hydrogen or deuterium, X is selected from $CH_3$, $CD_3$, $CHD_2$ or $CH_2D$, provided that the above compound has at least one deuterium atom.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_{13}$-$R_{19}$ are hydrogen, $R_1$-$R_{12}$ are each independently selected from hydrogen or deuterium, X is selected from $CH_3$ or $CD_3$, provided that the above compound has at least one deuterium atom.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_{13}$-$R_{19}$ are hydrogen, X is selected from $CD_3$, $R_1$-$R_{12}$ are each independently selected from hydrogen or deuterium.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_{13}$-$R_{19}$ are hydrogen, $R_1$ and $R_2$ are deuterium, $R_3$-$R_{12}$ are each independently selected from hydrogen or deuterium, X is selected from $CH_3$ or $CD_3$.

In some embodiments, alternatively, the present disclosure relates to a compound of formula (I-B), (I-B-a) and (I-B-b), or the tautomers, stereoisomers, prodrugs, crystal forms, pharmaceutically acceptable salts, hydrates or solvates thereof, wherein, $Y_1$-$Y_8$ are hydrogen, $R_{13}$-$R_{19}$ are hydrogen, $R_{11}$ and $R_{12}$ are deuterium, $R_1$-$R_{10}$ are each independently selected from hydrogen or deuterium, X is selected from $CH_3$ or $CD_3$.

In another embodiment, the present disclosure relates to a compound of formula (II-B), or the tautomers, stereoisomers, prodrugs, crystal forms, pharmaceutically acceptable salts, hydrates or solvates thereof:

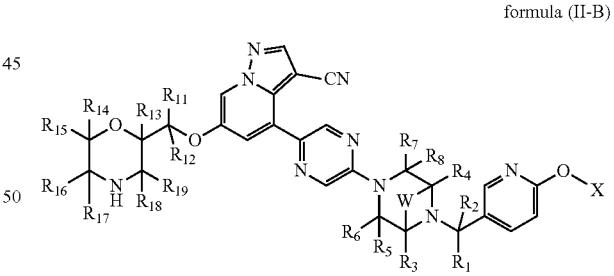

formula (II-B)

wherein,
W is $CR_9R_{10}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ and $R_{19}$ are each independently selected from hydrogen or deuterium;
X is selected from $CH_3$, $CD_3$, $CHD_2$ or $CH_2D$;
provided that the above compound has at least one deuterium atom.

In another specific embodiment, the present disclosure relates to a compound of formula (II-B-a) or formula (II-B-b), or the tautomers, stereoisomers, prodrugs, crystal forms, pharmaceutically acceptable salts, hydrates or solvates thereof:

formula (II-B-a)

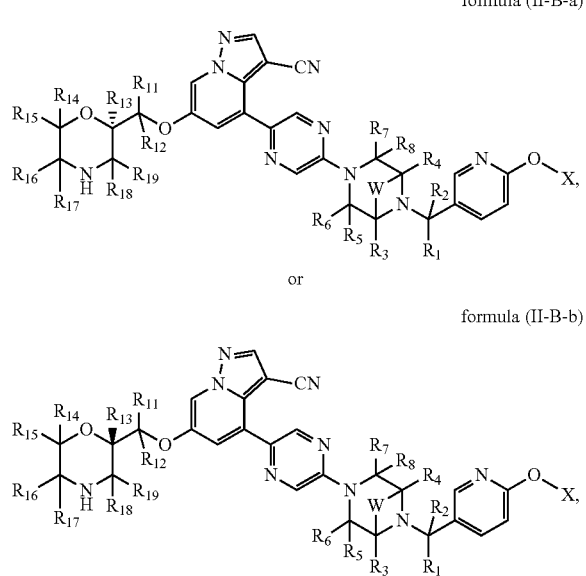

or formula (II-B-b)

wherein,
W is $CR_9R_{10}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ and $R_{19}$ are each independently selected from hydrogen or deuterium;
X is selected from $CH_3$, $CD_3$, $CHD_2$ or $CH_2D$;
provided that the above compound has at least one deuterium atom.

In some embodiments of formula (II-B), (II-B-a) and (II-B-b), alternatively, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_1$-$R_{19}$ are each independently selected from hydrogen or deuterium, X is selected from $CH_3$, $CD_3$, $CHD_2$ or $CH_2D$, provided that the above compound has at least one deuterium atom.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are deuterium, $R_1$, $R_2$ and $R_{11}$-$R_{19}$ are each independently selected from hydrogen or deuterium, X is selected from $CH_3$, $CD_3$, $CHD_2$ or $CH_2D$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are deuterium, $R_1$, $R_2$ and $R_{11}$-$R_{19}$ are each independently selected from hydrogen or deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are deuterium, $R_1$-$R_{12}$ are each independently selected from hydrogen or deuterium, X is selected from $CH_3$, $CD_3$, $CHD_2$ or $CH_2D$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are deuterium, $R_1$-$R_{12}$ are each independently selected from hydrogen or deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are hydrogen, $R_1$, $R_2$ and $R_{11}$-$R_{19}$ are each independently selected from hydrogen or deuterium, X is selected from $CH_3$, $CD_3$, $CHD_2$ or $CH_2D$, provided that the above compound has at least one deuterium atom.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are hydrogen, $R_1$, $R_2$ and $R_{11}$-$R_{19}$ are each independently selected from hydrogen or deuterium, X is selected from $CH_3$ or $CD_3$, provided that the above compound has at least one deuterium atom.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are hydrogen, X is $CD_3$, $R_1$, $R_2$ and $R_{11}$-$R_{19}$ are each independently selected from hydrogen or deuterium.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are hydrogen, 121 and $R_2$ are deuterium, $R_{11}$-$R_{19}$ are each independently selected from hydrogen or deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ are hydrogen, $R_{11}$ and $R_{12}$ are deuterium, $R_1$, $R_2$ and $R_{13}$-$R_{19}$ are each independently selected from hydrogen or deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are hydrogen, $R_1$-$R_{12}$ are each independently selected from hydrogen or deuterium, X is selected from $CH_3$, $CD_3$, $CHD_2$ or $CH_2D$, provided that the above compound has at least one deuterium atom.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are hydrogen, $R_1$-$R_{12}$ are each independently selected from hydrogen or deuterium, X is selected from $CH_3$ or $CD_3$, provided that the above compound has at least one deuterium atom.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are hydrogen, X is $CD_3$, $R_1$-$R_{12}$ are each independently selected from hydrogen or deuterium.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are hydrogen, $R_1$ and $R_2$ are deuterium, $R_3$-$R_{12}$ are each independently selected from hydrogen or deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_{13}$-$R_{19}$ are hydrogen, $R_{11}$ and $R_{12}$ are deuterium, $R_1$-$R_{10}$ are each independently selected from hydrogen or deuterium, X is selected from $CH_3$ or $CD_3$. In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, $R_1$, $R_2$, $R_{11}$ and $R_{12}$ are each independently selected from hydrogen or deuterium, X is selected from $CH_3$ or $CD_3$, provided that the above compound has at least one deuterium atom.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, X is $CD_3$, $R_1$, $R_2$, $R_{11}$ and $R_{12}$ are each independently selected from hydrogen or deuterium.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, X is $CD_3$, $R_1$ and $R_2$ are deuterium, $R_{11}$ and $R_{12}$ are each independently selected from hydrogen or deuterium.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, X is $CD_3$, $R_{11}$ and $R_{12}$ are deuterium, $R_1$ and $R_2$ are each independently selected from hydrogen or deuterium.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, $R_1$ and $R_2$ are deuterium, $R_{11}$ and $R_{12}$ are each independently selected from hydrogen or deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, $R_1$ and $R_2$ are deuterium, $R_{11}$ and $R_{12}$ are deuterium, X is selected from $CH_3$ or $CD_3$.

In some embodiments, alternatively, the present disclosure relates to a compound of formula (II-B), (II-B-a) and (II-B-b), or the tautomers, stereoisomers, prodrugs, crystal forms, pharmaceutically acceptable salts, hydrates or solvates thereof, wherein, $R_3$-$R_{10}$ and $R_{13}$-$R_{19}$ are hydrogen, $R_{11}$ and $R_{12}$ are deuterium, $R_1$ and $R_2$ are each independently selected from hydrogen or deuterium, X is selected from $CH_3$ or $CD_3$.

In an alternative embodiment, $R_1$ and $R_2$ are deuterium; in an alternative embodiment, $R_1$ and $R_2$ are hydrogen.

In an alternative embodiment, $R_3$ and $R_4$ are deuterium; in an alternative embodiment, $R_3$ and $R_4$ are hydrogen.

In an alternative embodiment, $R_5$-$R_8$ are deuterium; in an alternative embodiment, $R_5$-$R_8$ are hydrogen.

In an alternative embodiment, $R_9$ and $R_{10}$ are deuterium; in an alternative embodiment, $R_9$ and $R_{10}$ are hydrogen.

In an alternative embodiment, $R_{11}$ and $R_{12}$ are deuterium; in an alternative embodiment, $R_{11}$ and $R_{12}$ are hydrogen.

In an alternative embodiment, $R_{13}$ is deuterium; in an alternative embodiment, $R_{13}$ are hydrogen.

In an alternative embodiment, $R_{14}$-$R_{19}$ are deuterium; in an alternative embodiment, $R_{14}$-$R_{19}$ are hydrogen.

In an alternative embodiment, X is $CH_3$; in an alternative embodiment, X is $CD_3$.

In another embodiment, the present disclosure relates to a compound of formula (I-C), or the tautomers, stereoisomers, prodrugs, crystal forms, pharmaceutically acceptable salts, hydrates or solvates thereof:

formula (I-C)

wherein,

W is $CR_9R_{10}$;

$R_1$, $R_2$, $R_3$, $R_4$, $R_5$, $R_6$, $R_7$, $R_8$, $R_9$, $R_{10}$, $R_{20}$ and $R_{21}$ are each independently selected from hydrogen or deuterium;

$Y_1''$, $Y_2''$, $Y_3''$, $Y_4''$, $Y_5''$, $Y_6''$, $Y_7''$, $Y_8''$ and $Y_9''$ are each independently selected from hydrogen, deuterium, halogen or trifluoromethyl;

X, $X_3$ and $X_4$ are each independently selected from $CH_3$, $CD_3$, $CHD_2$ or $CH_2D$;

provided that the above compound has at least one deuterium atom.

As a preferred embodiment of the present disclosure, the isotope content of deuterium at the deuterated position is at least greater than the 0.015% natural isotope content of deuterium, alternatively greater than 30%, alternatively greater than 50%, alternatively greater than 75%, alternatively greater than 95%, alternatively greater than 99%.

In a specific embodiment, "$R_1$, $R_2$, $R_3$, $R_4$, $R_5$, $R_6$, $R_7$, $R_8$, $R_9$, $R_{10}$, $R_{20}$ and $R_{21}$ are each independently selected from hydrogen or deuterium" includes the technical solutions wherein, $R_1$ is selected from hydrogen or deuterium, $R_2$ is selected from hydrogen or deuterium, $R_3$ is selected from hydrogen or deuterium, and so on, until $R_{10}$ is selected from hydrogen or deuterium, and $R_{20}$ is selected from hydrogen or deuterium, $R_{21}$ is selected from hydrogen or deuterium. More specifically, the technical solutions wherein, $R_1$ is hydrogen or $R_1$ is deuterium, $R_2$ is hydrogen or $R_2$ is deuterium, $R_3$ is hydrogen or $R_3$ is deuterium, and so on, until $R_{10}$ is hydrogen or $R_{10}$ is deuterium, and $R_{20}$ is hydrogen or $R_{20}$ is deuterium, $R_{21}$ is hydrogen or $R_{21}$ is deuterium, are included.

In another specific embodiment, "$Y_1$", $Y_2$", $Y_3$", $Y_4$", $Y_5$", $Y_6$", $Y_7$", $Y_8$" and $Y_9$" are each independently selected from hydrogen, deuterium, halogen or trifluoromethyl" includes the technical solutions wherein, $Y_1$" is selected from hydrogen, deuterium, halogen or trifluoromethyl, $Y_2$" is selected from hydrogen, deuterium, halogen or trifluoromethyl, $Y_3$" is selected from hydrogen, deuterium, halogen or trifluoromethyl, and so on, until $Y_9$" is selected from hydrogen, deuterium, halogen or trifluoromethyl. More specifically, the technical solutions wherein, $Y_1$" is hydrogen, $Y_1$" is deuterium, $Y_1$" is halogen (F, Cl, Br or I), or $Y_1$" is trifluoromethyl, $Y_2$" is hydrogen, $Y_2$" is deuterium, $Y_2$" is halogen (F, Cl, Br or I), or $Y_2$" is trifluoromethyl, $Y_3$" is hydrogen, $Y_3$" is deuterium, $Y_3$" is halogen (F, Cl, Br or I), or $Y_3$" is trifluoromethyl, and so on, until $Y_9$" is hydrogen, $Y_9$" is deuterium, $Y_9$" is halogen (F, Cl, Br or I), or $Y_9$" is trifluoromethyl, are included.

In another specific embodiment, "X, $X_3$ and $X_4$ are each independently selected from $CH_3$, $CD_3$, $CHD_2$ or $CH_2D$" includes the technical solutions wherein, $X_1$ is selected from $CH_3$, $CD_3$, $CHD_2$ or $CH_2D$, $X_3$ is selected from $CH_3$, $CD_3$, $CHD_2$ or $CH_2D$ and $X_4$ is selected from $CH_3$, $CD_3$, $CHD_2$ or $CH_2D$. More specifically, the technical solutions wherein, X is $CH_3$, X is $CD_3$, X is $CHD_2$ or X is $CH_2D$, $X_3$ is $CH_3$, $X_3$ is $CD_3$, $X_3$ is $CHD_2$ or $X_3$ is $CH_2D$, $X_4$ is $CH_3$, $X_4$ is $CD_3$, $X_4$ is $CHD_2$ or $X_4$ is $CH_2D$, are included.

In some embodiments of formula (I-C), alternatively, $Y_1$", $Y_2$", $Y_3$", $Y_4$", $Y_5$", $Y_6$", $Y_7$", $Y_8$" and $Y_9$" are each independently selected from hydrogen or deuterium.

In some embodiments of formula (I-C), alternatively, X, $X_3$ and $X_4$ are each independently selected from $CH_3$ or $CD_3$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_1$-$R_{10}$, $R_{20}$ and $R_{21}$ are each independently selected from hydrogen or deuterium, X, $X_3$ and $X_4$ are each independently selected from $CH_3$, $CD_3$, $CHD_2$ or $CH_2D$, provided that the above compound has at least one deuterium atom.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are deuterium, $R_1$, $R_2$, $R_{20}$ and $R_{21}$ are each independently selected from hydrogen or deuterium, X, $X_3$ and $X_4$ are each independently selected from $CH_3$, $CD_3$, $CHD_2$ or $CH_2D$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are deuterium, $R_1$, $R_2$, $R_{20}$ and $R_{21}$ are each independently selected from hydrogen or deuterium, X, $X_3$ and $X_4$ are each independently selected from $CH_3$ or $CD_3$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, $R_1$, $R_2$, $R_{20}$ and $R_{21}$ are each independently selected from hydrogen or deuterium, X, $X_3$ and $X_4$ are each independently $CH_3$, $CD_3$, $CHD_2$ or $CH_2D$, provided that the above compound has at least one deuterium atom.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, $R_1$, $R_2$, $R_{20}$ and $R_{21}$ are each independently selected from hydrogen or deuterium, X, $X_3$ and $X_4$ are each independently $CH_3$ or $CD_3$, provided that the above compound has at least one deuterium atom.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, X is $CD_3$, $R_1$, $R_2$, $R_{20}$ and $R_{21}$ are each independently selected from hydrogen or deuterium, $X_3$ and $X_4$ are each independently $CH_3$ or $CD_3$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, $X_3$ is $CD_3$, $R_1$, $R_2$, $R_{20}$ and $R_{21}$ are each independently selected from hydrogen or deuterium, X and $X_4$ are each independently $CH_3$ or $CD_3$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, $X_4$ is $CD_3$, $R_1$, $R_2$, $R_{20}$ and $R_{21}$ are each independently selected from hydrogen or deuterium, X and $X_3$ are each independently $CH_3$ or $CD_3$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, $R_1$ and $R_2$ are deuterium, $R_{20}$ and $R_{21}$ are each independently selected from hydrogen or deuterium, X, $X_3$ and $X_4$ are each independently $CH_3$ or $CD_3$.

In some embodiments, alternatively, the present disclosure relates to a compound of formula (I-C), or the tautomers, stereoisomers, prodrugs, crystal forms, pharmaceutically acceptable salts, hydrates or solvates thereof, wherein, $Y_1$"-$Y_9$" are hydrogen, $R_3$-$R_{10}$ are hydrogen, $R_{20}$ and $R_{21}$ are deuterium, $R_1$ and $R_2$ are each independently selected from hydrogen or deuterium, X, $X_3$ and $X_4$ are each independently $CH_3$ or $CD_3$.

In another embodiment, the present disclosure relates to formula (II-C), or the tautomers, stereoisomers, prodrugs, crystal forms, pharmaceutically acceptable salts, hydrates or solvates thereof:

formula (II-C)

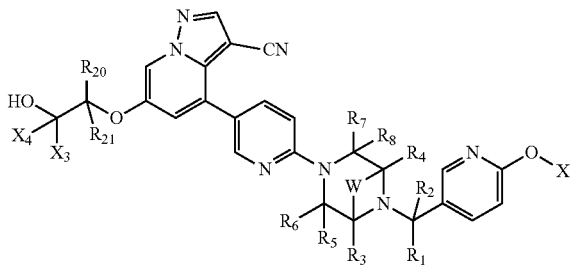

wherein,

W is $CR_9R_{10}$;

$R_1$, $R_2$, $R_3$, $R_4$, $R_5$, $R_6$, $R_7$, $R_8$, $R_9$, $R_{10}$, $R_{20}$ and $R_{21}$ are each independently selected from hydrogen or deuterium;

X, $X_3$ and $X_4$ are each independently selected from $CH_3$, $CD_3$, $CHD_2$ or $CH_2D$;

provided that the above compound has at least one deuterium atom.

In some embodiments of formula (II-C), alternatively, X, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are deuterium, $R_1$, $R_2$, $R_{20}$ and $R_{21}$ are each independently selected from hydrogen or deuterium, X, $X_3$ and $X_4$ are each independently selected from $CH_3$, $CD_3$, $CHD_2$ or $CH_2D$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are deuterium, $R_1$, $R_2$, $R_{20}$ and $R_{21}$ are each independently selected from hydrogen or deuterium, X, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, $R_1$, $R_2$, $R_{20}$ and $R_{21}$ are each independently selected from hydrogen or deuterium, X, $X_3$ and $X_4$ are each independently selected from $CH_3$, $CD_3$, $CHD_2$ or $CH_2D$, provided that the above compound has at least one deuterium atom.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, $R_1$, $R_2$, $R_{20}$ and $R_{21}$ are each independently selected from hydrogen or deuterium, X, $X_3$ and $X_4$ are each independently selected from $CH_3$ or $CD_3$, provided that the above compound has at least one deuterium atom.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, X is selected from $CD_3$, $R_1$, $R_2$, $R_{20}$ and $R_{21}$ are each independently selected from hydrogen or deuterium, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, $X_3$ is $CD_3$, $R_1$, $R_2$, $R_{20}$ and $R_{21}$ are each independently selected from hydrogen or deuterium, X and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, $X_4$ is $CD_3$, $R_1$, $R_2$, $R_{20}$ and $R_{21}$ are each independently selected from hydrogen or deuterium, X and $X_3$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, $R_1$ and $R_2$ are deuterium, $R_{20}$ and $R_{21}$ are each independently selected from hydrogen or deuterium, X, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ are hydrogen, $R_{20}$ and $R_{21}$ are deuterium, $R_1$ and $R_2$ are each independently selected from hydrogen or deuterium, X, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$, $R_{20}$ and $R_{21}$ are hydrogen, $R_1$ and $R_2$ are each independently selected from hydrogen or deuterium, X, $X_3$ and $X_4$ are each independently selected from $CH_3$ or $CD_3$, provided that the above compound has at least one deuterium atom.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$, $R_{20}$ and $R_{21}$ are hydrogen, X is $CD_3$, $R_1$ and $R_2$ are each independently selected from hydrogen or deuterium, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$, $R_{20}$ and $R_{21}$ are hydrogen, X is $CD_3$, $R_1$ and $R_2$ are deuterium, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$, $R_{20}$ and $R_{21}$ are hydrogen, X and $X_3$ is $CD_3$, $R_1$ and $R_2$ are deuterium, $X_4$ is selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$, $R_{20}$ and $R_{21}$ are hydrogen, X and $X_4$ are $CD_3$, $R_1$ and $R_2$ are deuterium, $X_3$ is selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, X and $X_3$ are $CD_3$, $R_1$ and $R_2$ are each independently selected from hydrogen or deuterium, $X_4$ is selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, X, $X_3$ and $X_4$ are $CD_3$, $R_1$ and $R_2$ are each independently selected from hydrogen or deuterium.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, X and $X_4$ are $CD_3$, $R_1$ and $R_2$ are each independently selected from hydrogen or deuterium, $X_3$ is selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, $R_1$ and $R_2$ are deuterium, X, $X_3$ and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, $R_1$ and $R_2$ are deuterium, $X_3$ is $CD_3$, X and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, $R_1$ and $R_2$ are deuterium, $X_4$ is $CD_3$, X and $X_3$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, $X_3$ is $CD_3$, $R_1$ and $R_2$ are each independently selected from hydrogen or deuterium, X and $X_4$ are each independently selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, $X_3$ and $X_4$ are $CD_3$, $R_1$ and $R_2$ are each independently selected from hydrogen or deuterium, X is selected from $CH_3$ or $CD_3$.

In some embodiments, alternatively, the present disclosure relates to a compound of formula (II-C), or the tautomers, stereoisomers, prodrugs, crystal forms, pharmaceutically acceptable salts, hydrates or solvates thereof, wherein, $R_3$-$R_{10}$ and $R_{20}$ and $R_{21}$ are hydrogen, $X_4$ is $CD_3$, $R_1$ and $R_2$ are each independently selected from hydrogen or deuterium, X and $X_3$ are each independently selected from $CH_3$ or $CD_3$. In an alternative embodiment, $R_1$ and $R_2$ are deuterium; in an alternative embodiment, $R_1$ and $R_2$ are hydrogen.

In an alternative embodiment, $R_3$ and $R_4$ are deuterium; in an alternative embodiment, $R_3$ and $R_4$ are hydrogen.

In an alternative embodiment, $R_5$-$R_8$ are deuterium; in an alternative embodiment, $R_5$-$R_8$ are hydrogen.

In an alternative embodiment, $R_{20}$ and $R_{21}$ are deuterium; in an alternative embodiment, $R_{20}$ and $R_{21}$ are hydrogen.

In an alternative embodiment, X is $CH_3$; in an alternative embodiment, X is $CD_3$.

In an alternative embodiment, $X_3$ is $CH_3$; in an alternative embodiment, $X_3$ is $CD_3$.

In an alternative embodiment, $X_4$ is $CH_3$; in an alternative embodiment, $X_4$ is $CD_3$.

As a preferred embodiment of the present disclosure, the compounds are, but not limited to, any of the following structure or a pharmaceutically acceptable salts thereof:

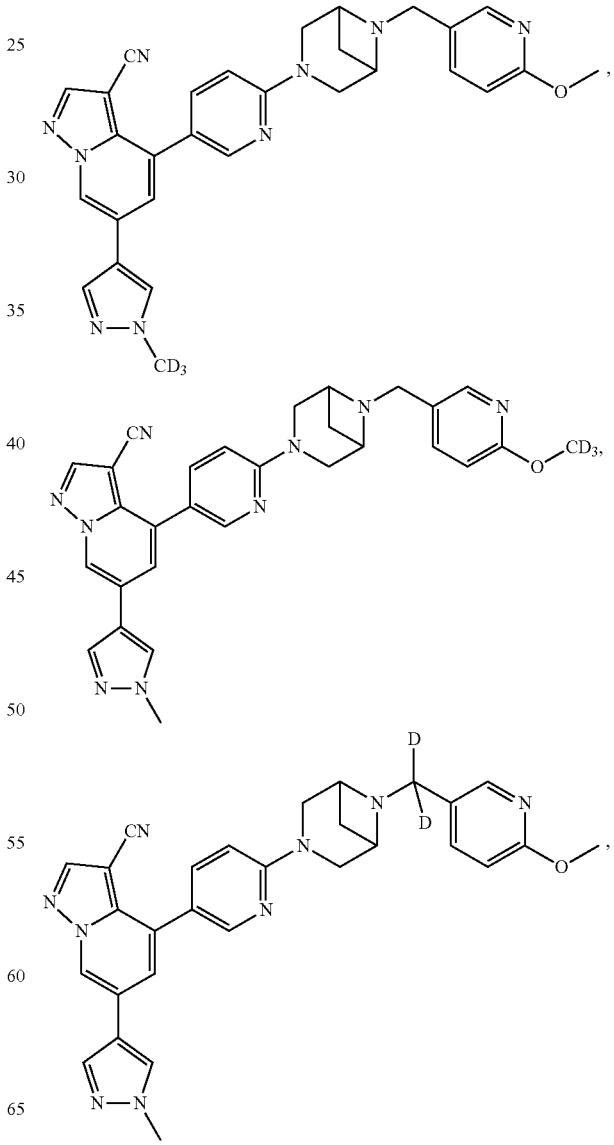

31
-continued
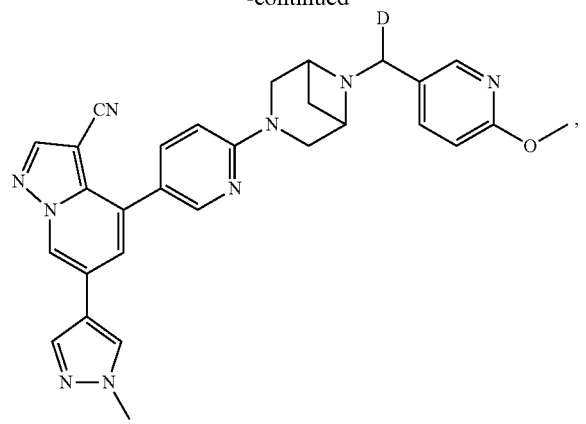
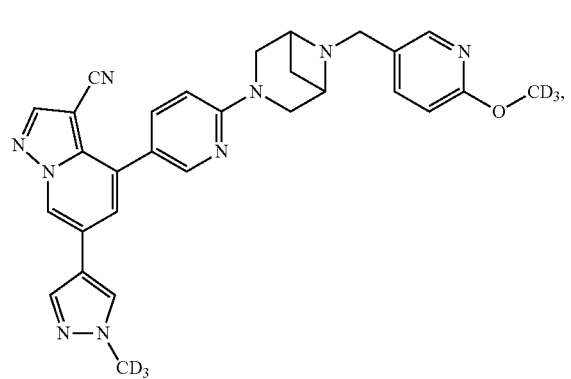
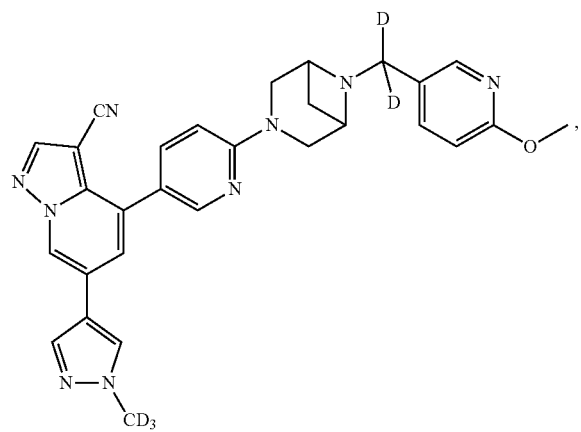
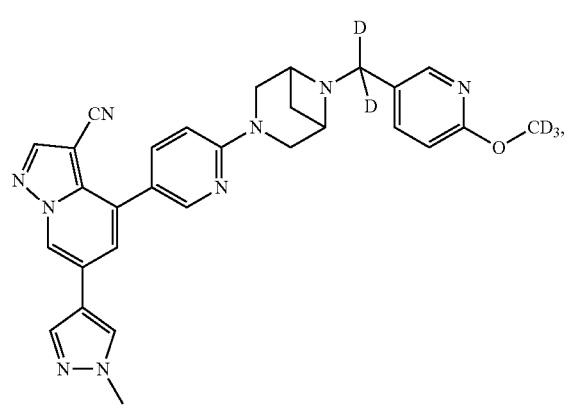
32
-continued
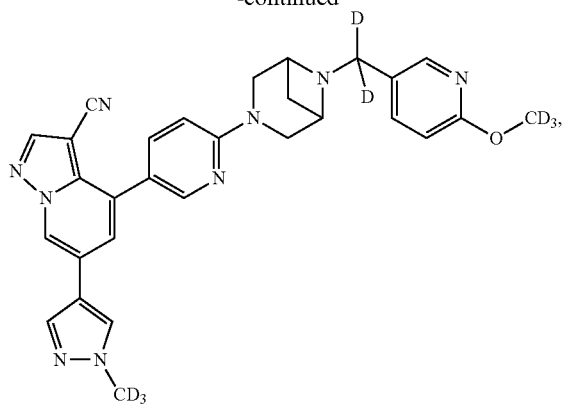
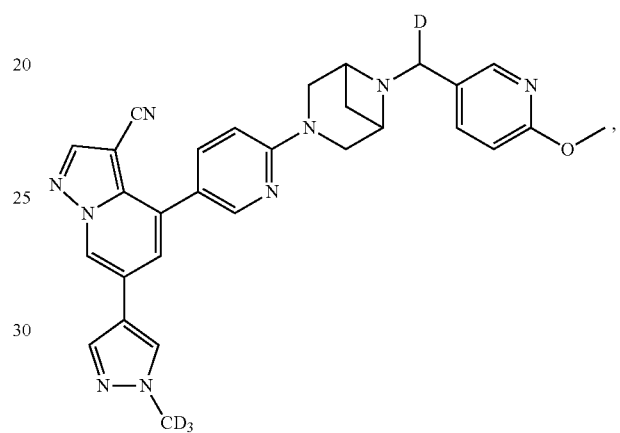
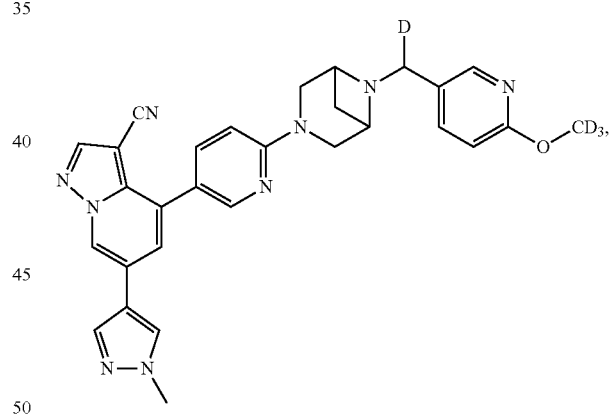
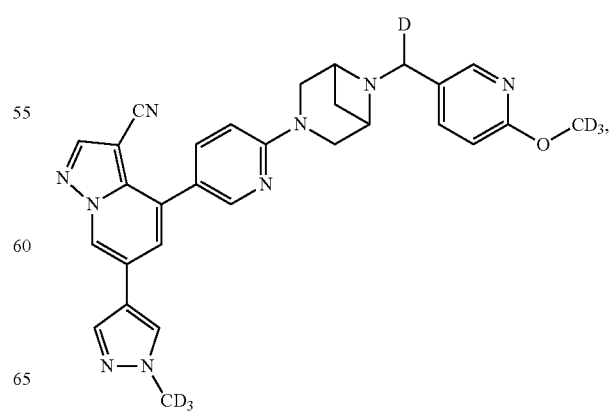

33
-continued
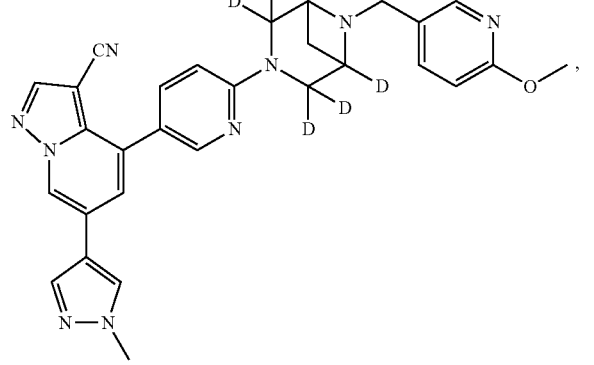
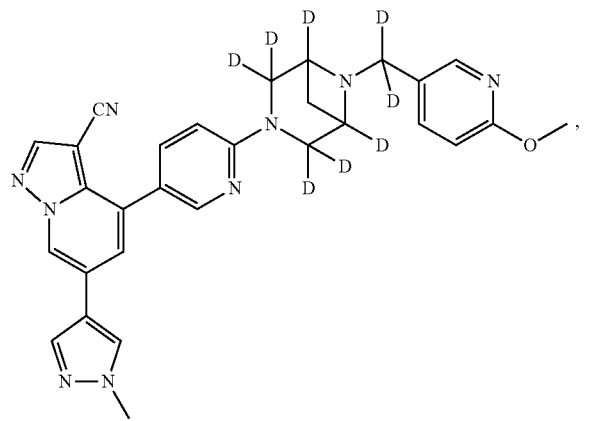
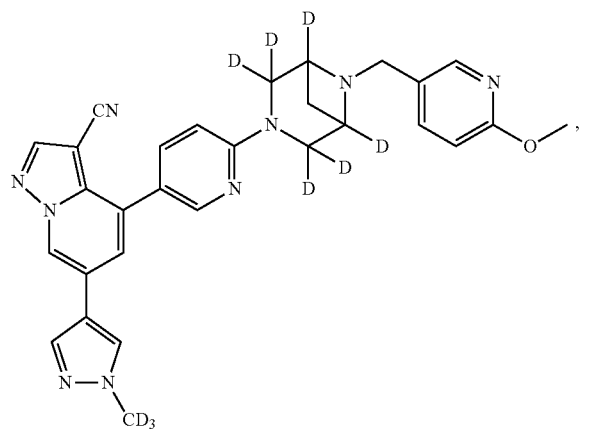
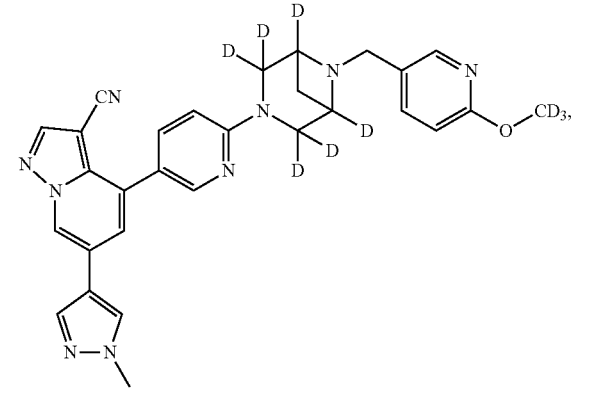
34
-continued
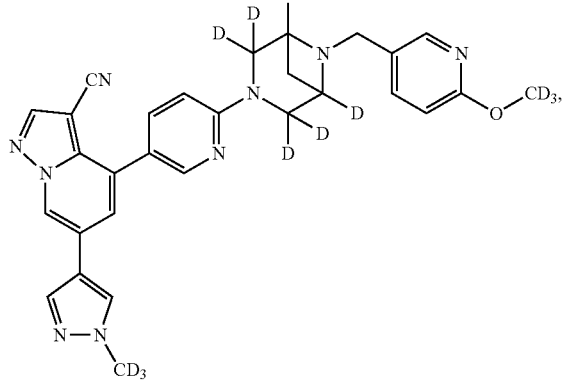
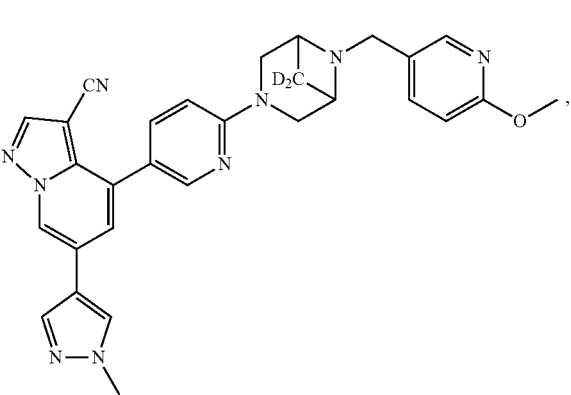
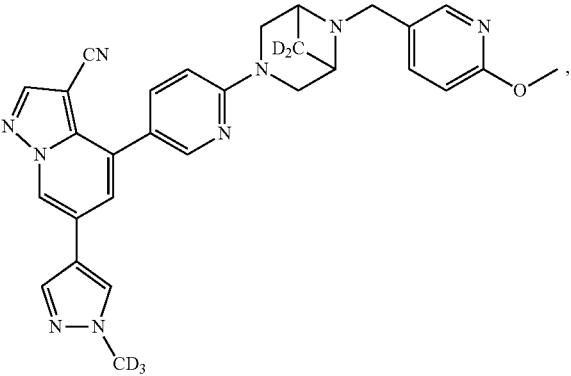
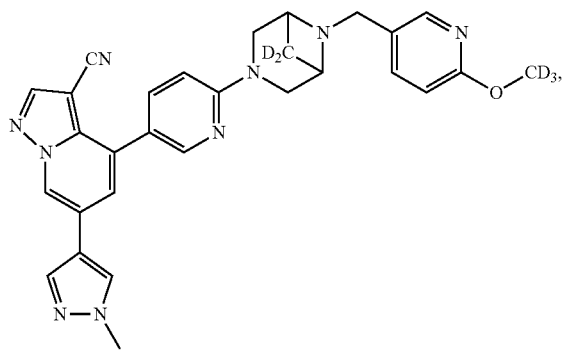

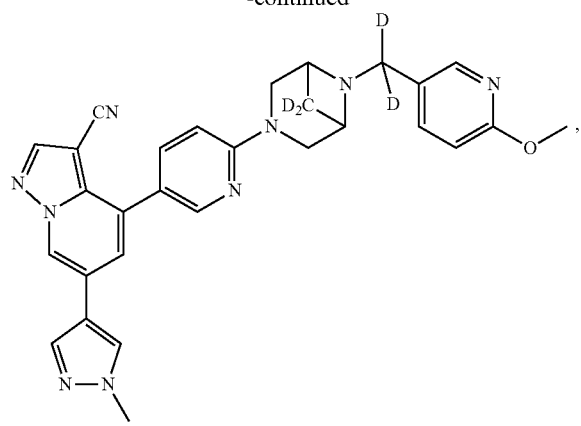
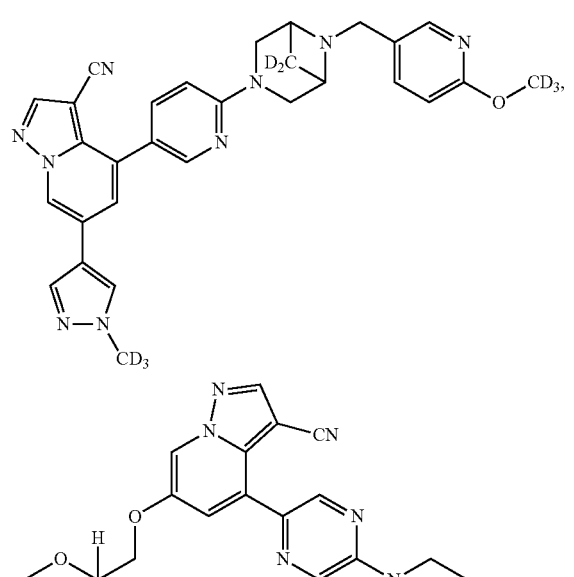
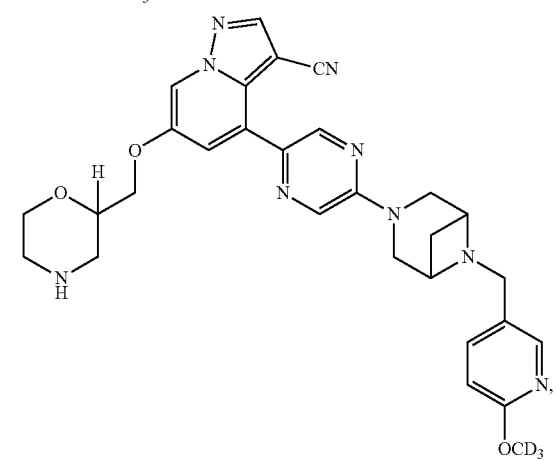
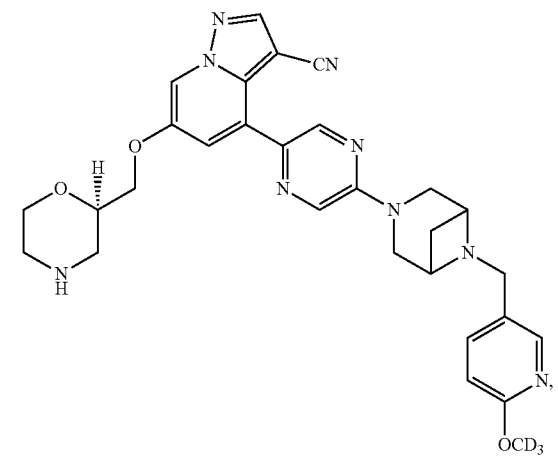
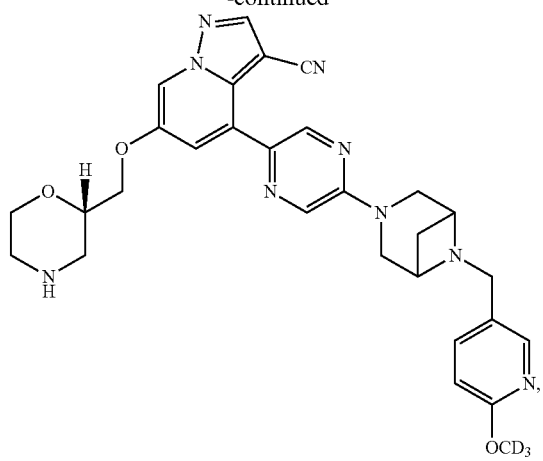
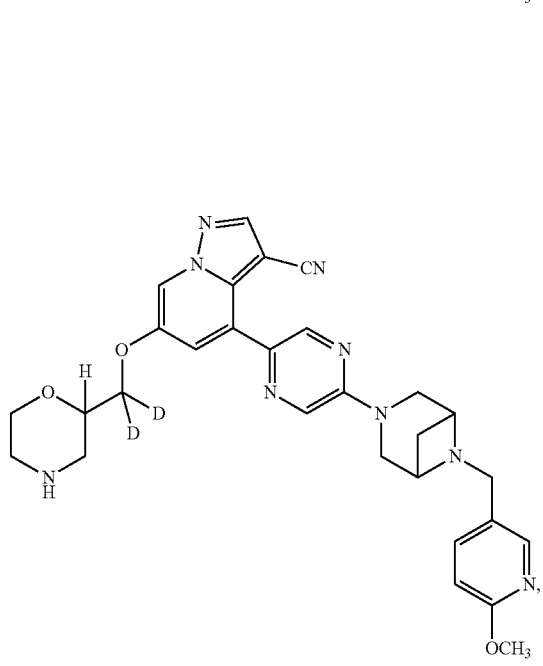
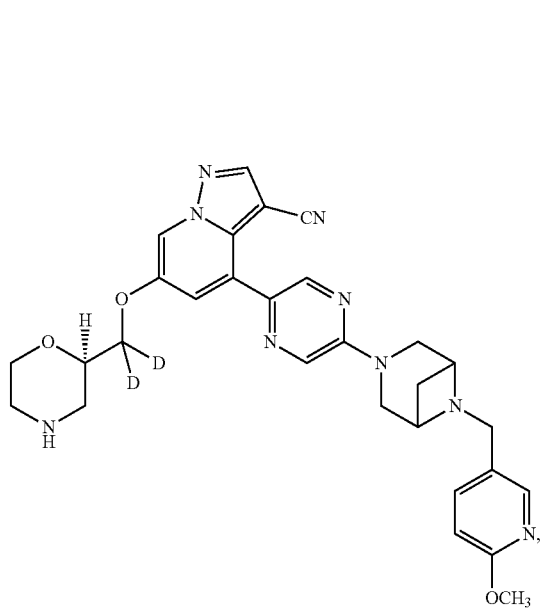

37
-continued
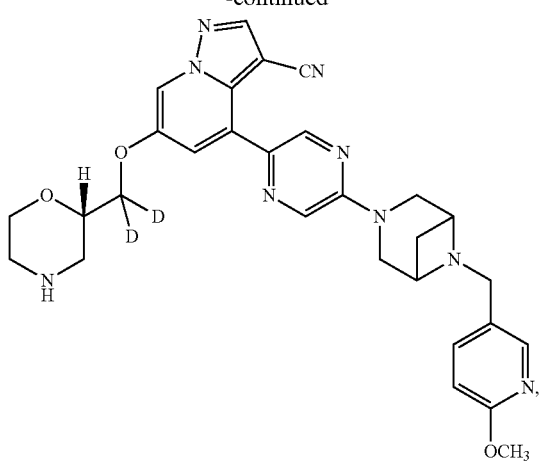
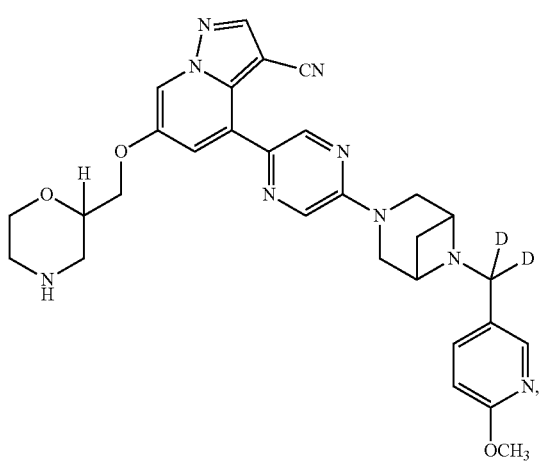
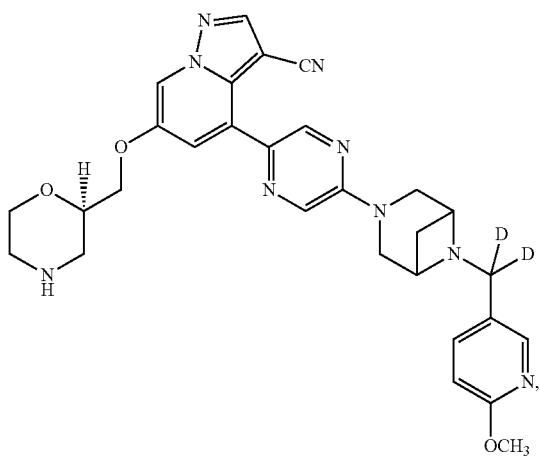
38
-continued
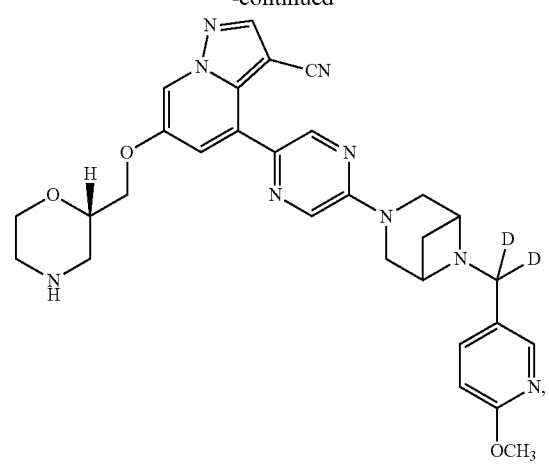
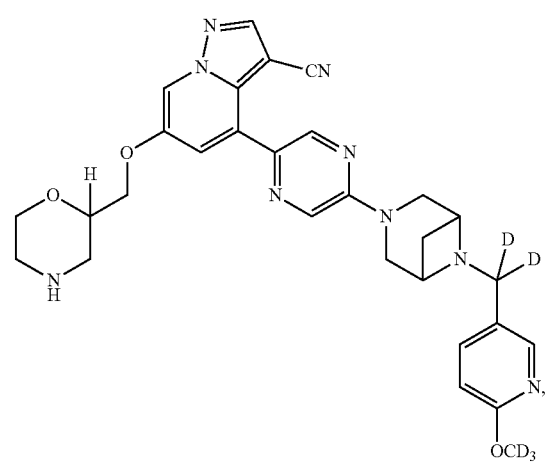
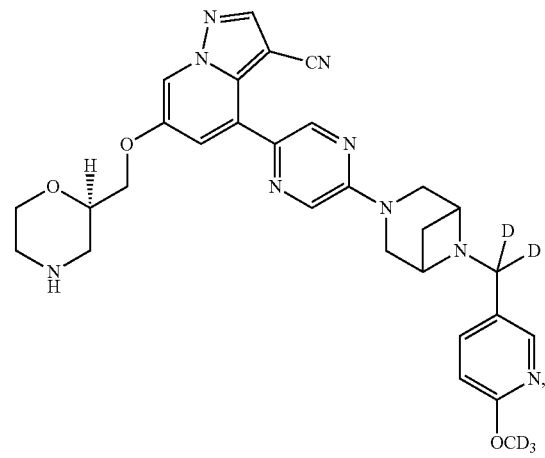

39
-continued
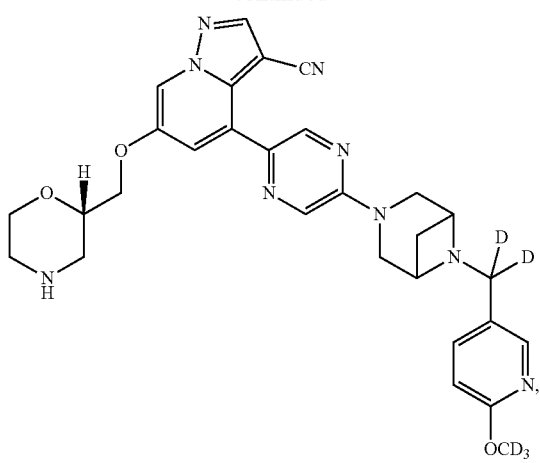
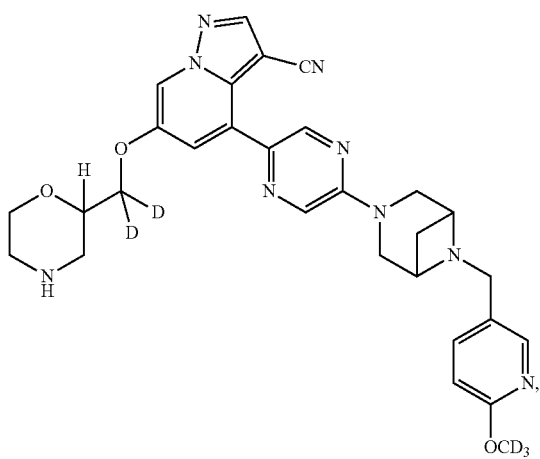
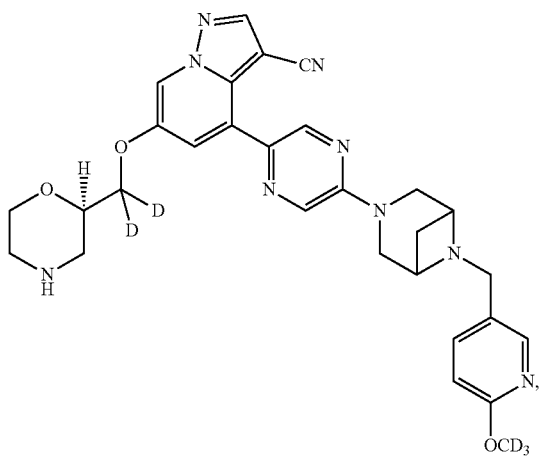
40
-continued
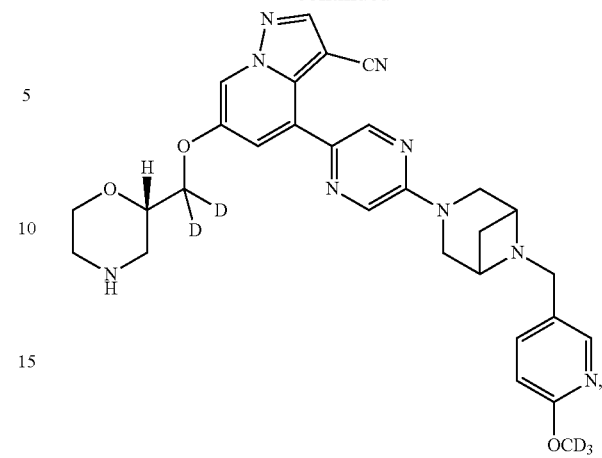
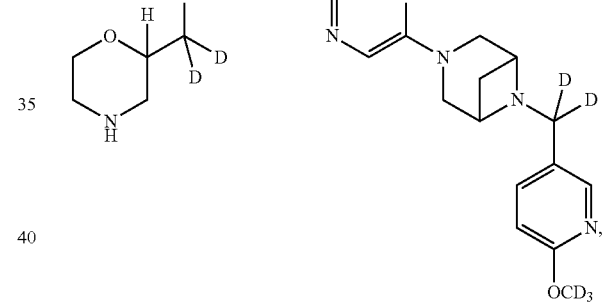
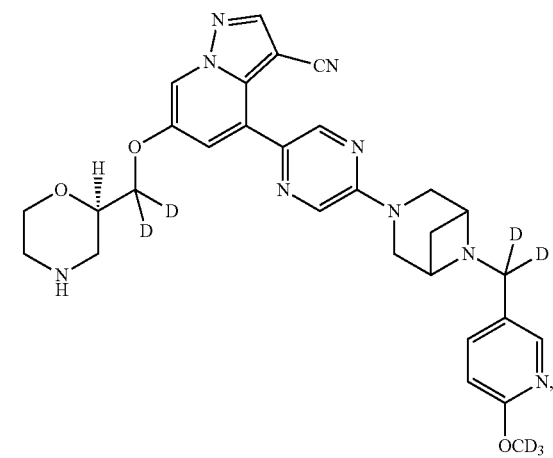

41
-continued
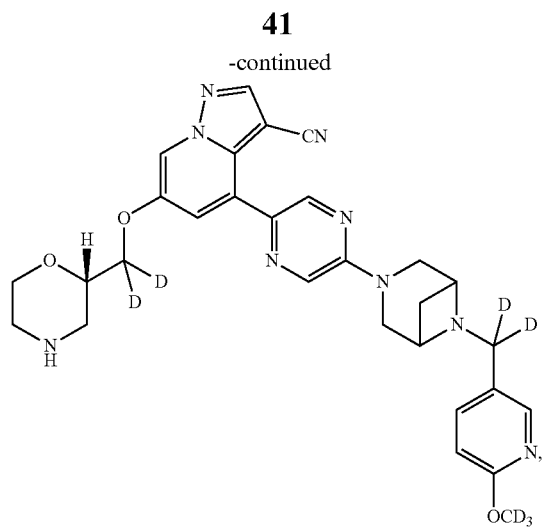
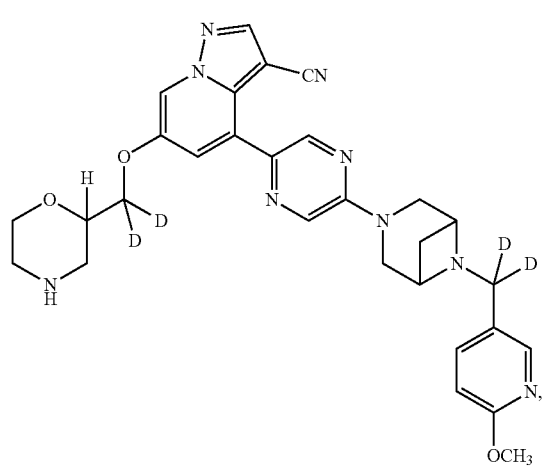
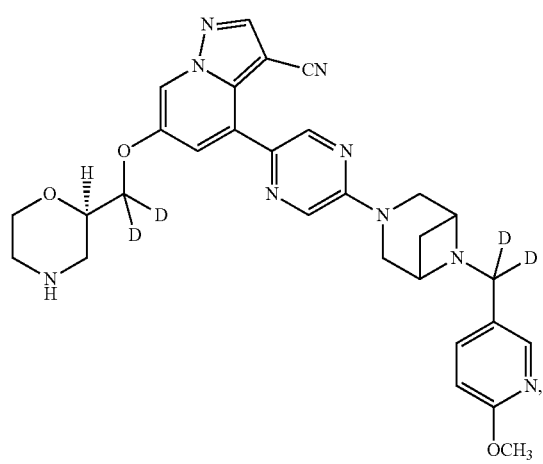
42
-continued
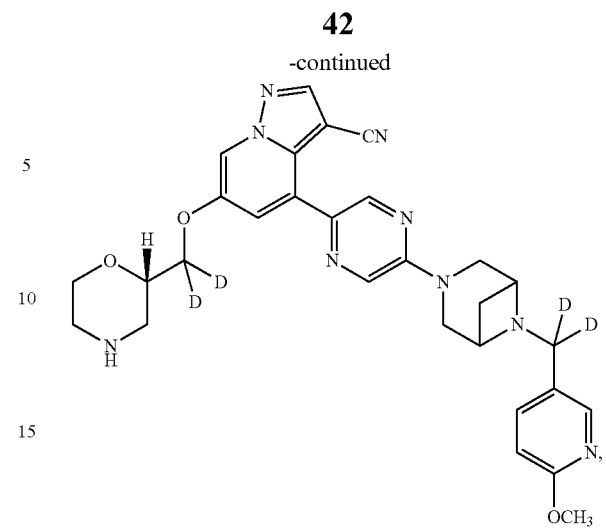
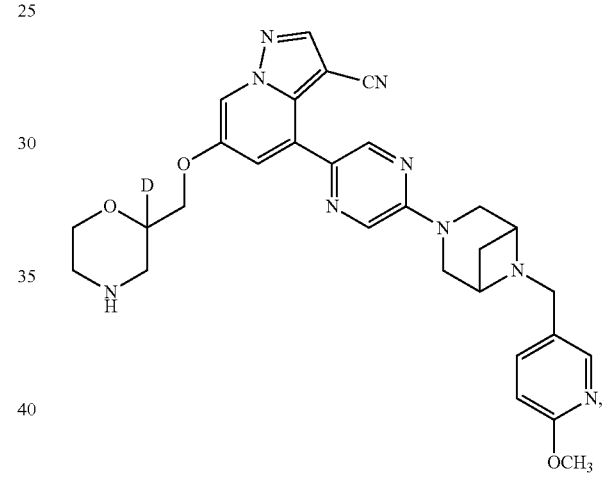
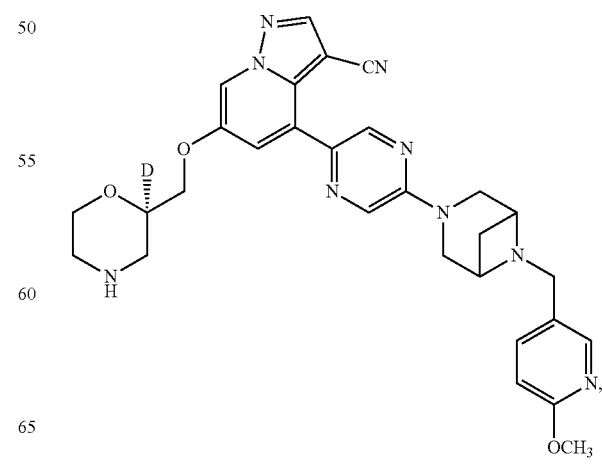

-continued
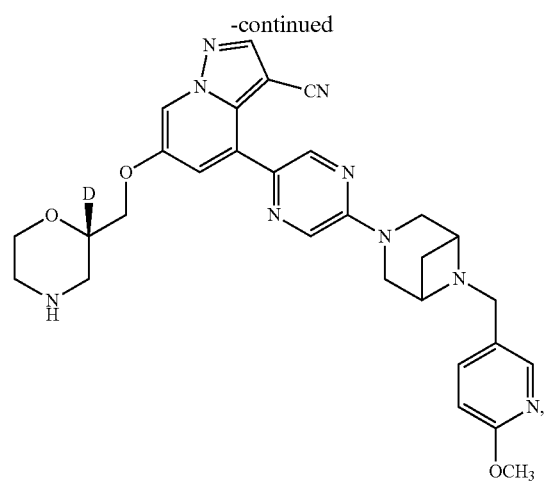
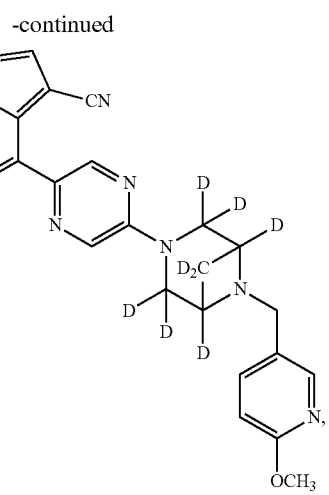
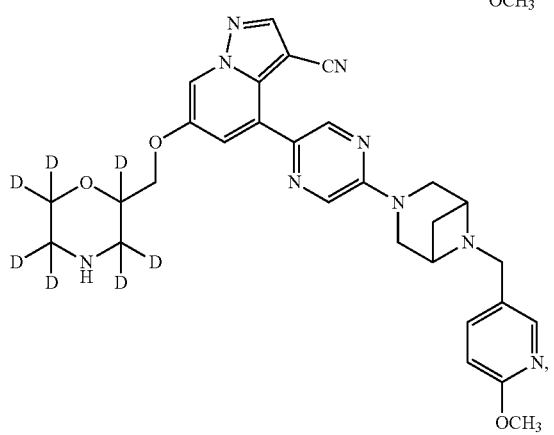
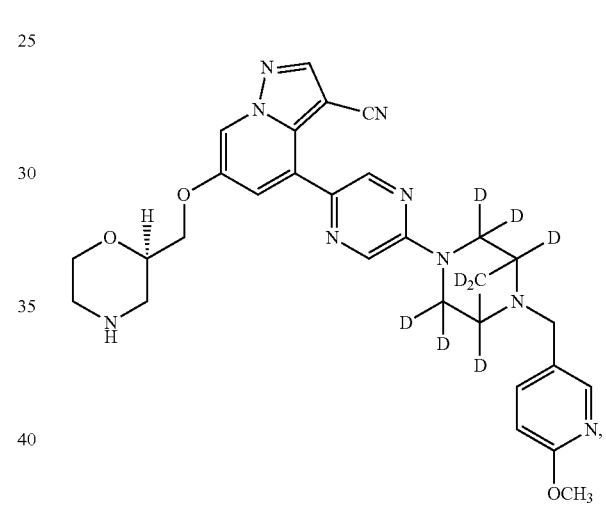
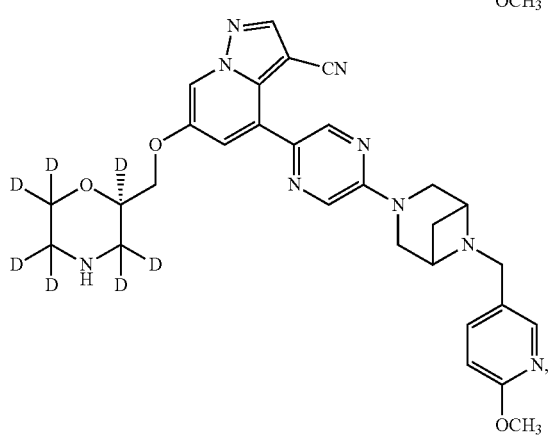
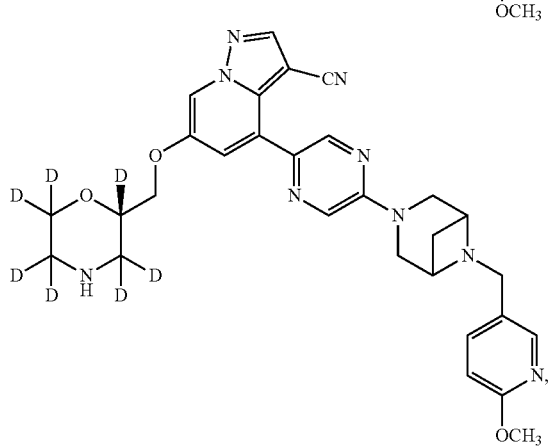
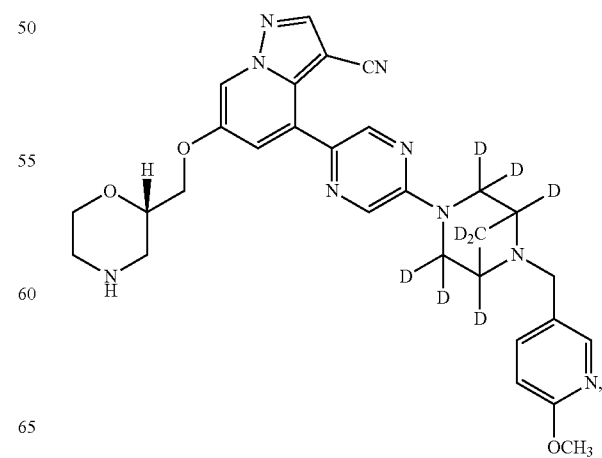

-continued
45
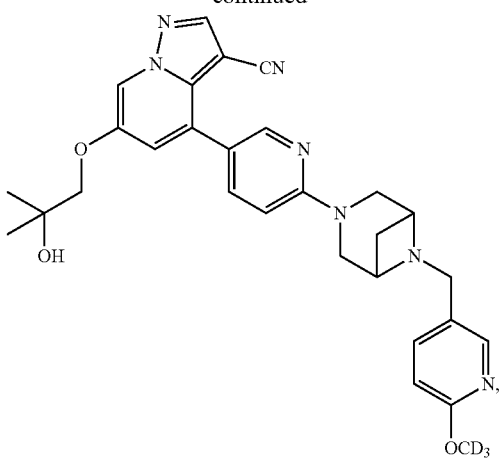
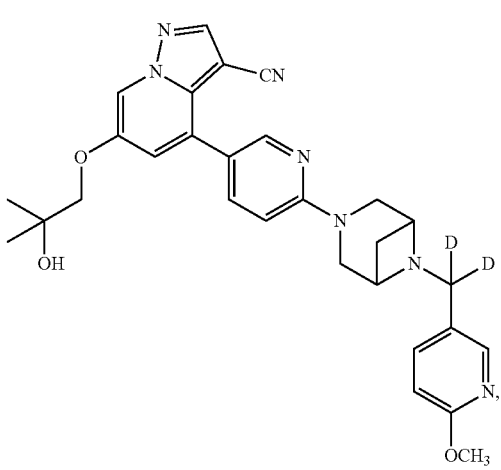
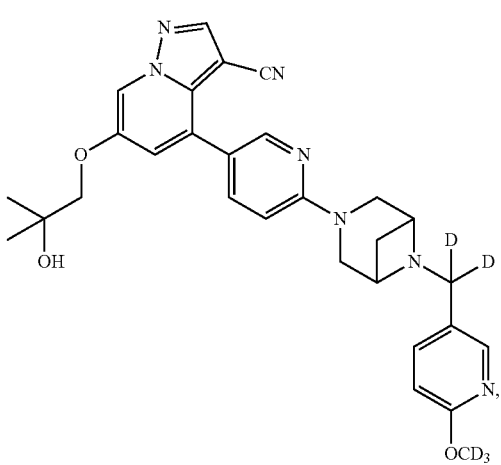
46
-continued
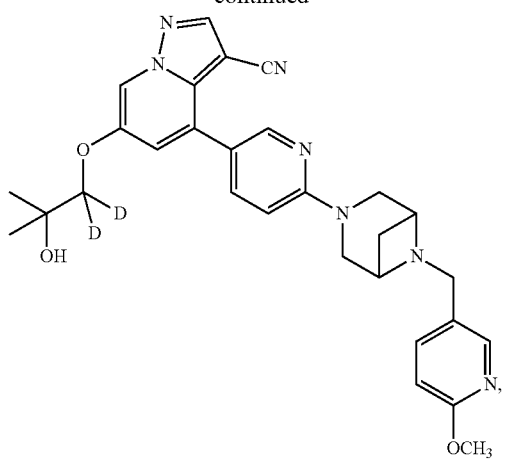
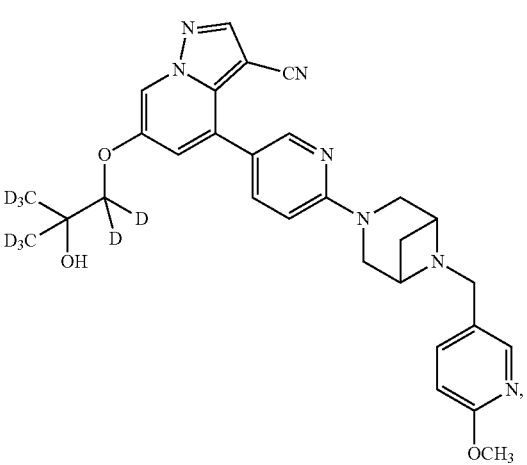

47
-continued
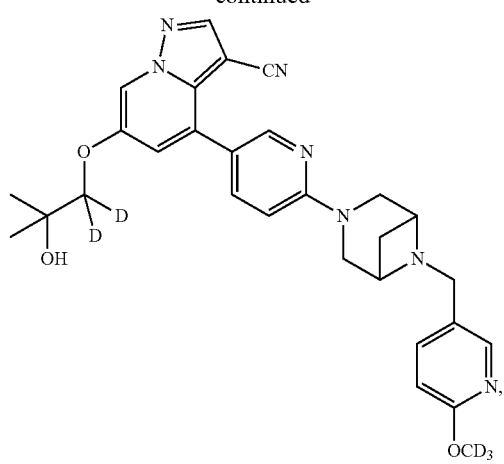
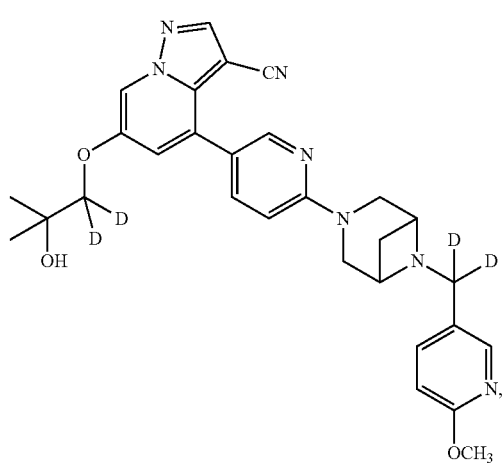
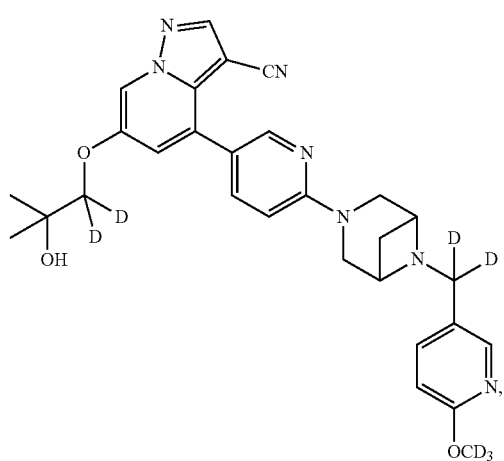
48
-continued
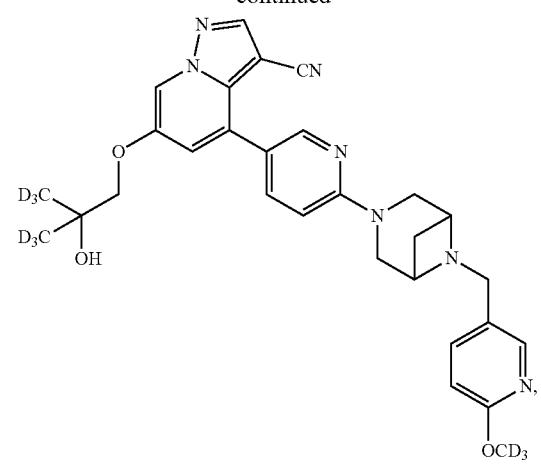
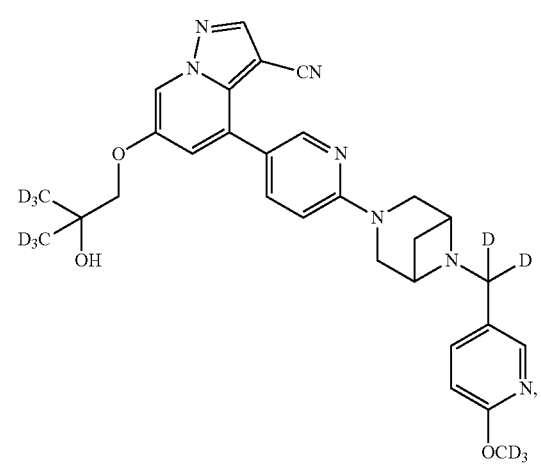

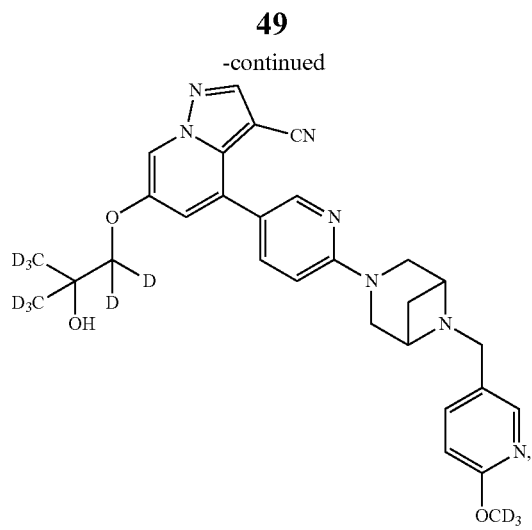

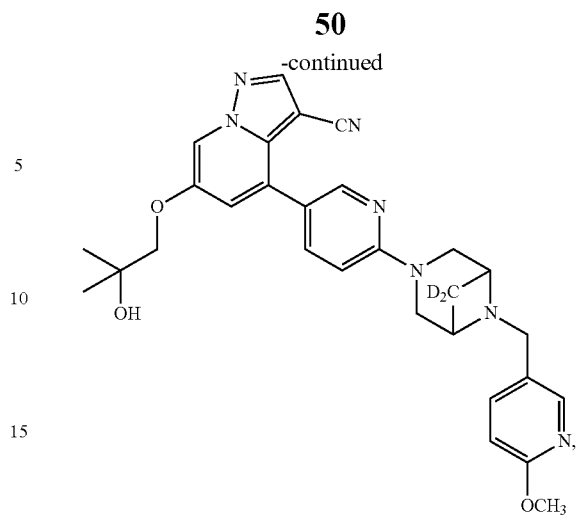

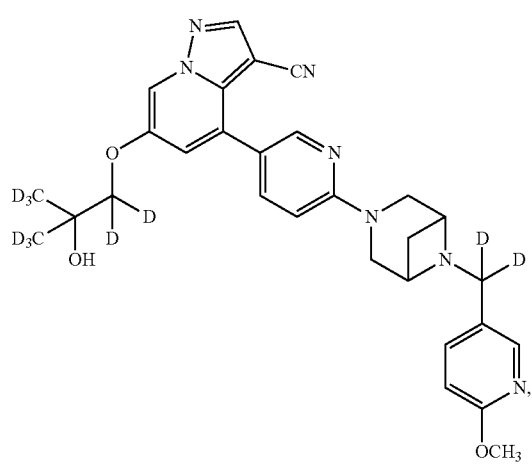

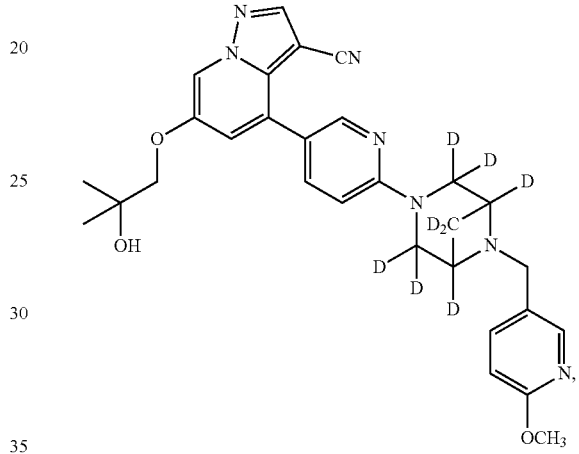

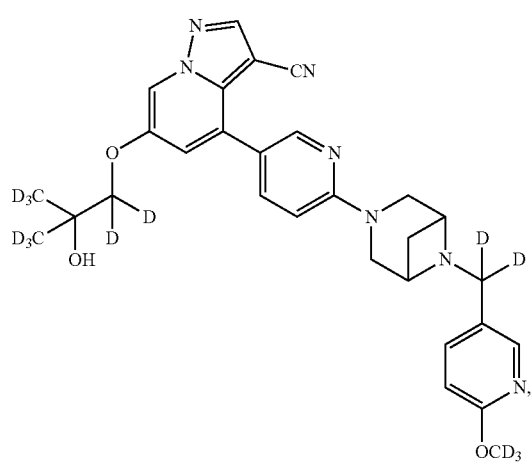

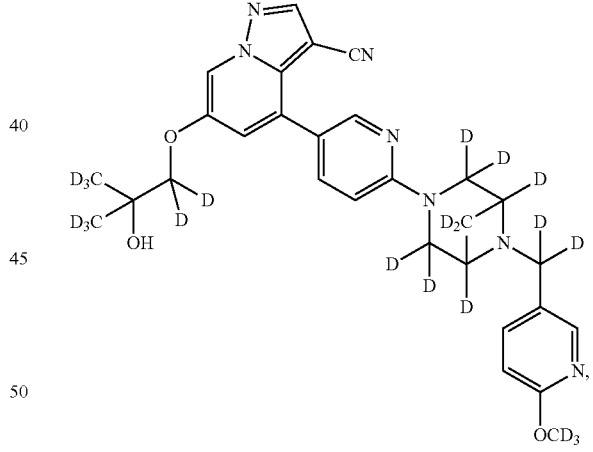

The compounds of the present disclosure may include one or more asymmetric centers, and therefore may exist in a variety of stereoisomeric forms, for example, enantiomeric and/or diastereomeric forms. For example, the compounds of the present disclosure may be individual enantiomers, diastereomers or geometric isomers (e.g., cis and trans isomers), or may be in the form of a mixture of stereoisomers, including racemate mixtures and mixtures rich in one or more stereoisomers. The isomers can be separated from the mixture by methods known to those skilled in the art, and the methods include: Chiral high pressure liquid chromatography (HPLC) and formation and crystallization of chiral salts; or the preferred isomers can be prepared by asymmetric synthesis.

Those skilled in the art will appreciate that organic compounds can form complexes with solvents that react in or precipitate or crystallize from the solvent. These complexes are referred to as "solvates." When the solvent is water, the complex is referred to as a "hydrate." The present disclosure encompasses all solvates of the compounds disclosed herein.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5 $H_2O$)) and polyhydrates (x is a number greater than 1, for example, dihydrates (R·2 $H_2O$) and hexahydrates (R·6 $H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

Also disclosed herein are isotopically labeled compounds, which are equivalent to those described as the compounds disclosed herein, but one or more atoms are replaced by atoms having an atom mass or mass number that are different from that of atoms that are common in nature. Examples of isotopes that can be listed in compounds disclosed herein include hydrogen, carbon, nitrogen, oxygen, phosphorus, sulfur, fluorine and chlorine isotopes, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. A compound disclosed herein containing the above isotope and/or other isotope of other atoms, a prodrug thereof, or a pharmaceutically acceptable salt of said compound or prodrug are all within the scope disclosed herein. Certain isotopically labeled compounds disclosed herein, such as those incorporating radioisotopes (e.g., $^3H$ and $^{14}C$), can be used in the tissue distribution experiments of drugs and/or substrates. Tritium, i.e., $^3H$, and carbon-14, i.e., $^{14}C$, are particularly preferred, because they are easier to be prepared and detected. In addition, substitution with heavier isotopes such as deuterium, i.e., $^2H$, may provide therapeutic benefits due to the higher metabolic stability, for example, increased half-life in vivo or reduced dosage, and thus priority may be given in some cases. Isotopically-labeled compounds of formula (I) disclosed herein and prodrugs thereof can be prepared using the following schemes and/or the procedures disclosed in the examples and preparation examples by replacing the non-isotopic reagents with readily available isotopically labeled reagents.

In addition, a prodrug is also included within the context disclosed herein. The term "prodrug" as used herein refers to a compound, which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each of which is incorporated herein by reference.

A prodrug is any covalently bonded compound disclosed herein which, when administered to a patient, releases the parent compound in vivo. A prodrug is typically prepared by modifying a functional group in such a way that the modification can be cleaved either by routine manipulation or decompose in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, the acetate/acetamide, formate/formamide and benzoate/benzamide derivatives of the hydroxyl, mercapto and amino functional groups of the compound of formula (I). Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those, which readily decompose in a human body to release a parent acid or its salt.

Method of Preparing the Compound Disclosed Herein

The compounds disclosed herein, including their salts, can be prepared using known organic synthetic techniques and can be synthesized according to any of various possible synthetic routes, such as those in the schemes below. The reaction for preparing compounds disclosed herein can be carried out in a suitable solvent, which can be easily selected by those skilled in the art of organic synthesis. The suitable solvent can be substantially unreactive with starting materials (reactants), intermediates or products at the temperature at which the reaction is carried out (for example, at temperatures ranging from the freezing temperature to boiling temperature of the solvent). A given reaction can be carried out in one solvent or a mixture of more than one solvent. The skilled person can select the solvent for the particular reaction step depending on the particular reaction step.

The preparation of the compounds disclosed herein may involve protection and deprotection of different chemical groups. One skilled in the art can readily determine the need for protection and deprotection and the choice of appropriate protective groups. The chemical properties of protective groups can be found, for example, in Wuts and Greene, Protective Groups in Organic Synthesis, 4th Ed., John Wiley & Sons: New Jersey, (2006), which is incorporated herein by reference in its entirety.

The compound of the present disclosure can be prepared as an individual stereoisomer thereof by reacting a racemic mixture of the compound with an optically active resolving agent to form a pair of diastereomeric compounds, separating the diastereomers, and recovering the optically pure enantiomer. The resolution of enantiomers can be carried out using a diastereomeric derivative of the compound disclosed herein, or alternatively, the dissociable complexes (for example, crystalline diastereomeric salts). Diastereomers have significantly different physical properties (for example, melting point, boiling point, solubility, reactivity, etc.), and can be easily separated by taking advantage of these dissimilarities. Diastereomers can be separated by chromatography, or alternatively by separation/resolution techniques based on differences in solubility. The optically pure enantiomer is then recovered, along with the resolving reagent, by any practical means that would not result in racemization. A more detailed description of the techniques applicable to the resolution of a racemic mixture to obtain stereoisomers of a compound can be found in Jean Jacques, Andre Collet, Samuel H. Wilen, "Enantiomers, Racemates and Resolutions", John Wiley And Sons, Inc., 1981.

The reaction can be monitored according to any suitable method known in the art. For example, product formation can be monitored by spectroscopic means (such as nuclear magnetic resonance (NMR) spectroscopy (e.g., $^1$H or $^{13}$C), infrared (IR) spectroscopy, spectrophotometry (e.g., UV-visible), mass spectrometry (MS)) or by chromatographic methods (such as high performance liquid chromatography (HPLC) or thin layer chromatography (TLC)).

Pharmaceutical Compositions, Formulations and Kits

In another aspect, provided herein is a pharmaceutical composition comprising the compound disclosed herein (also referred to as "active component") and pharmaceutically acceptable excipient(s). In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The "pharmaceutically acceptable excipient" for use in the present disclosure refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The present disclosure also includes a kit (e.g., pharmaceutical packs). The kit provided may include compounds disclosed herein, other therapeutic agents, and first and second containers containing the compounds disclosed herein and other therapeutic agents (e.g., vials, ampoules, bottles, syringes, and/or dispersible packages or other suitable containers). In some embodiments, the kit provided can also optionally include a third container containing a pharmaceutically acceptable excipient for diluting or suspending compounds disclosed herein and/or other therapeutic agents. In some embodiments, the compounds disclosed herein and other therapeutic agents provided in a first container and a second container are combined to form a unit dosage form.

The pharmaceutical composition provided herein can be administered by a variety of routes including, but not limited to, oral administration, parenteral administration, inhalation administration, topical administration, rectal administration, nasal administration, buccal cavity administration, vaginal administration, administration by implant or other means of administration. For example, the parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the condition disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to the administration of a compound or pharmaceutical composition thereof over an extended period of time, for example, over 3 months, 6 months, 1 year, 2 years, 3 years, 5 years, etc., or may be continued indefinitely, for example, for the rest of the subject's life. In some embodiments, the chronic administration is intended to provide a constant level of the compound in the blood, e.g., within the therapeutic window over the extended period of time.

The pharmaceutical compositions disclosed herein may be further delivered using a variety of dosing methods. For example, in some embodiments, the pharmaceutical composition may be given as a bolus, e.g., in order to rapidly raise the concentration of the compound in the blood to an effective level. The placement of the bolus dose depends on the systemic levels of the active ingredient desired, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1% to about 50% by weight or alternatively from about 1% to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 mg/kg to about 20 mg/kg of the compound disclosed herein, with preferred doses each providing from about 0.1 mg/kg to about 10 mg/kg, and especially about 1 mg/kg to about 5 mg/kg.

Transdermal doses are generally selected to provide similar or lower blood levels than are achieved using injection doses, generally in an amount ranging from about 0.01% to about 20% by weight, alternatively from about 0.1% to about 20% by weight, alternatively from about 0.1% to about 10% by weight, or yet alternatively from about 0.5% to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As mentioned before, the active compound in such compositions is typically a minor component, often being from about 0.05% to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the stable dermal penetration of the active ingredients or formulation. All such known transdermal formulations and ingredients are included within the scope provided herein.

The compounds disclosed herein can also be administered by a transdermal device. Accordingly, transdermal administration can be accomplished using a reservoir or a patch in porous membrane type or with various solid matrixes.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds disclosed herein can also be administered in sustained release forms or from sustained release drug delivery systems. A description of representative sustained release materials can be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are $\alpha$-, $\beta$- and $\gamma$-cyclodextrins consisting of 6, 7 and 8 $\alpha$-1,4-linked glucose units, respectively, optionally comprising one or more substituents on the linked sugar moieties, which include, but are not limited to, methylated, hydroxyalkylated, acylated, and sulfoalkylether substitution. In some embodiments, the cyclodextrin is a sulfoalkyl ether $\beta$-cyclodextrin, e.g., sulfobutyl ether $\beta$-cyclodextrin, also known as Captisol. See, e.g., U.S. Pat. No. 5,376,645. In some embodiments, the formulation comprises hexapropyl-$\beta$-cyclodextrin (e.g., 10% to 50% in water).

Indications

The compound of the present disclosure is inhibitor of RET kinase, and can be used to treat diseases and disorders treatable with RET kinase inhibitors, for example RET-associated diseases and disorders, such as proliferative disorders (such as cancer, including blood cancers and solid tumors), and gastrointestinal diseases (IBS).

The term "RET-associated disease or disorder" as used herein refers to diseases or disorders associated with or having a dysregulation of a RET gene, a RET kinase (also called herein RET kinase protein or RET kinase), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein or RET kinase), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a RET gene translocation that results in the expression of a fusion protein, a deletion in a RET gene that results in the expression of a RET protein that includes a deletion of at least one amino acid as compared to the wild-type RET protein, or a mutation in a RET gene that results in the expression of a RET protein with one or more point mutations, or an alternative spliced version of a RET mRNA that results in a RET protein that results in the deletion of at least one amino acid in the RET protein as compared to the wild-type RET protein), or a RET gene amplification that results in overexpression of a RET protein or an autocrine activity resulting from the overexpression of a RET gene a cell, that results in a pathogenic increase in the activity of a kinase domain of a RET protein (e.g., a constitutively active kinase domain of a RET protein) in a cell. As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET kinase, or the expression or activity or level of any of the same, can be a result of a gene translation of one RET gene with another RET gene. Non-limiting examples of fusion proteins and non-limiting examples of RET kinase protein point mutations/insertions are described herein. Additional examples of RET kinase protein point mutations are RET inhibitor resistance mutations. Non-limiting examples of RET inhibitor resistance mutations are described herein.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

In some embodiments, a hematological cancer (e.g., hematological cancers that are RET-associated cancers) is selected from the group consisting of leukemias, lymphomas (non-Hodgkin's lymphoma), Hodgkin's lymphoma, and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

The compound of the present disclosure and pharmaceutically acceptable salts and solvates thereof, or the pharmaceutical composition containing the compound of the present disclosure and pharmaceutically acceptable salts and solvates thereof can also be used to treat RET-associated cancers.

Accordingly, also provided herein is a method for treating a patient diagnosed with or identified as having a RET-associated cancer, e.g., any of the exemplary RET-associated cancers disclosed herein, comprising administering to the patient a therapeutically effective amount of a compound of the present disclosure or a pharmaceutically acceptable salt or solvate thereof, or a pharmaceutical composition thereof as defined herein.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include translocations involving the RET kinase domain, mutations can include mutations involving the RET ligand-binding site, and amplification can be of a RET gene. Other dysregulations can include RET mRNA splice variants and RET autocrine/paracrine signaling, which can also contribute to tumorigenesis.

In some embodiments, the dysregulation in a RET gene, a RET kinase, or expression or activity or level of any of the same, includes one or more chromosomal translocations or inversions that result in the fusion of the RET gene. In some embodiments, the dysregulation in a RET gene, a RET kinase, or expression or activity or level of any of the same, is the result of genetic translocation, wherein the protein expressed therein is a fusion protein containing residues from a non-RET chaperone protein and includes a minimal functional RET kinase domain.

In some embodiments, non-limiting examples of RET fusion proteins are BCR-RET, CLIP1-RET, KIF5B-RET, CCDC6-RET, NCOA4-RET, TRIM33-RET, ERC1-RET, ELKS-RET, RET-ELKS, FGFR1OP-RET, RET-MBD1, RET-RAB61P2, RET-PCM1, RET-PPKAR1A, RET-TRIM24, RET-RFG9, RFP-RET, RET-GOLGA5, HOOKS-RET, KTN1-RET, TRIM27-RET, AKAP13-RET, FKBP15-RET, SPECC1L-RET, TBL1XR1/RET, CEP55-RET, CUX1-RET, KIAA1468-RET, PPKAR1A-RET, RFG8/RET, RET/RFG8, H4-RET, ACBD5-RET, PTCex9-RET, MYH13-RET, PIBF1-RET, KIAA1217-RET or MPRIP-RET.

TABLE 1

| Exemplary RET fusion partners and cancers [1] | |
| --- | --- |
| Fusion partner | Non-limiting exemplary RET-associated cancers |
| BCR | Chronic myelomonocytic leukemia(CMML) |
| CLIP1 | Adenocarcinoma |
| KIF5B | NSCLC, ovarian cancer, spitzoid neoplasm, lung adenocarcinoma, adenosquamous carcinoma |
| CCDC6(also known as PTC1, DI0S170 or H4) | NSCLC, colon cancer, papillary thyroid cancer, adenocarcinoma, lung adenocarcinoma, metastatic colorectal cancer, adenosquamous carcinoma |
| PTClex9 | Metastatic papillary thyroid cancer |
| NCOA4 | Papillary thyroid cancer, NSCLC, colon cancer, salivary gland cancer, metastatic colorectal cancer, lung adenocarcinoma, adenosquamous carcinoma, diffuse sclerosis variant of papillary thyroid carcinoma |
| TRIM33(also known as PTC7 and RFG7) | NSCLC, papillary thyroid cancer |
| ERC1(also known as ELKS) | Papillary thyroid cancer, breast cancer |
| FGFR1OP | CMML, Primary myelofibrosis with secondary acute myeloid leukemia |
| MBD1(also known as PCM1) | Papillary thyroid cancer |
| RAB61P2 | Papillary thyroid cancer |
| PRKAR1A(also known as PTC2) | Papillary thyroid cancer |
| TRIM24(also known as PTC6) | Papillary thyroid cancer |
| KTN1(also known as PTC8) | Papillary thyroid cancer |
| GOLGA5(also known as PTC5) | Papillary thyroid cancer, Spitzoid neoplasm |
| HOOK3 | Papillary thyroid cancer |
| KIAA1468(also known as PTC9 and RFG9) | Papillary thyroid cancer, lung adenocarcinoma |
| TRIM27(also known as RFP) | Papillary thyroid cancer |
| AKAP13 | Papillary thyroid cancer |
| FKBP15 | Papillary thyroid cancer |
| SPECC1L | Papillary thyroid cancer, thyroid cancer |
| TBL1XR1 | Papillary thyroid cancer, thyroid cancer |
| CEP55 | Diffuse gastric cancer |
| CUX1 | Lung adenocarcinoma |
| ACBD5 | Papillary thyroid cancer |
| MYH13 | Papillary thyroid cancer |
| Uncharacterized | Inflammatory myofibroblastoma |
| PIBF1 | Papillary thyroid cancer, lung adenocarcinoma, NSCLC |
| KIAA1217 | NSCLC |
| MPRIP | NSCLC |

[1] International Public Number WO2017/011776A1.

In some embodiments, the dysregulation in a RET gene, a RET kinase, or expression or activity or level of any of the same, includes one or more deletions (for example, deletion of amino acid at position 4), insertions, or point mutations in RET kinase. In some embodiments, the dysregulation in a RET gene, a RET kinase, or expression or activity or level of any of the same, including the deletion of one or more residues of RET kinase, resulting in the constitutive activity of the RET kinase domain. In some embodiments, the dysregulation in a RET gene, a RET kinase, or expression or activity or level of any of the same, includes at least one point mutation in the RET gene, which results in the production of RET kinase with one or more amino acid substitutions compared to wild-type RET kinase. In some embodiments, exemplary RET point mutations include but are not limited to: S32L, D34S, L40P, P64L, R67H, R114H, V145G, V292M, G321R, R330Q, T338I, R360W, F393L, A510V, E511K, C515S, C531R, G533C, G533S, G550E, V591I, G593E, I602V, R600Q, K603Q, K603E, Y606C, C609Y, C609S, C609G, C609R, C609F, C609W, C611R, C611S, C611G, C611Y, C611F, C611W, C618S, C618Y, C618R, C618Y, C618G, C618F, C618W, F619F, C620S, C620W, C620R, C620G, C620L, C620Y, C620F, E623K, D624N, C630A, C630R, C630S, C630Y, C630F, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, S686N, G691S, R694Q, M700L, V706M, V706A, E713K, G736R, G748C, A750P, S765P, P766S, P766M, E768Q, E768D, L769L, R770Q, D771N, N777S, V778I, Q781R, L790F, Y791F, V804L, V804M, V804E, E805K, Y806E, Y806F, Y806S, Y806G, Y806C, E818K, S819I, G823E, Y826M, R833C, P841L, P841P, E843D, R844W, R844Q, R844L, M848T, I852M, A866W, R873W, A876V, L881V, A883F, A883S, A883T, E884K, R886W, S891A, R897Q, D898V, E901K, S904F, S904C, K907E, K907M, R908K, G911D, R912P, R912Q, M918T, M918V, M918L, A919V, E921K, S922P, S922Y, T930M, F961L, R972G, R982C, M1009V, D1017N, V1041G or M1064T.

In some embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to a compound of the present disclosure or a pharmaceutically acceptable salt or solvate thereof, as compared to a wildtype RET kinase or a RET kinase not including the same mutation. In such embodiments, a RET inhibitor resistance mutation can result in a RET kinase that has one or more of an increased Vmax, a decreased Km, and a decreased KD in the presence of a compound of the present disclosure or a pharmaceutically acceptable salt or solvate thereof, as compared to a wildtype RET kinase or a RET kinase not having the same mutation in the presence of the same compound of the present disclosure or a pharmaceutically acceptable salt or solvate thereof.

Examples of RET inhibitor resistance mutations can, e.g., include point mutations, insertions, or deletions in and near the ATP binding site in the tertiary structure of RET kinase, including but not limited to the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that may be changed (and are RET inhibitor resistance mutations) include but are not limited to the human wildtype RET protein sequence (e.g., SEQ ID NO: 1). RET inhibitor resistance mutations include but are not limited to amino acid position 804 (V804M, V804L, V804E), amino acid position 804/805 (V804M/E805K), amino acid position 806 (Y806C, Y806E). Changes to these residues may include single or multiple amino acid changes, insertions within or flanking the sequences, and deletions within or flanking the sequences.

In some embodiments, compounds of the present disclosure and pharmaceutically acceptable salts and solvates are useful in treating patients that develop cancers with RET inhibitor resistance mutations (that result in an increased resistance to a RET inhibitor that is not a compound of the present disclosure or a pharmaceutically acceptable salt or solvate thereof, e.g., a substitution at amino acid position 804, e.g., V804M, V804L, or V804E) by either dosing in combination or as a follow-up therapy to existing drug treatments (e.g., other RET kinase inhibitors that are not a compound of the present disclosure or a pharmaceutically acceptable salt or solvate thereof). Exemplary RET kinase inhibitors (e.g., other RET kinase inhibitors that are not a compound of the present disclosure or a pharmaceutically acceptable salt or solvate thereof) are described herein. In some embodiments, a RET kinase inhibitor can be selected from the group consisting of cabozantinib, vandetanib, alectinib, sorafenib, levatinib, ponatinib, dovitinib, sunitinib, foretinib, BLU667, and BLU6864.

In some embodiments, compounds of the present disclosure and pharmaceutically acceptable salts and solvates would be useful for treating a cancer that has been identified as having one or more RET inhibitor resistance mutations (that result in an increased resistance to a RET inhibitor that is not a compound of the present disclosure or a pharmaceutically acceptable salt or solvate thereof, e.g., a substitution at amino acid position 804, e.g., V804M, V804L, or V804E).

Accordingly, provided herein are methods for treating a patient diagnosed with (or identified as having) a cancer (e.g., a RET-associated cancer) (e.g., a RET-associated cancer that includes one or more RET inhibitor resistance mutations) that include administering to the patient a therapeutically effective amount of a compound of the present disclosure or a pharmaceutically acceptable salt or solvate thereof. Also provided herein are methods for treating a patient identified or diagnosed as having a RET-associated cancer (e.g., a patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient) (e.g., any of the RET-associated cancers described herein or known in the art) (e.g., a RET-associated cancer that includes one or more RET inhibitor resistance mutations) that include administering to the patient a therapeutically effective amount of a compound of the present disclosure or a pharmaceutically acceptable salt or solvate thereof or a pharmaceutical composition thereof.

Also provided is a compound of the present disclosure or a pharmaceutically acceptable salt or solvate thereof, for use in the treatment of a cancer (e.g., a RET-associated cancer, e.g., a RET-associated cancer having one or more RET inhibitor resistance mutations) in a patient in need thereof or a patient identified or diagnosed as having a RET-associated cancer (e.g., a patient that has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the sample) (e.g., any of the RET-associated cancers described herein or known in the art). Also provided is the use of a compound of the present disclosure or a pharmaceutically acceptable salt or solvate thereof for the manufacture of a medicament for treating a cancer (e.g., a RET-associated cancer, e.g., a RET-associated cancer having one or more RET inhibitor resistance mutations) in a patient identified or diagnosed as having a RET-associated cancer (e.g., a patient that has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient) (e.g., any of the RET-associated cancers described herein or known in the art).

Also provided herein is a method of treating a subject. The method includes performing an assay on a sample obtained from the subject to determine whether the subject has dysregulation of a RET gene, a RET protein, or expression or level of any of the same (e.g., one or more RET inhibitor resistance mutations). The method also includes administering to a subject determined to have dysregulation of a RET gene, a RET protein, or expression or activity, or level of any of the same (e.g., one or more RET inhibitor resistance mutations) a therapeutically effective amount of a compound of General Formula (I) or a pharmaceutically acceptable salt or solvate thereof. In some embodiments, the RET fusion can be selected from a KIF5B-RET fusion and a CCDC6-RET fusion. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, and V804M. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., another RET inhibitor, e.g., a RET inhibitor that is not a compound of General Formula (I) or a pharmaceutically acceptable salt or solvate thereof, or a different RET inhibitor that is a compound of the present disclosure or a pharmaceutically acceptable salt or solvate thereof).

Combination Therapy

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds of the present disclosure therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of the present disclosure (or a pharmaceutically acceptable salt or solvate thereof) is administered in combination with a therapeutically effective amount of at least one additional therapeutic agent selected from one or more additional therapies or therapeutic (e.g., chemotherapeutic) agents. Non-limiting examples of additional therapeutic agents include: other RET-targeted therapeutic agents (i.e. other RET kinase inhibitors; RET inhibitors that are not a compound of the present disclosure or a pharmaceutically acceptable salt or solvate thereof), receptor tyrosine kinase-targeted therapeutic agents, signal transduction pathway inhibitors, checkpoint inhibitors, modulators of the apoptosis pathway (e.g. Obataclax); cytotoxic chemotherapeutics, angiogenesis-targeted therapies, immune-targeted agents, and radiotherapy.

In some embodiments, the other RET-targeted therapeutic is a multikinase inhibitor exhibiting RET inhibition activity. In some embodiments, the other RET-targeted therapeutic inhibitor is selective for a RET kinase. Exemplary RET-targeted therapeutics can exhibit inhibition activity (IC$_{50}$) against a RET kinase of less than about 1000 nM, less than about 500 nM, less than about 200 nM, less than about 100 nM, less than about 50 nM, less than about 25 nM, less than about 10 nM, or less than about 1 nM.

Non-limiting examples of RET-targeted therapeutic agents include alectinib, apatinib, cabozantinib (XL-184), dovitinib, lenvatinib, motesanib, nintedanib, ponatinib, regorafenib, sitravatinib, sunitinib, sorafenib, vatalanib, vandetanib, AUY-922 (5-(2,4-Dihydroxy-5-isopropyl-phenyl)-N-ethyl-4-[4-(morpholinomethyl)phenyl]isoxazole-3-carboxamide), BLU6864, BLU-667, DCC-2157, NVP-AST487 (1-[4-[(4-ethylpiperazin-1-yl)methyl]-3-(trifluoromethyl)phenyl]-3-[4-[6-(methylamino)pyrimidin-4-yl]oxyphenyl]urea), PZ-1, RPI-1 (1,3-dihydro-5,6-dimethoxy-3-[(4-hydroxyphenyl)methylene]-H-indol-2-one), RXDX-105 (1-(3-((6,7-dimethoxyquinazolin-4-yl)oxy)phenyl)-3-(5-(1,1,1-trifluoro-2-methylpropan-2-yl)isoxazol-3-yl)urea), SPP86 (1-Isopropyl-3-(phenylethynyl)-1H-pyrazolo[3,4-d]pyrimidin-4-amine), and TG101209 (N-(1,1-dimethylethyl)-3-[[5-methyl-2-[[4-(4-methyl-1-piperazinyl)phenyl]amino]-4-pyrimidinyl]amino]-benzenesulfonamide).

Accordingly, also provided herein is a method of treating cancer, comprising administering to a patient in need thereof a pharmaceutical combination for treating cancer which comprises (a) a compound of the present disclosure or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of the present disclosure or a pharmaceutically acceptable salt or solvate thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same. These additional therapeutic agents may be administered with one or more doses of the compound of General Formula (I), or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer (e.g., a RET-associated cancer (e.g., a RET-associated cancer having one or more RET inhibitor resistance mutations)) in a patient in need thereof, which comprises (a) a compound of the present disclosure or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of the present disclosure or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of the present disclosure or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of the present disclosure or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients.

Accordingly, also provided herein is a method of treating a cancer (e.g., a RET-associated cancer (e.g., a RET-associated cancer having one or more RET inhibitor resistance mutations)), comprising administering to a patient in need thereof a pharmaceutical combination for treating cancer which comprises (a) a compound of the present disclosure or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of the present disclosure or pharmaceutically acceptable salt or solvate thereof and the additional therapeutic agent are together effective in treating the cancer. In one embodiment, the compound of the present disclosure or pharmaceutically acceptable salt or solvate thereof, and the additional therapeutic agent are administered simultaneously as separate dosages. In one embodiment, the compound of the present disclosure or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of the present disclosure or pharmaceutically acceptable salt or solvate thereof, and the additional therapeutic agent are administered simultaneously as a combined dosage.

Also provided herein is a method of treating a disease or disorder mediated by RET (e.g., dysregulation of RET gene, a RET kinase, or expression or activity or level of any of the same, e.g., one or more RET inhibitor resistance mutations) in a patient in need of such treatment, the method comprising administering to the patient a therapeutically effective amount of a compound of the present disclosure or a pharmaceutically acceptable salt or solvate thereof or a pharmaceutical composition thereof. A disease or disorder mediated by RET (e.g., dysregulation of RET gene, a RET kinase, or expression or activity or level of any of the same, e.g., one or more RET inhibitor resistance mutations) can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein.

EXAMPLES

The present disclosure is further illustrated below in conjunction with specific examples. It is to be understood that the examples are used to illustrate the present disclosure, and not intended to limit the scope of present disclosure. In the following examples, the experimental methods wherein the particular conditions are not specified are usually in accordance with conventional conditions or according to the conditions recommended by the manufacturer. Parts and percentages are parts by weight and percentage by weight unless otherwise stated.

The abbreviations used herein are shown in Table 2 below.

TABLE 2

| | |
|---|---|
| APCI | Atmospheric pressure chemical ionization |
| Boc | Tert-butoxycarbonyl |
| MsCl | Methanesulfonyl chloride |
| $B_2(pin)_2$ | Bis(pinacolato)diboron |
| X-Phos | 2-Dicyclohexylphosphino-2',4',6'-triisopropylbiphenyl |
| $Pd_2(dba)_3$ | Tris(dibenzylideneacetone)dipalladium |
| $PdCl_2(dppf)DCM$ | [1,1'-Bis(diphenylphosphino)ferrocene]dichloro palladium dichloromethane complex |
| $Pd(PPh_3)_4$ | Tetrakis(triphenylphosphine)palladium |

TABLE 2-continued

| | |
|---|---|
| $NaBH_4$ | Sodium borohydride |
| LiAlD4 | Lithium aluminium deuteride |
| NaH | Sodium hydride |
| KOAc | Potassium acetate |
| $Cs_2CO_3$ | Cesium carbonate |
| $K_2CO_3$ | Potassium carbonate |
| $Na_2CO_3$ | Sodium carbonate |
| DIPEA | N,N-diisopropylethylamine |
| TEA | Triethylamine |
| TFA | trifluoroacetic acid |
| HCl | hydrochloric acid |
| THF | tetrahydrofuran |
| DCM | dichloromethane |
| MTBE | Methyl tert-butyl ether |
| DCE | 1,2-Dichloroethane |
| DMF | N,N-dimethylformamide |
| DMA | N,N-dimethylacetamide |
| Dioxane | 1,4-Dioxane |
| DME | Ethylene glycol dimethyl ether |
| EtOAc | Ethyl acetate |
| PE | Petroleum ether |
| $CDCl_3$ | Deuterated chloroform |
| DMSO | Dimethylsulphoxide |
| MeOH | Methanol |

Intermediate P1: 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile

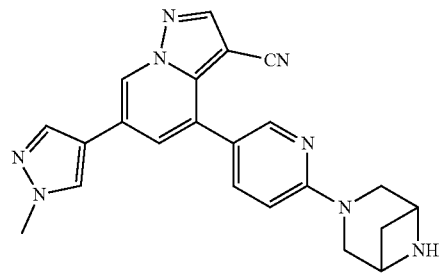

P1

The following route was used for the synthesis:

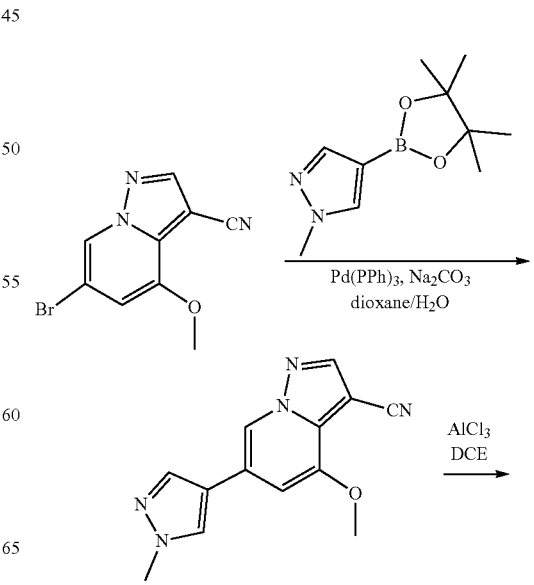

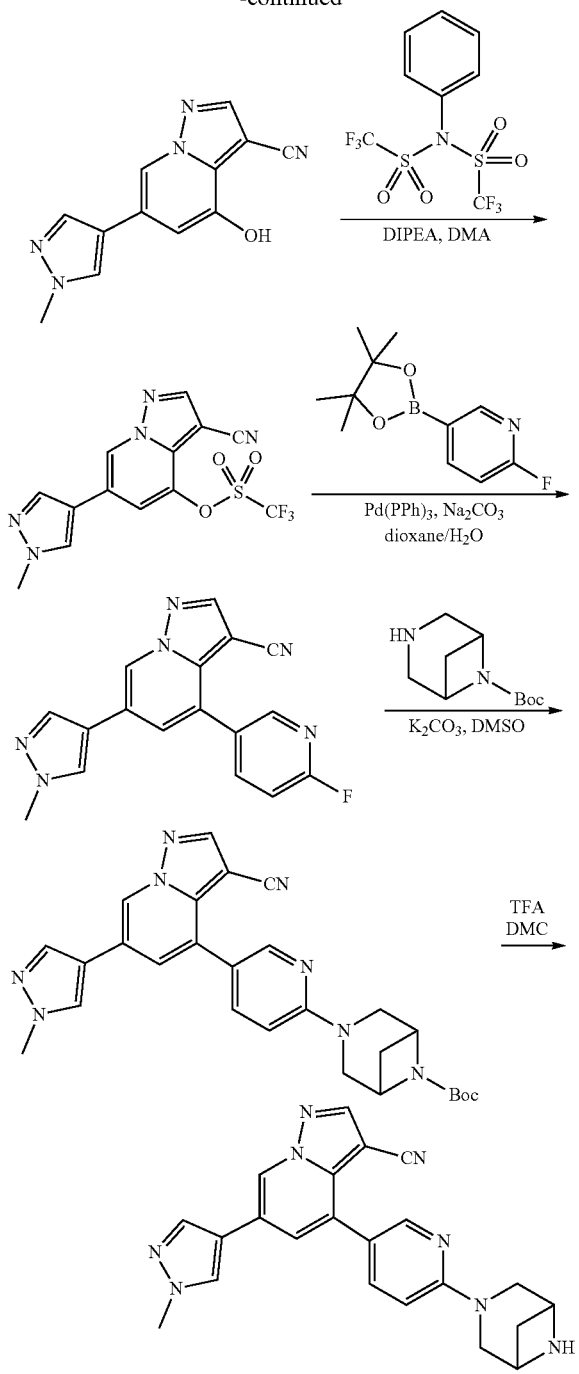

Step 1 The Synthesis of 4-methoxy-6-(1-methyl-1H-pyrazol-4-yl)pyrazolo[1,5-a]pyridine-3-carbonitrile Under nitrogen protection, Pd(PPh₃)₄ (692 mg) was added to 6-bromo-4-methoxypyrazolo[1,5-a]pyridine-3-nitrile (2.5 g), 1-methyl-4-(4,4,5,5-tetramethyl-1,3,2-dioxaborolan-2-yl)-1H-pyrazole (2.49 g) and sodium carbonate (3.15 g) in mixed solvent of dioxane (33 mL) and water (15 mL), and the reaction was stirred overnight at 80° C. under nitrogen protection. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 2.3 g light yellow solid. LC-MS (APCI): m/z=254.1 (M+1)⁺, ¹H NMR (400 MHz, DMSO) δ 8.87 (d, J=1.0 Hz, 1H), 8.54 (s, 1H), 8.37 (s, 1H), 8.10 (d, J=0.6 Hz, 1H), 7.28 (d, J=0.8 Hz, 1H), 4.07 (s, 3H), 3.89 (s, 3H).

Step 2 4-hydroxy-6-(1-methyl-1H-pyrazol-4-yl)pyrazolo[1,5-a]pyridine-3-carbonitrile At room temperature, aluminum trichloride (4.06 g) was added to 4-methoxy-6-(1-methyl-1H-pyrazol-4-yl)pyrazolo[1,5-a]pyridine-3-carbonitrile (2.3 g) in anhydrous DCE (44 mL), which was reacted overnight under reflux. After cooling to room temperature, the reaction system was diluted by adding DCE (25 mL), and the reaction was quenched by adding water (25 mL×2). The reaction was stirred at room temperature for 3 hrs. The solid was filtered, dried in vacuum at 40° C. to give 1.5 g light yellow solid. LC-MS (APCI): m/z=240.1 (M+1)⁺.

Step 3 The Synthesis of 3-cyano-6-(1-methyl-1H-pyrazol-4-yl)pyrazolo[1,5-a]pyridin-4-yl triflate N-Phenyl-bis(trifluoromethanesulfonimide) (2.46 g) was added to 4-hydroxy-6-(1-methyl-1H-pyrazol-4-yl)pyrazolo[1,5-a]pyridine-3-carbonitrile (1.5 g) and DIPEA (2.18 mL) in DMA (12.5 mL), and the reaction was stirred at room temperature for 2 hrs. The reaction was quenched by being added into water (150 mL), the solid was filtered, washed with water (20 mL×3). The solid was dissolved in DCM (150 mL), dried over anhydrous sodium sulfate, the filtrate was concentrated under reduced pressure, and the concentrate was purified by column chromatography (PE/EtOAc=50%) and concentrated to give 2.1 g earthy gray solid. ¹H NMR (300 MHz, CDCl₃) δ 8.66 (d, J=1.0 Hz, 1H), 8.29 (s, 1H), 7.78 (s, 1H), 7.71 (s, 1H), 7.56 (d, J=0.9 Hz, 1H), 4.01 (s, 3H).

Step 4 The Synthesis of 4-(6-fluoropyridin-3-yl)-6-(1-methyl-1H-pyrazol-4-yl)pyrazolo[1,5-a]pyridine-3-carbonitrile Under nitrogen protection, Pd(PPh₃)₄ (155.6 mg, 0.13 mmol) was added to 3-cyano-6-(1-methyl-1H-pyrazol-4-yl)pyrazolo[1,5-a]pyridine-4-yl triflate (1.00 g, 2.70 mmol), 2-fluoro-5-(4,4,5,5-tetramethyl-1,3,2-dioxaborolan-2-yl)pyridine (902 mg, 4.04 mmol) and sodium carbonate (707 mg, 6.73 mmol) in mixed solvent of dioxane (26 mL) and water (3.4 mL), and under nitrogen protection, the reaction was conducted at 90° C. in sealed tube overnight. The reaction was cooled to room temperature, added with water (25 mL), stirred thoroughly for 3 hrs. The solid was filtered, washed with water (10 mL×3) and cooled MTBE (5 mL×2), dried in vacuum to afford 740 mg light yellow solid, Yield: 87%. LC-MS (APCI): m/z=319.1 (M+1)⁺.

Step 5 The Synthesis of tert-butyl 3-(5-(3-cyano-6-(1-methyl-1H-pyrazol-4-yl)pyrazolo[1,5-a]pyridin-4-yl)pyridin-2-yl)-3,6-diazabicyclo[3.1.1]heptane-6-carboxylate At room temperature, K₂CO₃ (780 mg, 5.65 mmol) was added to 4-(6-fluoropyridin-3-yl)-6-(1-methyl-1H-pyrazol-4-yl)pyrazolo[1,5-a]pyridine-3-carbonitrile (600 mg, 1.88 mmol) and 6-(tert-butoxycarbonyl)-3,6-diazabicyclo[3.1.1]

heptane (374 mg, 1.88 mmol) in anhydrous DMSO (8 mL), and the reaction was stirred at 95° C. overnight. The reaction was cooled to room temperature, the reaction system was diluted by adding H₂O, and washed with EtOAc for 3 times. The organic layers were combined, washed with saturated brine for 2 times, dried over anhydrous sodium sulfate, filtered, concentrated under reduced pressure, and the concentrate was purified by column chromatography (PE/EtOAc=10%) to give 800 mg light yellow solid, Yield: 85.4%. LC-MS (APCI): m/z=497.2 (M+1)⁺.

Step 6 The Synthesis of 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile In an ice bath, TFA (10 mL) was added to a solution of tert-butyl 3-(5-(3-cyano-6-(1-methyl-1H-pyrazol-4-ylpyrazolo[1,5-a]pyridin-4-yl)pyridin-2-yl)-3,6-diazabicyclo[3.1.1]heptane-6-carboxylate (600 mg, 1.21 mmol) in DCM (10 mL), and the reaction was conducted at room temperature for 3 hrs. The reaction solution was concentrated under reduced pressure, adjusted to a basic pH with ammonia-methanol solution, concentrated under reduced pressure, and the concentrate was purified by column chromatography (DCM/MeOH=12%) to give 425 mg white solid. LC-MS (APCI): m/z=397.2 (M+1)⁺.

Intermediate P2: 4-(6-(3,6-diazabicyclo[3.1.1]heptan-3-yl)pyridin-3-yl)-6-(1-(methyl-d₃)-1H-pyrazol-4-yl)pyrazolo[1,5-a]pyridine-3-carbonitrile

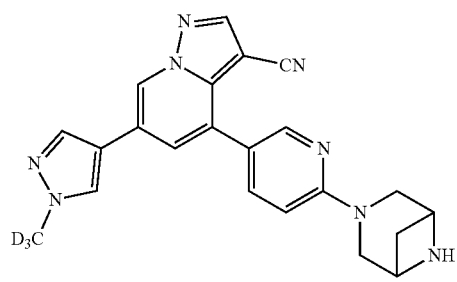

P2

The following route was used for the synthesis:

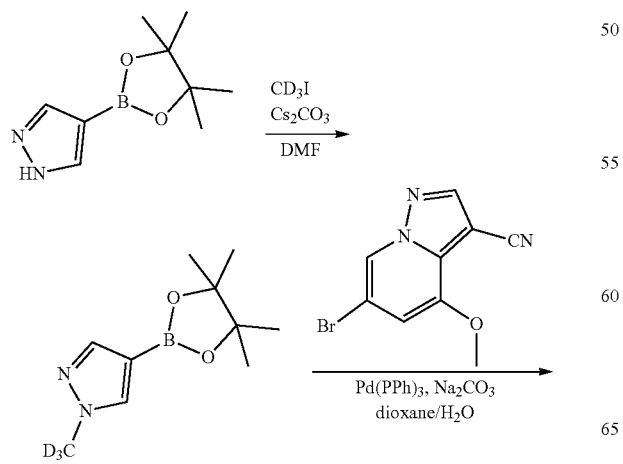

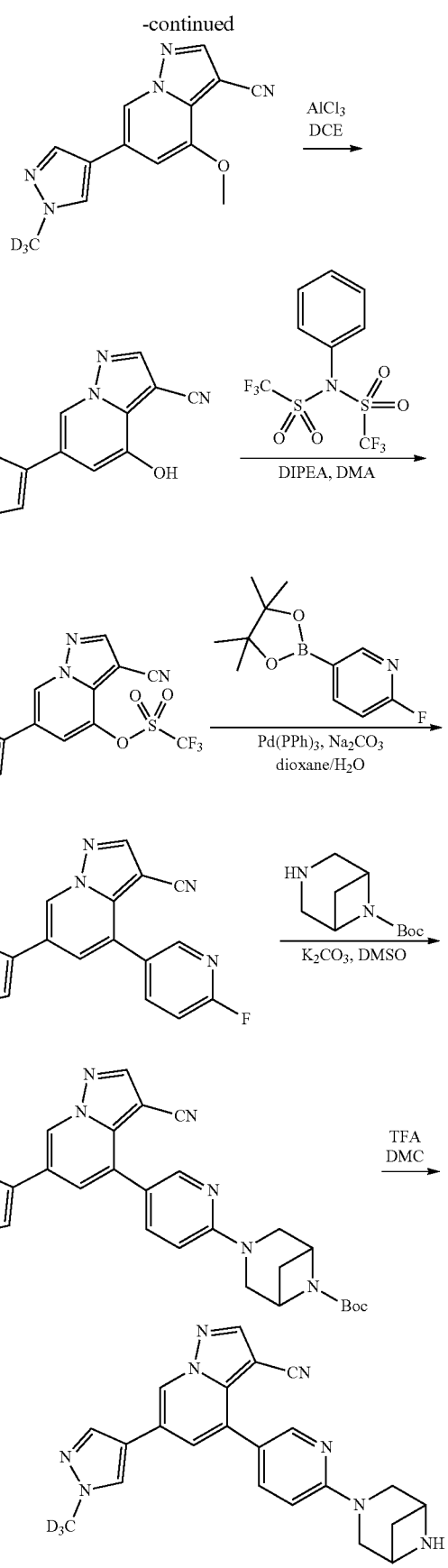

Step 1 The Synthesis of 1-(methyl-d₃)-4-(4,4,5,5-tetramethyl-1,3,2-dioxaborolan-2-yl)-1H-pyrazole At room temperature, deuterated methyl iodide (28.38 mmol, 1.77 mL) was added to 4-(4,4,5,5-tetramethyl-1,3,2-dioxaborolan-2-yl)-1H-pyrazole (5 g, 27.78 mmol) and cesium carbonate (10.11 g, 31.11 mmol) in anhydrous DMF (100 mL), and the reaction was stirred at room temperature for 3 hrs. The reaction was diluted with EtOAc (300 mL), washed with water (100 mL×3) and saturated brine (100 mL×3) respectively, the organic layer was dried over anhydrous sodium sulfate, filtered, and the filtrate was concentrated under reduced pressure to give 4.0 g light yellow solid, Yield: 68.22%. LC-MS (APCI): m/z=212.3 (M+1)⁺. ¹H NMR (500 MHz, CDCl₃): δ 7.76 (s, 1H), 7.64 (s, 1H), 1.31 (s, 12H).

Step 2 The Synthesis of 4-methoxy-6-(1-(methyl-d₃)-1H-pyrazol-4-yl)pyrazolo[1,5-a]pyridine-3-carbonitrile Under nitrogen protection, Pd(PPh₃)₄ (600 mg, 4.73 mmol) was added to 6-bromo-4-methoxypyrazolo[1,5-a]pyridine-3-carbonitrile (3.96 g, 15.78 mmol), 1-(methyl-d₃)-4-(4,4,5,5-tetramethyl-1,3,2-dioxaborolan-2-yl)-1H-pyrazole (4.00 g, 18.94 mmol) and sodium carbonate (5.00 g, 47.34 mmol) in mixed solvent of dioxane (52 mL) and water (22 mL), and the reaction was stirred overnight at 80° C. under nitrogen protection. The reaction was cooled to room temperature, stirred vigorously at room temperature for 2 hrs, the solid was filtered, washed with water (100 mL) and MTBE (15 mL×3) respectively, and dried in vacuum to afford 3.3 g light yellow solid. LC-MS (APCI): m/z=257.1 (M+1)⁺.

Step 3 The Synthesis of 4-hydroxy-6-(1-(methyl-d₃)-1H-pyrazol-4-yl)pyrazolo[1,5-a]pyridine-3-carbonitrile At room temperature, aluminum trichloride (5.12 g) was added to 4-methoxy-6-(1-(methyl-d₃)-1H-pyrazol-4-yl)pyrazolo[1,5-a]pyridine-3-carbonitrile (3.3 g) in anhydrous DCE (66 mL), and the reaction was refluxed overnight. The reaction was cooled to room temperature, diluted by adding DCE (60 mL), and the reaction was quenched by adding water (25 mL×2). The reaction was stirred at room temperature for 3 hrs. The solid was filtered, and dried in vacuum at 40° C. to afford 2.87 g light yellow solid. LC-MS (APCI): m/z=243.1 (M+1)⁺.

Step 4 3-cyano-6-(1-(methyl-d₃)-1H-pyrazol-4-yl)pyrazolo[1,5-a]pyridin-4-yl triflate N-Phenyl-bis(trifluoromethanesulfonimide) (4.71 g) was added to 4-hydroxy-6-(1-(methyl-d₃)-1H-pyrazol-4-yl)pyrazolo[1,5-a]pyridine-3-carbonitrile (2.87 g, 11.21 mmol) and DIPEA (4.17 mL) in DMA (25 mL), and the reaction was stirred at room temperature for 2 hrs. The reaction solution was added to water (300 mL) to quench the reaction, the solid was filtered, and washed with water (50 mL×3). The solid was dissolved in DCM (250 mL), dried over anhydrous sodium sulfate, the filtrate was concentrated under reduced pressure, and the concentrate was purified by column chromatography (PE/EtOAc=50%) and concentrated to give 2.4 g earthy gray solid. LC-MS (APCI): m/z=375.2 (M+1)⁺.

Step 5 The Synthesis of 4-(6-fluoropyridin-3-yl)-6-(1-(methyl-d₃)-1H-pyrazol-4-yl)pyrazolo[1,5-a]pyridine-3-carbonitrile Under nitrogen protection, Pd(PPh₃)₄ (185 mg, 0.16 mmol) was added to 3-cyano-6-(1-(methyl-d₃)-1H-pyrazol-4-yl)pyrazolo[1,5-a]pyridin-4-yl triflate (1.2 g, 3.20 mmol), 2-fluoro-5-(4,4,5,5-tetramethyl-1,3,2-dioxaborolan-2-yl)pyridine (1.08 g, 4.80 mmol) and sodium carbonate (1.70 g, 16 mmol) in mixed solvent of dioxane (32 mL) and water (8 mL), and under nitrogen protection, the reaction was conducted at 90° C. in sealed tube overnight. The reaction was cooled to room temperature, added with water (30 mL), and stirred thoroughly for 3 hrs. The solid was filtered, washed with water (10 mL×3) and cooled MTBE (5 mL×2), and dried in vacuum to afford 750 mg light yellow solid, Yield: 72.8%. LC-MS (APCI): m/z=322.1 (M+1)⁺.

Step 6 The Synthesis of tert-butyl 3-(5-(3-cyano-6-(1-(methyl-d₃)-1H-pyrazol-4-yl)pyrazolo[1,5-a]pyridin-4-yl)pyridin-2-yl)-3,6-diazabicyclo[3.1.1]heptane-6-carboxylate At room temperature, K₂CO₃ (1.24 g, 9.00 mmol) was added to 4-(6-fluoropyridin-3-yl)-6-(1-(methyl-d₃)-1H-pyrazol-4-yl)pyrazolo[1,5-a]pyridine-3-carbonitrile (580 mg, 1.80 mmol) and 6-(tert-butoxycarbonyl)-3,6-diazabicyclo[3.1.1]heptane (380 mg, 1.90 mmol) in anhydrous DMSO (9 mL), and the reaction was stirred at 95° C. overnight. The reaction was cooled to room temperature, the reaction system was diluted by adding H₂O, and washed with EtOAc for 3 times. The organic layers were combined, washed with saturated brine for 2 times, dried over anhydrous sodium sulfate, filtered, concentrated under reduced pressure, and the concentrate was purified by column chromatography (DCM/MeOH=5%) to give 700 mg light yellow solid, Yield: 77.9%. LC-MS (APCI): m/z=500.2 (M+1)⁺.

Step 7 The Synthesis of 4-(6-(3,6-diazabicyclo[3.1.1]heptan-3-yl)pyridin-3-yl)-6-(1-(methyl-d₃)-1H-pyrazol-4-yl)pyrazolo[1,5-a]pyridine-3-carbonitrile In an ice bath, TFA (10 mL) was added to a solution of tert-butyl 3-(5-(3-cyano-6-(1-(methyl-d₃)-1H-pyrazol-4-ylpyrazolo[1,5-a]pyridin-4-yl)pyridin-2-yl)-3,6-diazabicyclo[3.1.1]heptane-6-carboxylate (700 mg, 1.40 mmol) in DCM (10 mL), and the reaction was conducted at room temperature for 3 hrs. The reaction solution was concentrated under reduced pressure, adjusted to a basic pH with ammonia-methanol solution, concentrated under reduced pressure, and the concentrate was purified by column chromatography (DCM/MeOH=12%) to give 560 mg white solid. LC-MS (APCI): m/z=400.2 (M+1)⁺.

Intermediate P3: (R)-tert-butyl 2-(((3-cyano-4-(4,5,5-tetramethyl-1,3,2-dioxaborolan-2-yl)pyrazole[1,5-a]pyridin-6-yl)oxy)methyl)morpholine-4-carboxylate

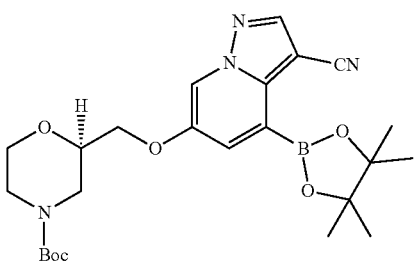

The following route was used for the synthesis:

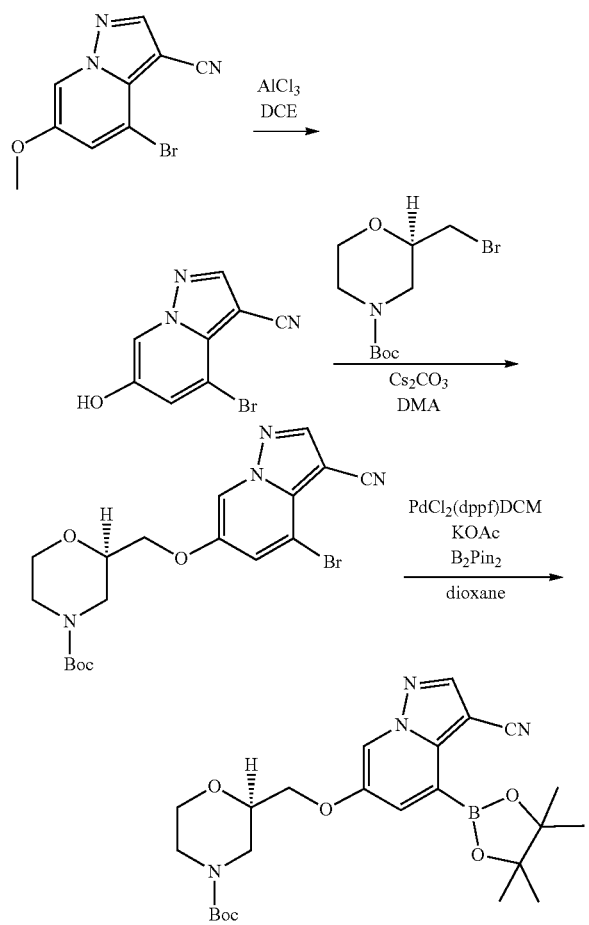

Step 1 The Synthesis of 4-bromo-6-hydroxypyrazolo[1,5-a]pyridine-3-carbonitrile

Under nitrogen protection, anhydrous aluminum trichloride (950 mg, 7.15 mmol) was added to 4-bromo-6-methoxypyrazolo[1,5-a]pyridine-3-carbonitrile (600 mg, 2.38 mmol) in anhydrous DCE (10 mL), and the reaction was stirred at 75° C. overnight. The reaction was cooled to room temperature, 100 mL of tetrahydrofuran was added to dilute the reaction solution, and the system was quenched by adding sodium sulfate decahydrate (10 eq). After stirring for 8 hrs at room temperature, the reaction solution was filtered, washed with tetrahydrofuran, and the filtrate was concentrated under reduced pressure. The concentrate was purified by slurrying with MTBE (2 mL) overnight, the solid was filtered, washed with cooled MTBE (1 mL), and dried in vacuum to afford 540 mg solid. Yield: 95.7%. LC-MS (APCI): m/z=235.9 (M−1)⁻.

Step 2 The Synthesis of (R)-tert-butyl 2-(((4-bromo-3-cyanopyrazolo[1,5-a]pyridin-6-yl)oxy)methyl)morpholine-4-carboxylate At room temperature, $Cs_2CO_3$ (2.2 g, 6.75 mmol) was added to a solution of 4-bromo-6-hydroxypyrazolo[1,5-a]pyridine-3-carbonitrile (540 mg, 2.25 mmol) and (R)-tert-butyl 2-(bromomethyl)-4-morpholine-carboxylate (630 mg, 2.25 mmol) in anhydrous DMA (4 mL), and under nitrogen protection, the reaction was conducted at 60° C. overnight. The reaction was cooled to room temperature, the reaction system was diluted by adding DCM (50 mL), washed with $H_2O$ (25 mL×3) and saturated brine (25 mL×2) respectively, and the organic layer was dried over anhydrous sodium sulfate. After concentrating under reduced pressure, the concentrate was purified by slurring with MTBE (2 mL) overnight, the solid was filtered, washed with cooled MTBE (1 mL), and dried in vacuum to afford 630 mg solid. Yield: 64.2%. LC-MS (APCI): m/z=437.2 (M+1)⁺.

Step 3 The Synthesis of (R)-tert-butyl 2-(((3-cyano-4-(4,4,5,5-tetramethyl-1,3,2-dioxaborolan-2-yl)pyrazole[1,5-a]pyridin-6-yl)oxy)methyl)morpholine-4-carboxylate Under nitrogen protection, $PdCl_2(dppf)DCM$ (100 mg) was added to (R)-tert-butyl 2-(((4-bromo-3-cyanopyrazolo[1,5-a]pyridin-6-yl)oxy)methyl)morpholine-4-carboxylate (510 mg, 1.16 mmol), bis(pinacolato)diboron (2.97 g, 11.68 mmol) and KOAc (580 mg, 5.92 mmol) in anhydrous dioxane (12 mL). Under nitrogen protection, the reaction was conducted at 80° C. in sealed tube overnight. The reaction was cooled to room temperature, the reaction system was diluted by adding DCM (150 mL), filtered through silica gel chromatography, and washed with DCM (150 mL). The filtrate was concentrated under reduced pressure, the concentrate was purified by slurring with n-pentane (50 mL), the solid was filtered, and dried in vacuum to afford 400 mg solid, which was directly used in the next step without purification. LC-MS (APCI): m/z=485.2 (M+1)⁺.

Intermediate P4: 4-bromo-6-(2-hydroxy-2-methylpropoxy)pyrazolo[1,5-a]pyridine-3-carbonitrile

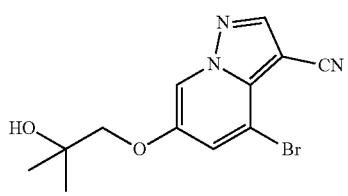

The following route was used for the synthesis:

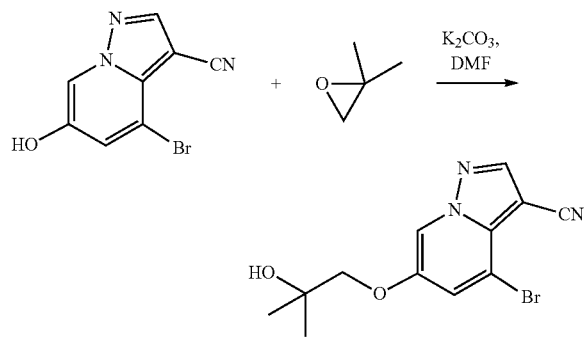

At room temperature, K₂CO₃ (2.2 g, 6.75 mmol) was added to a solution of 4-bromo-6-hydroxypyrazolo[1,5-a]pyridine-3-carbonitrile (720 mg, 3.00 mmol) and dimethyl ethylene oxide (2.2 g, 30.00 mmol) in anhydrous DMF (5 mL), and under nitrogen protection, the reaction was conducted at 60° C. in sealed tube for 8 hrs. The reaction was heated to 80° C. overnight. The reaction was cooled to room temperature, added with 50 mL, stirred for 1 hr, the solid was filtered, washed with cooled MTBE (1 mL), and dried in vacuum to afford 800 mg solid. LC-MS (APCI): m/z=310.0 (M+1)⁺.

Intermediate R1: 5-(chloromethyl)-2-(methoxy-d₃)pyridine

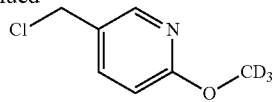

The following route was used for the synthesis:

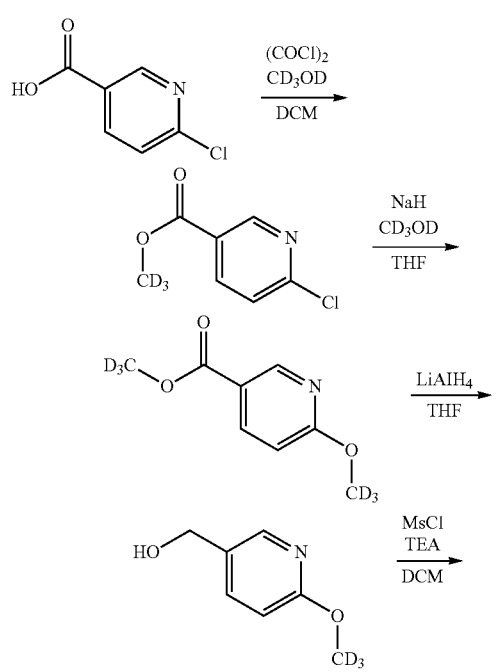

Step 1 The Synthesis of (methyl-d₃) 6-chloronicotinate

In an ice bath, oxalyl chloride (4.90 g) and 2 drops of DMF were added to 6-chloronicotinic acid (5 g) in anhydrous DCM (75 mL), and the reaction was stirred at room temperature for 24 hrs. The reaction solution was concentrated under increased pressure, and added with anhydrous DCM (35 mL). In an ice bath, deuterated methanol (5 mL) was added and naturally warmed, and reacted for 30 min. The reaction solution was concentrated under reduced pressure, diluted with MTBE, washed with water, saturated brine, respectively, dried over anhydrous sodium sulfate, filtered, concentrated under reduced pressure, and the concentrate was purified by column chromatography (PE/EtOAc=10%) to give 5.34 g light yellow solid. ¹H NMR (500 MHz, CDCl₃) δ 9.04-8.96 (m, 1H), 8.26 (dd, J=8.3, 2.4 Hz, 1H), 7.43 (dd, J=8.3, 0.5 Hz, 1H).

Step 2 The Synthesis of (methyl-d₃) 6-(methoxy-d₃)chloronicotinate

In an ice bath, NaH (1.62 g, 60%) was added in batchs to a solution of deuterated methanol (1.34 g) in anhydrous THF (50 mL), the reaction was treated with ice bath again after stirring at room temperature for 1 hrs, (methyl-d₃) 6-chloronicotinate (5.3 g) was added to the reaction system, and the reaction was conducted at room temperature for 4 hrs. The reaction was quenched by adding water, extracted with EtOAc, and the organic layer was washed with saturated brine. The resulted solution was dried over anhydrous sodium sulfate, filtered, concentrated under reduced pressure, and the concentrate was purified by column chromatography (PE/EtOAc=30%) to give 4.5 g light yellow solid. LC-MS (APCI): m/z=174.1 (M+1)⁺.

Step 3 The Synthesis of (6-(methoxy-d₃)pyridin-3-yl)methanol

In an ice bath, lithium aluminium hydride (402 mg) was added to a solution of (methyl-d₃) 6-(methoxy-d₃)chloronicotinate (1.5 g) in anhydrous tetrahydrofuran (30 mL), and the reaction was conducted at room temperature for 2 hrs. The reaction was quenched with sodium sulfate decahydrate, tetrahydrofuran (150 mL) was added, the solution was stirred thoroughly for 4 hrs, filtered, washed with THF, the filtrate was concentrated under reduced pressure, and the concentrate was purified by column chromatography (PE/EtOAc=40%) to give 840 mg light yellow oil, liquid yield: 72.9%. LC-MS (APCI): m/z=143.1 (M+1)⁺.

Step 4 The Synthesis of 5-(chloromethyl)-2-(methoxy-d₃)pyridine

In an ice bath, MsCl (1.02 g) was added to (6-(methoxy-d₃)pyridin-3-yl)methanol (840 mg) in TEA (1.19 g) and anhydrous DCM (20 mL), and the reaction was conducted at room temperature overnight. The reaction was quenched by adding water, extracted with DCM, and the organic layer was washed with saturated brine. The reaction solution was dried over anhydrous sodium sulfate, filtered, concentrated under reduced pressure, and the concentrate was purified by column chromatography (PE/EtOAc=16%) to give 800 mg light yellow oil. LC-MS (APCI): m/z=161.1 (M+1)$^+$, $^1$H NMR (300 MHz, CDCl$_3$) δ 8.15 (d, J=2.4 Hz, 1H), 7.63 (dd, J=8.6, 2.5 Hz, 1H), 6.76 (d, J=8.6 Hz, 1H), 4.55 (s, 2H).

Intermediate R2:
5-(chloromethyl-d$_2$)-2-methoxypyridine

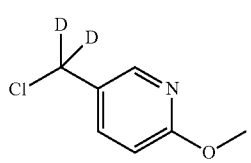

The following route was used for the synthesis:

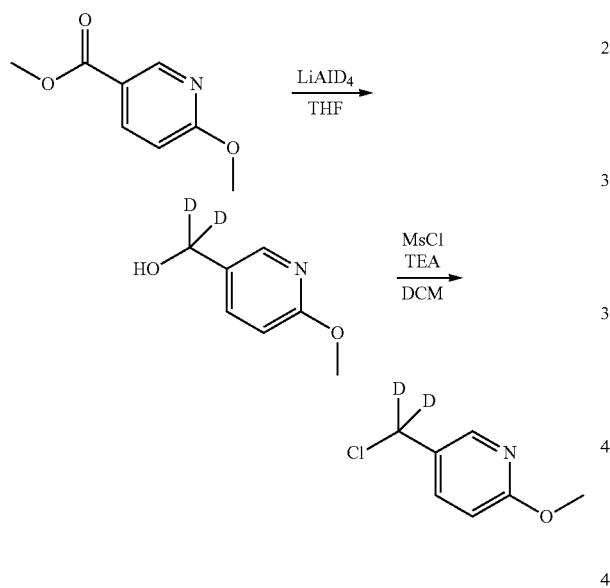

Step 1 The Synthesis of
(6-methoxypyridin-3-yl)methane-d$_2$-ol

In an ice bath, tetra-deuterium aluminum lithium (1.00 g) was added to a solution of methyl 6-methoxynicotinate (3.78 g) in anhydrous tetrahydrofuran (50 mL), and the reaction was conducted at room temperature for 2 hrs. The reaction was quenched with sodium sulfate decahydrate, added with tetrahydrofuran (200 mL), stirred thoroughly for 4 hrs, filtered, washed with THF, the filtrate was concentrated under reduced pressure, and the concentrate was purified by column chromatography (PE/EtOAc=40%) to give 1.56 g light yellow oil. LC-MS (APCI): m/z=142.1 (M+1)$^+$.

Step 2 The Synthesis of Compound
5-(chloromethyl-d$_2$)-2-methoxypyridine

In an ice bath, MsCl (1.52 g, 13.27 mmol) was added to (6-methoxypyridin-3-yl) methyl-d$_2$-ol (1.56 g, 11.06 mmol) in TEA (1.68 g, 16.59 mmol) in anhydrous DCM (40 mL), and the reaction was conducted at room temperature overnight. The reaction was quenched by adding water, extracted with DCM, and the organic layer was washed with saturated brine. The reaction solution was dried over anhydrous sodium sulfate, filtered, concentrated under reduced pressure, and the concentrate was purified by column chromatography (PE/EtOAc=16%) to give 1.2 g light yellow oil. LC-MS (APCI): m/z=163.1 (M+1)$^+$, $^1$H NMR (400 MHz, CDCl$_3$) δ 8.17 (d, J=2.3 Hz, 1H), 7.64 (dd, J=8.6, 2.5 Hz, 1H), 6.78 (d, J=8.6 Hz, 1H), 3.96 (s, 3H).

Intermediate R3: 5-(chloromethyl-d$_2$)-2-(methoxy-d$_3$)pyridine

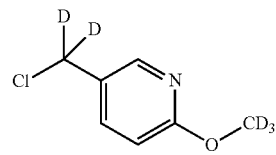

The following route was used for the synthesis:

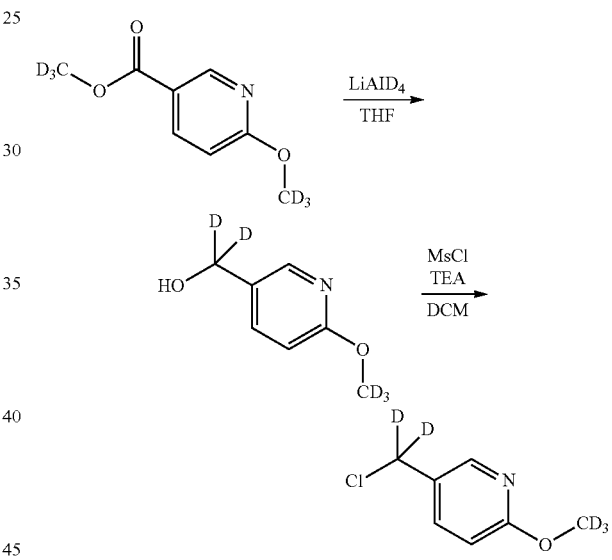

Step 1 The Synthesis of (6-(methoxy-d$_3$)pyridin-3-yl)methane-d$_2$-ol

In an ice bath, tetra-deuterium aluminum lithium (444 mg) was added to a solution of (methyl-d$_3$) 6-(methoxy-d$_3$) nicotinate (1.5 g) in anhydrous tetrahydrofuran (30 mL), and the reaction was conducted at room temperature for 2 hrs. The reaction was quenched with sodium sulfate decahydrate, added with tetrahydrofuran (150 mL), stirred thoroughly for 4 hrs, filtered, washed with THF, the filtrate was concentrated under reduced pressure, and the concentrate was purified by column chromatography (PE/EtOAc=40%) to give 670 mg light yellow oil, liquid yield: 58.2%. LC-MS (APCI): m/z=145.1 (M+1)$^+$.

Step 2 The Synthesis of 5-(chloromethyl-d$_2$)-2-(methoxy-d$_3$)pyridine

In an ice bath, MsCl (803 mg) was added to (6-(methoxy-d$_3$)pyridin-3-yl)methyl-d$_2$-ol (670 mg) in TEA (940 mg) in anhydrous DCM (20 mL), and the reaction was conducted at room temperature overnight. The reaction was quenched by adding water, extracted with DCM, and the organic layer was washed with saturated brine. The reaction solution was dried over anhydrous sodium sulfate, filtered, concentrated under reduced pressure, and the concentrate was purified by column chromatography (PE/EtOAc=16%) to give 560 mg light yellow oil. LC-MS (APCI): m/z=163.1 (M+1)$^+$, $^1$H NMR (500 MHz, CDCl$_3$) δ 8.22-8.05 (m, 1H), 7.63 (dd, J=8.6, 2.5 Hz, 1H), 6.76 (dd, J=8.6, 0.6 Hz, 1H).

Intermediate R4: 3-(5-chloropyrazine-2-yl)-6-((6-methoxypyridin-3-yl)methyl-d$_2$)-3,6-diazabicyclo[3.1.1]heptane

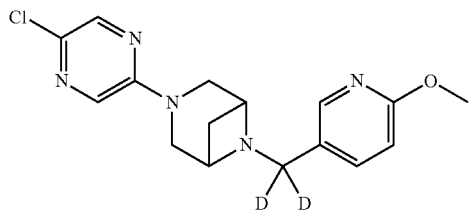

The following route was used for the synthesis:

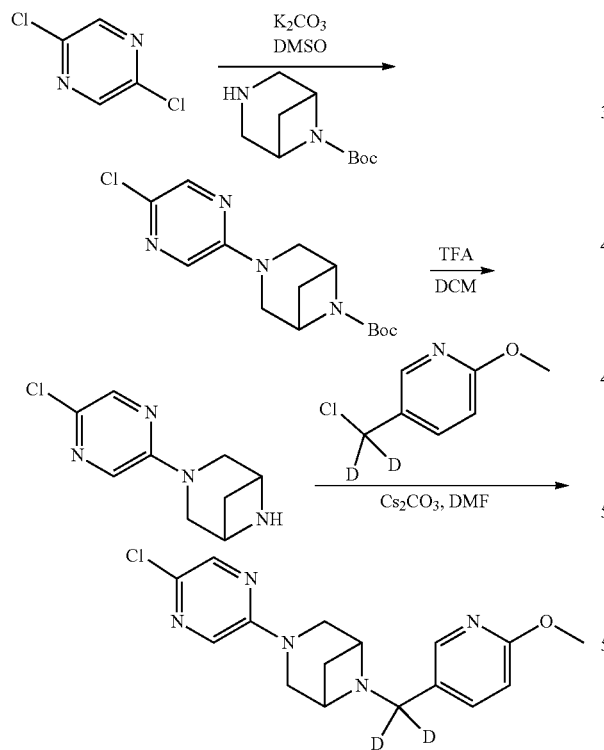

Step 1 The Synthesis of tert-butyl 3-(5-chloropyrazine-2-yl)-3,6-diazabicyclo[3.1.1]heptane-6-carboxylate At room temperature, K$_2$CO$_3$ was added to 2,5-dichloropyrazine (2.60 g, 17.4 mmol) and 6-(tert-butoxycarbonyl)-3,6-diazabicyclo[3.1.1]heptane (3.10 g, 15.66 mmol) in anhydrous DMSO, and the reaction was stirred at 85° C. overnight. The reaction was cooled to room temperature, the reaction system was diluted by adding H$_2$O, and extracted with EtOAc for 3 times. The organic layers were combined, washed with saturated brine, dried over anhydrous sodium sulfate, filtered, concentrated under reduced pressure, and the concentrate was purified by column chromatography (PE/EtOAc=15-30%) to give 4.0 g light yellow solid, Yield: 62.83%. LC-MS (APCI): m/z=313.1 (M+1)$^+$.

Step 2 The synthesis of 3-(5-chloropyrazin-2-yl)-3,6-diazabicyclo[3.1.1]heptane

In an ice bath, TFA (15 mL) was added to tert-butyl 3-(5-chloropyrazin-2-yl)-3,6-diazabicyclo[3.1.1]heptane-6-carboxylate (2.3 g, 7.37 mmol) in anhydrous DCM (15 mL), and the reaction was conducted at room temperature for 4 hrs. The reaction solution was concentrated under reduced pressure, the pH of the residue was adjusted to alkaline with saturated sodium bicarbonate solution, the resulted solution was extracted with DCM for 3 times, the organic layers were combined, washed with saturated brine, dried over anhydrous sodium sulfate, filtered, concentrated under reduced pressure, and the concentrate was purified by column chromatography (DCM/MeOH=10%) to give 1.34 g light yellow solid, Yield: 86.5%. LC-MS (APCI): m/z=211.1 (M+1)$^+$.

Step 3 The Synthesis of 3-(5-chloropyrazine-2-yl)-6-((6-methoxypyridin-3-yl)methyl-d$_2$)-3,6-diazabicyclo[3.1.1]heptane At room temperature, Cs$_2$CO$_3$ (1.55 g) was added to 3-(5-chloropyrazin-2-yl)-3,6-diazabicyclo[3.1.1]heptane (500 mg) and 5-(chloromethyl-d$_2$)-2-methoxypyridine (405 mg) in anhydrous DMF (10 mL), and the reaction was stirred at 90° C. for 5 hrs. The reaction was cooled to room temperature, the reaction system was diluted by adding H$_2$O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=5%) to give 600 mg light yellow solid. LC-MS (APCI): m/z=334.1 (M+1)$^+$.

Intermediate R5: 3-(5-chloropyrazin-2-yl)-6-((6-(methoxy-d$_3$)pyridin-3-yl)methyl)-3,6-diazabicyclo[3.1.1]heptane

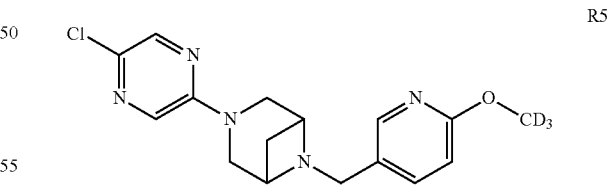

The following route was used for the synthesis:

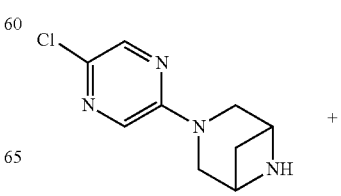

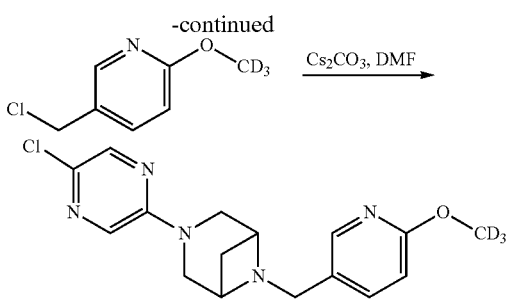

At room temperature, Cs$_2$CO$_3$ (1.55 g) was added to 3-(5-chloropyrazin-2-yl)-3,6-diazabicyclo[3.1.1]heptane (295 mg) and 5-(chloromethyl)-2-(methoxy-d3)pyridine (240 mg) in anhydrous DMF (5 mL), and the reaction was stirred at 90° C. for 5 hrs. The reaction was cooled to room temperature, the reaction system was diluted by adding H$_2$O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=5%) to give 320 mg light yellow solid. LC-MS (APCI): m/z=335.1 (M+1)$^+$.

Intermediate R6: 3-(5-chloropyrazin-2-yl)-6-((6-(methoxy-d$_3$)pyridin-3-yl)methyl-d$_2$)-3,6-diazabicyclo[3.1.1]heptane

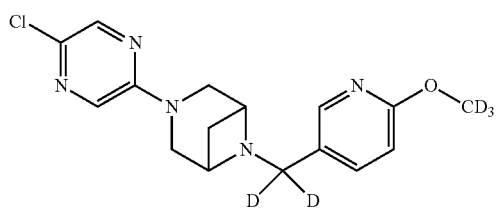

The following route was used for the synthesis:

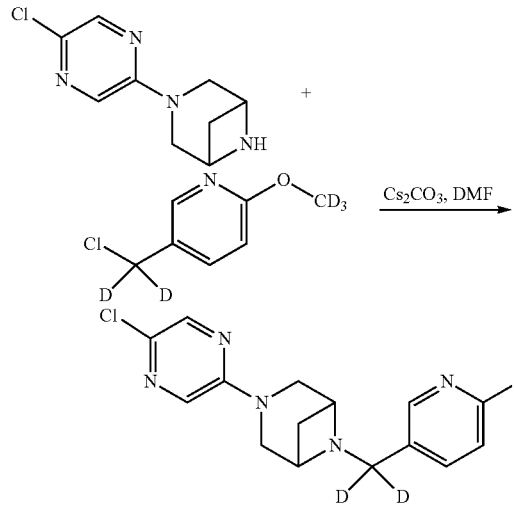

At room temperature, Cs$_2$CO$_3$ (1.55 g) was added to 3-(5-chloropyrazin-2-yl)-3,6-diazabicyclo[3.1.1]heptane (359 mg, 1.85 mmol) and 5-(chloromethyl-d$_2$)-2-(methoxy-d$_3$)pyridine (300 mg, 1.85 mmol) in anhydrous DMF (5 mL), and the reaction was stirred at 90° C. overnight. The reaction was cooled to room temperature, the reaction system was diluted by adding H$_2$O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=5%) to give 400 mg light yellow solid. LC-MS (APCI): m/z=337.2 (M+1)$^+$.

Intermediate R7: 6-((6-methoxypyridin-3-yl)methyl-d$_2$)-3-(5-(4,4,5,5-tetramethyl-1,3,2-dioxaborolan-2-yl)pyridin-2-yl)-3,6-diazabicyclo[3.1.1]heptane

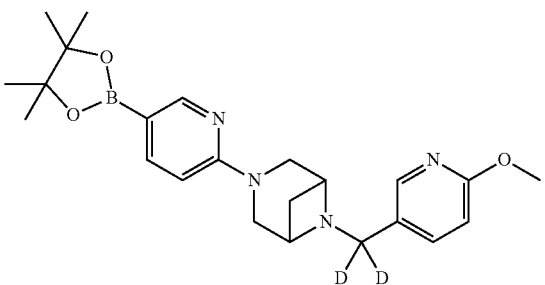

The following route was used for the synthesis:

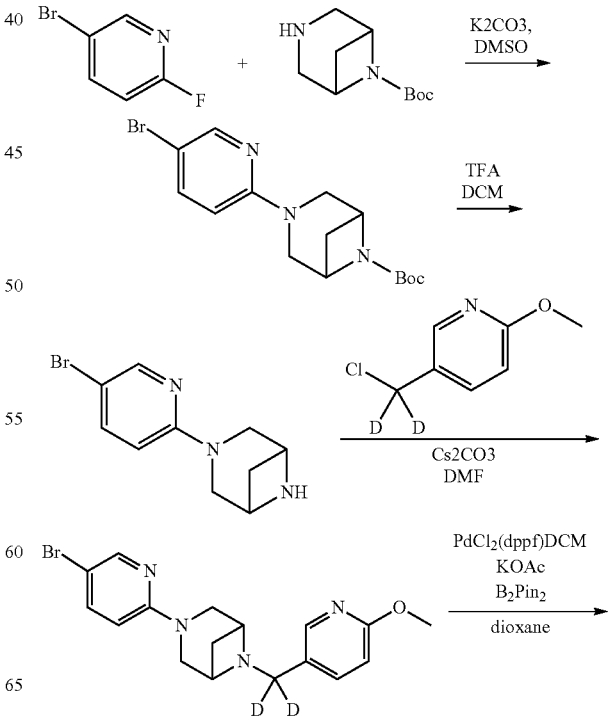

83
-continued

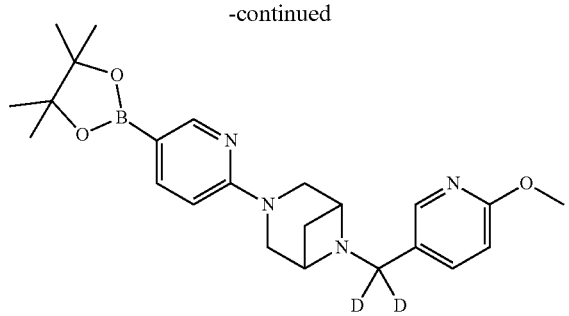

Step 1 The Synthesis of tert-butyl 3-(5-bromopyridin-2-yl)-3,6-diazabicyclo[3.1.1]heptane-6-carboxylate At room temperature, $K_2CO_3$ was added to 5-bromo-2-fluoropyridine (919 mg, 5.22 mmol) and 6-(tert-butoxycarbonyl)-3,6-diazabicyclo[3.1.1]heptane (1.00 g, 5.22 mmol) in anhydrous DMSO (8 mL), and the reaction was stirred at 90° C. for 24 hrs. The reaction was cooled to room temperature, the reaction system was diluted by adding $H_2O$, and extracted with EtOAc for 3 times. The organic layers were combined, washed with saturated brine, dried over anhydrous sodium sulfate, filtered, concentrated under reduced pressure, and the concentrate was purified by column chromatography (PE/EtOAc=10%) to give 1.6 g light yellow solid, Yield: 86.8%. LC-MS (APCI): m/z=354.1 (M+1)$^+$.

Step 2 The Synthesis of 3-(5-bromopyridin-2-yl)-3,6-diazabicyclo[3.1.1]heptane

In an ice bath, TFA (10 mL) was added to tert-butyl 3-(5-bromopyridin-2-yl)-3,6-diazabicyclo[3.1.1]heptane-6-carboxylate (1.5 g, 4.25 mmol) in anhydrous DCM (10 mL), and the reaction was conducted at room temperature for 4 hrs. The reaction solution was concentrated under reduced pressure, the pH of the residue was adjusted to alkaline with saturated sodium bicarbonate solution, the resulted solution was extracted with DCM for 3 times, the organic layers were combined, washed with saturated brine, dried over anhydrous sodium sulfate, filtered, concentrated under reduced pressure, and the concentrate was purified by column chromatography (DCM/MeOH=10%) to give 1.05 g light yellow solid, Yield: 97.6%. LC-MS (APCI): m/z=254.1 (M+1)$^+$.

Step 3 The Synthesis of 3-(5-bromopyridin-2-yl)-6-((6-methoxypyridin-3-yl)methyl-d$_2$)-3,6-diazabicyclo[3.1.1]heptane At room temperature, $Cs_2CO_3$ (1.30 g, 4.00 mmol) was added to 3-(5-bromopyridin-2-yl)-3,6-diazabicyclo[3.1.1]heptane (504 mg, 2.00 mmol) and 5-(chloromethyl-d$_2$)-2-methoxypyridine (400 mg, 2.40 mmol) in anhydrous DMF (8 mL), and the reaction was stirred at 90° C. overnight. The reaction was cooled to room temperature, the reaction system was diluted by adding $H_2O$, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 540 mg light yellow solid, Yield: 71.6%. LC-MS (APCI): m/z=377.0 (M+1)$^+$.

84
Step 4 6-((6-methoxypyridin-3-yl)methyl-d$_2$)-3-(5-(4,4,5,5-tetramethyl-1,3,2-dioxaborolan-2-yl)pyridin-2-yl)-3,6-diazabicyclo[3.1.1]heptane Under nitrogen protection, PdCl$_2$(dppf)DCM (115 mmol, 0.14 mmol) was added to 3-(5-bromopyridin-2-yl)-6-((6-methoxypyridin-3-yl)methyl-d$_2$)-3,6-diazabicyclo[3.1.1]heptane (540 mg, 1.43 mmol), B$_2$(Pin)$_2$ (1.10 g, 4.29 mmol) and KOAc (429 mg, 4.29 mmol) in a solvent of dioxane (16 mL). Under nitrogen protection, the reaction was conducted at 80° C. overnight. The reaction was cooled to room temperature, filtered with diatomaceous earth, the filter cake was washed with EtOAc, the filtrate was concentrated under reduced pressure, and the concentrate was purified by column chromatography (DCM/MeOH=5%) to give 250 mg light yellow solid, Yield: 41.1%. LC-MS (APCI): m/z=425.2 (M+1)$^+$.

Intermediate R8: 6-((6-(methoxy-d$_3$)pyridin-3-yl)methyl)-3-(5-(4,4,5,5-tetramethyl-1,3,2-dioxaborolan-2-yl)pyridin-2-yl)-3,6-diazabicyclo[3.1.1]heptane

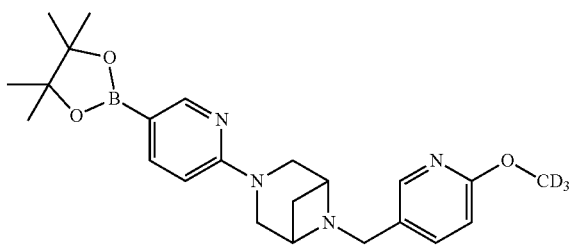

The following route was used for the synthesis:

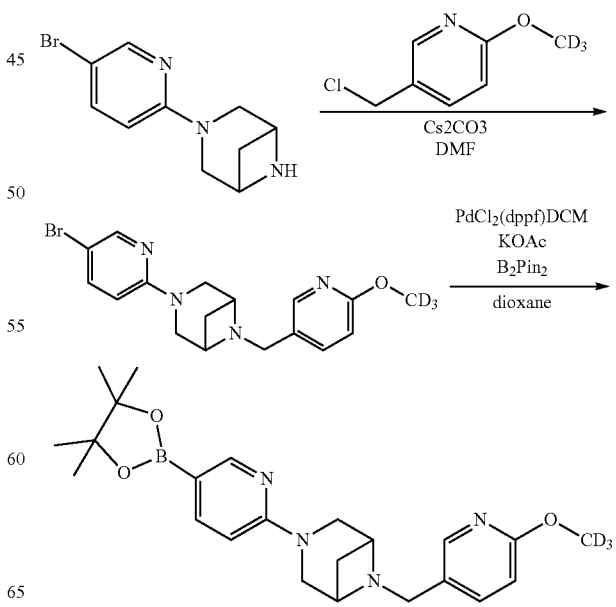

Step 1 The Synthesis of 3-(5-bromopyridin-2-yl)-6-((6-(methoxy-d₃)pyridin-3-yl)methyl)-3,6-diazabicyclo[3.1.1]heptane At room temperature, Cs₂CO₃ (1.30 g, 4.00 mmol) was added to 3-(5-bromopyridin-2-yl)-3,6-diazabicyclo[3.1.1]heptane (504 mg, 2.00 mmol) and 5-(chloromethyl)-2-(methoxy-d₃)pyridine (400 mg, 2.40 mmol) in anhydrous DMF (8 mL), and the reaction was stirred at 90° C. overnight. The reaction was cooled to room temperature, the reaction system was diluted by adding H₂O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 470 mg light yellow solid, Yield: 62.3%. LC-MS (APCI): m/z=378.1 (M+1)⁺.

Step 2 The Synthesis of 6-((6-(methoxy-d₃)pyridin-3-yl)methyl)-3-(5-(4,4,5,5-tetramethyl-1,3,2-dioxaborolan-2-yl)pyridin-2-yl)-3,6-diazabicyclo[3.1.1]heptane Under nitrogen protection, PdCl₂(dppf)DCM (100 mg) was added to 3-(5-bromopyridin-2-yl)-6-((6-(methoxy-d₃)pyridin-3-yl)methyl)-3,6-diazabicyclo[3.1.1]heptane (470 mg, 1.24 mmol), B₂(Pin)₂ (950 mg, 3.73 mmol) and KOAc (370 mg, 3.73 mmol) in a solvent of dioxane (15 mL). Under nitrogen protection, and the reaction was conducted at 80° C. overnight. The reaction was cooled to room temperature, filtered with diatomaceous earth, the filter cake was washed with EtOAc, the filtrate was concentrated under reduced pressure, and the concentrate was purified by column chromatography (DCM/MeOH=5%) to give 270 mg light yellow solid, Yield: 51.1%. LC-MS (APCI): m/z=426.2 (M+1)⁺.

Intermediate R9: 6-((6-(methoxy-d₃)pyridin-3-yl)methyl-d₂)-3-(5-(4,4,5,5-tetramethyl-1,3,2-dioxaborolan-2-yl)pyridin-2-yl)-3,6-diazabicyclo[3.1.1]heptane

R9

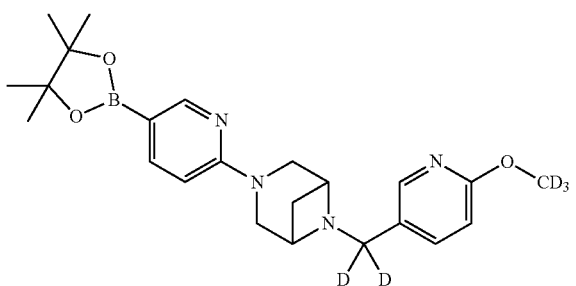

The following route was used for the synthesis:

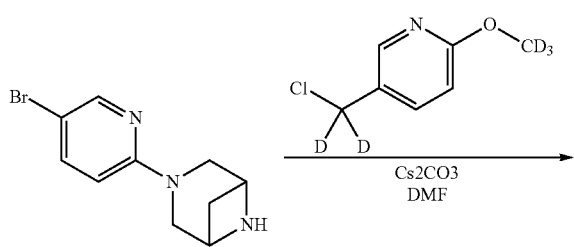

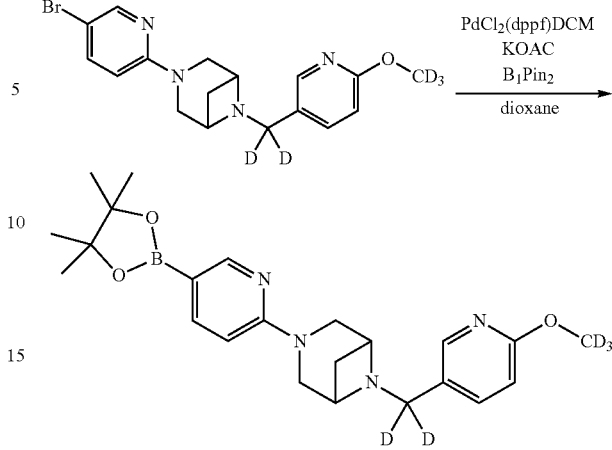

Step 1 The Synthesis of 3-(5-bromopyridin-2-yl)-6-((6-(methoxy-d₃)pyridin-3-yl)methyl-d₂)-3,6-diazabicyclo[3.1.1]heptane At room temperature, Cs₂CO₃ ((1.30 g, 4.00 mmol) was added to 3-(5-bromopyridin-2-yl)-3,6-diazabicyclo[3.1.1]heptane (504 mg, 2.00 mmol) and 5-(chloromethyl-d₂)-2-(methoxy-d₃)pyridine (400 mg, 2.40 mmol) in anhydrous DMF (8 mL), and the reaction was stirred at 90° C. overnight. The reaction was cooled to room temperature, the reaction system was diluted by adding H₂O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 450 mg light yellow solid, Yield: 70.6%. LC-MS (APCI): m/z=380.1 (M+1)⁺.

Step 2 6-((6-(methoxy-d₃)pyridin-3-yl)methyl-d₂)-3-(5-(4,4,5,5-tetramethyl-1,3,2-dioxaborolan-2-yl)pyridin-2-yl)-3,6-diazabicyclo[3.1.1]heptane Under nitrogen protection, PdCl₂(dppf)DCM (100 mmol) was added to 3-(5-bromopyridin-2-yl)-6-((6-(methoxy-d₃)pyridin-3-yl)methyl-d₂)-3,6-diazabicyclo[3.1.1]heptane (450 mg, 1.18 mmol), B₂(Pin)₂ (900 mg, 3.55 mmol) and KOAc (350 mg, 3.55 mmol) in a solvent of dioxane (15 mL). Under nitrogen protection, the reaction was conducted at 80° C. overnight. The reaction was cooled to room temperature, filtered with diatomaceous earth, the filter cake was washed with EtOAc, the filtrate was concentrated under reduced pressure, and the concentrate was purified by column chromatography (DCM/MeOH=5%) to give 236 mg light yellow solid, Yield: 46.7%. LC-MS (APCI): m/z=428.1 (M+1)⁺.

Intermediate R10: 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane

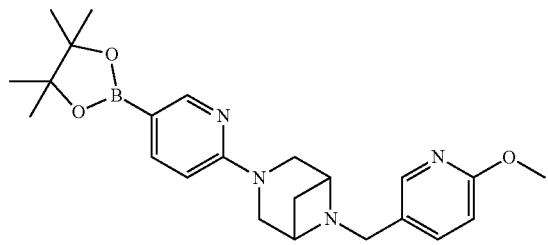

R10

The following route was used for the synthesis:

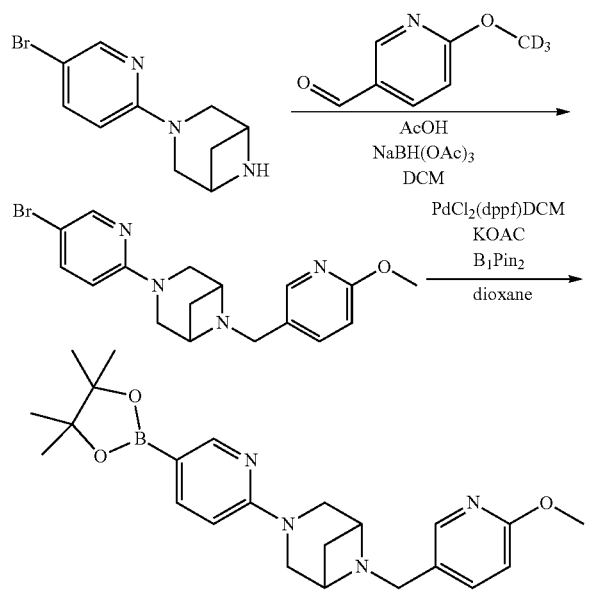

Step 1 The synthesis of 3-(5-bromopyridin-2-yl)-6-((6-methoxypyridin-3-yl)methyl)-3,6-diazabicyclo[3.1.1]heptane In an ice bath, few drops of acetic acid was dropped into 3-(5-bromopyridin-2-yl)-3,6-diazabicyclo[3.1.1]heptane (1.05 g, 3.94 mmol) and 6-methoxynicotinaldehyde (594 mg, 4.33 mmol) in anhydrous DCM (25 mL), and the reaction was stirred at room temperature for 30 min. In an ice bath, NaBH(OAc)$_3$ (1.25 g, 5.91 mmol) was added, and the reaction was stirred overnight. The reaction was quenched with saturated sodium bicarbonate solution, the water layer was extracted with DCM (50 mL×3), the organic layers were combined, concentrated under reduced pressure, and the concentrate was purified by column chromatography (DCM/MeOH=6%) to give 1.15 g light yellow solid. LC-MS (APCI): m/z=375.1 (M+1)$^+$, $^1$H NMR (400 MHz, CDCl$_3$) δ 8.26 (d, J=2.2 Hz, 1H), 8.07 (d, J=1.9 Hz, 1H), 7.66-7.57 (m, 2H), 6.72 (d, J=8.5 Hz, 1H), 6.46 (d, J=9.0 Hz, 1H), 3.92 (s, 3H), 3.79-3.69 (m, 4H), 3.53 (s, 2H), 3.48 (d, J=11.7 Hz, 2H), 2.68 (dd, J=13.8, 6.8 Hz, 1H), 1.61 (d, J=8.6 Hz, 1H).

Step 2 The Synthesis of 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane Under nitrogen protection, PdCl$_2$(dppf)DCM (228 mg, 0.28 mmol) was added to 3-(5-bromopyridin-2-yl)-6-((6-methoxypyridin-3-yl)methyl)-3,6-diazabicyclo[3.1.1]heptane (1.05 g, 2.80 mmol), B$_2$(Pin)$_2$ (2.13 g, 8.40 mmol) and KOAc (825 mg, 8.40 mmol) in a solvent of dioxane (28 mL). Under nitrogen protection, the reaction was conducted at 80° C. overnight. The reaction was cooled to room temperature, filtered with diatomaceous earth, the filter cake was washed with EtOAc, the filtrate was concentrated under reduced pressure, and the concentrate was purified by column chromatography (DCM/MeOH=5%) to give 840 mg light yellow solid, Yield: 71.1%. LC-MS (APCI): m/z=423.4 (M+1)$^+$.

Example 1 4-(6-(6-((6-(methoxy-d$_3$)pyridin-3-yl)methyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile The following route was used for the synthesis:

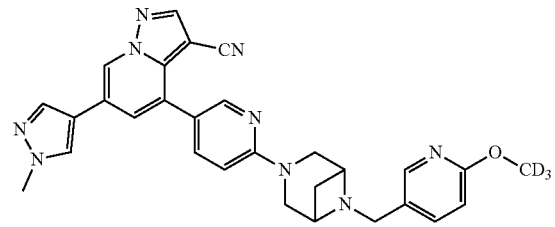 [SMILES: [2H]C([2H])([2H])Oc1ccc(CN2C3CC2CN(c2ccc(-c4cc(-c5cnn(C)c5)cn5ncc(C#N)c45)cn2)C3)cn1]

89

-continued

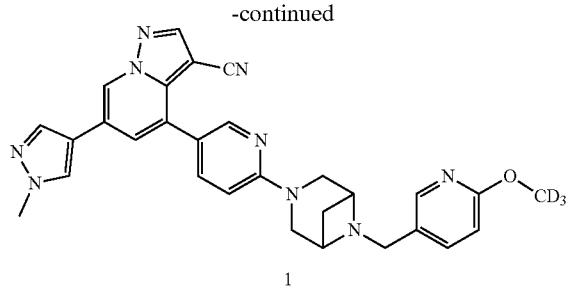

At room temperature, Cs$_2$CO$_3$ (392 mg) was added to intermediate P1 (160 mg, 60%) and intermediate R1 (76 mg) in anhydrous DMF (5 mL), and the reaction was stirred at 95° C. overnight. The reaction was cooled to room temperature, the reaction system was diluted by adding H$_2$O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 68 mg white solid, purity: 99.36% (HPLC). LC-MS (APCI): m/z=521.4 (M+1)$^+$.

Example 2 4-(6-(6-(((6-methoxypyridin-3-yl)methyl-d$_2$)-3,6-diazabicyclo[3.1.1]heptan-3-yl)pyridin-3-yl)-6-(1-methyl-1H-pyrazol-4-yl)pyrazolo[1,5-a]pyridine-3-carbonitrile

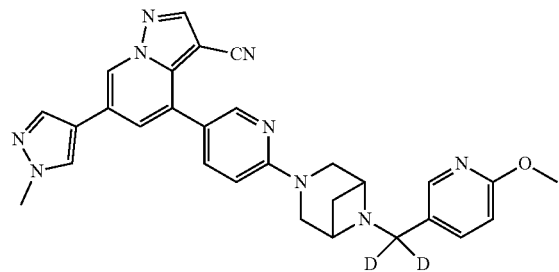 [SMILES: [2H]C([2H])(c1ccc(OC)nc1)N1C2CC1CN(c1ccc(-c3cc(-c4cnn(C)c4)cn4ncc(C#N)c34)cn1)C2]

The following route was used for the synthesis:

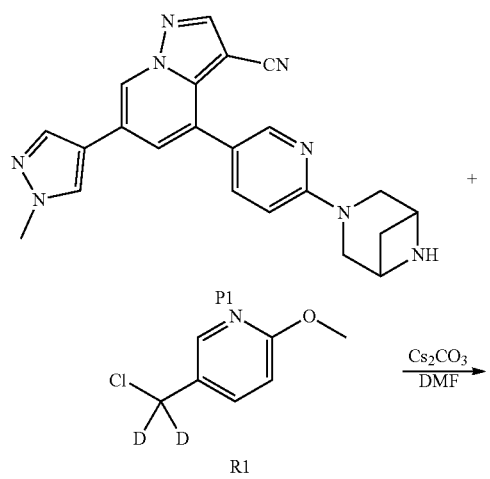

90

-continued

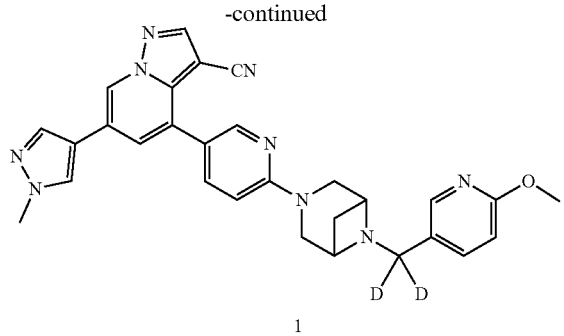

At room temperature, Cs$_2$CO$_3$ (488 mg, 1.50 mmol) was added to intermediate P1 (200 mg, 0.50 mmol, 60%) and intermediate R2 (100 mg, 0.60 mmol) in anhydrous DMF (5 mL), and the reaction was stirred at 95° C. overnight. The reaction was cooled to room temperature, the reaction system was diluted by adding H$_2$O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 90 mg white solid, purity: 99.74% (HPLC). LC-MS (APCI): m/z=520.4 (M+1)$^+$.

Example 3 4-(6-(6-(((6-(methoxy-d$_3$)pyridin-3-yl)methyl-d$_2$)-3,6-diazabicyclo[3.1.1]heptan-3-yl)pyridin-3-yl)-6-(1-methyl-1H-pyrazol-4-yl)pyrazolo[1,5-a]pyridine-3-carbonitrile

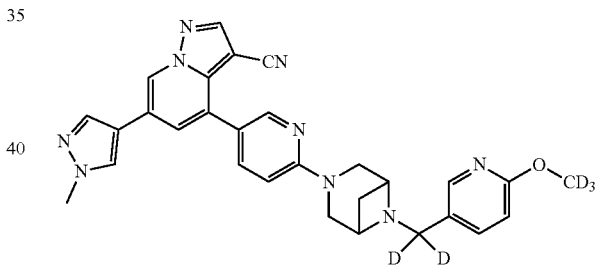

The following route was used for the synthesis:

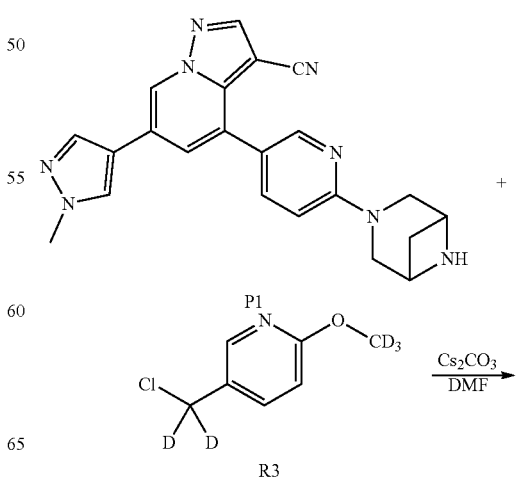

-continued

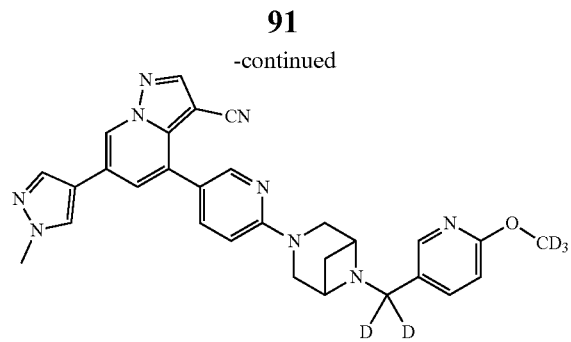

At room temperature, Cs₂CO₃ (592 mg) was added to intermediate P1 (160 mg, 60%) and intermediate R3 (80 mg) in anhydrous DMF (5 mL), and the reaction was stirred at 95° C. overnight. The reaction was cooled to room temperature, the reaction system was diluted by adding H₂O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 40 mg white solid, purity: 98.84% (HPLC). LC-MS (APCI): m/z=523.4 (M+1)⁺.

Example 4 4-(6-(6-(((6-(methoxy-d₃)pyridin-3-yl)methyl)-3,6-diazabicyclo[3.1.1]heptan-3-yl)pyridin-3-yl)-6-(1-(methyl-d₃)-1H-pyrazol-4-yl)pyrazolo[1,5-a]pyridine-3-carbonitrile

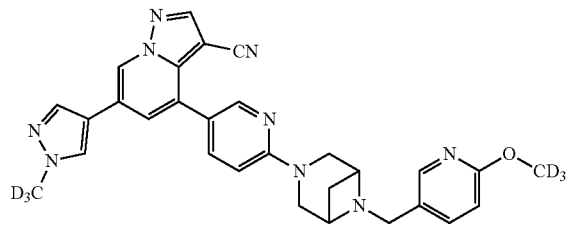 [SMILES: [2H]C([2H])([2H])Oc1ccc(CN2C3CC2CN(c2ccc(-c4cc(-c5cnn(C([2H])([2H])[2H])c5)cn5ncc(C#N)c45)cn2)C3)cn1]

The following route was used for the synthesis:

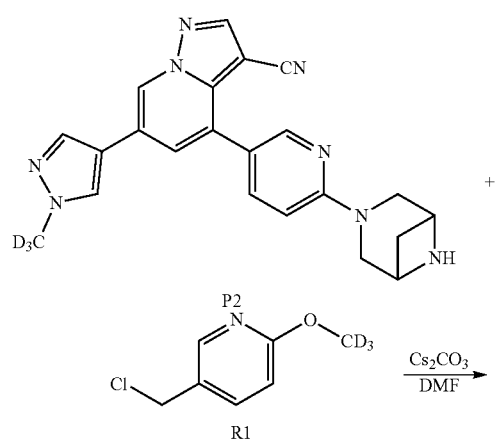

-continued

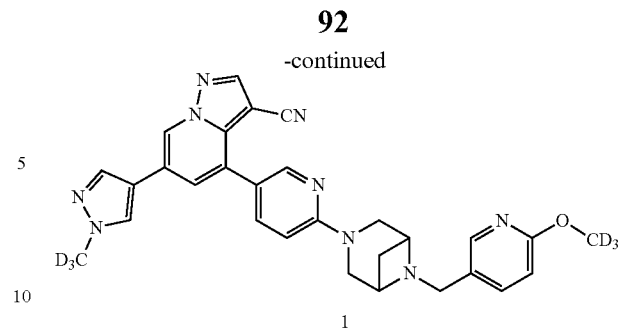

At room temperature, Cs₂CO₃ (196 mg, 0.60 mmol) was added to intermediate P2 (80 mg, 0.20 mmol) and intermediate R1 (38 mg, 0.24 mmol) in anhydrous DMF (3 mL), and the reaction was stirred at 95° C. overnight. The reaction was cooled to room temperature, the reaction system was diluted by adding H₂O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 63 mg white solid, Yield: 60.2%, purity: 98.51% (HPLC). LC-MS (APCI): m/z=524.4 (M+1)⁺.

Example 5 4-(6-(6-(((6-methoxypyridin-3-yl)methyl-d₂)-3,6-diazabicyclo[3.1.1]heptan-3-yl)pyridin-3-yl)-6-(1-(methyl-d₃)-1H-pyrazol-4-yl)pyrazolo[1,5-a]pyridine-3-carbonitrile

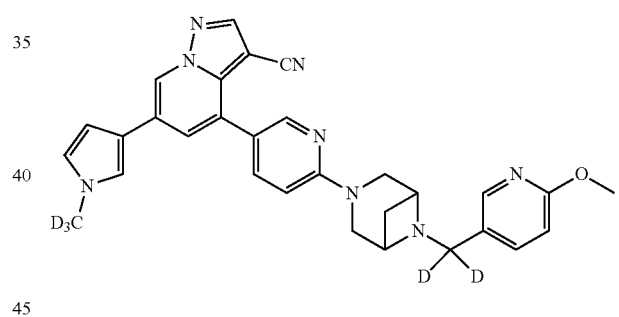

The following route was used for the synthesis:

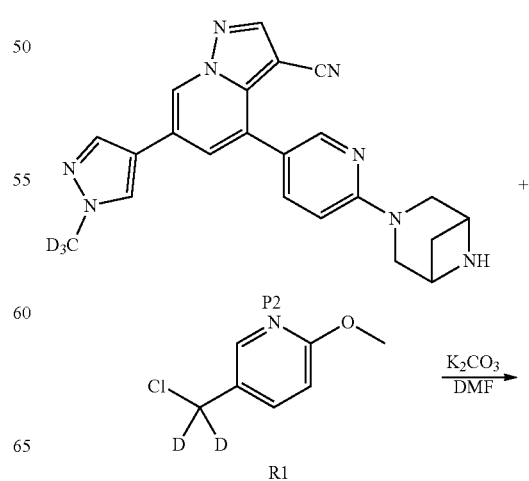

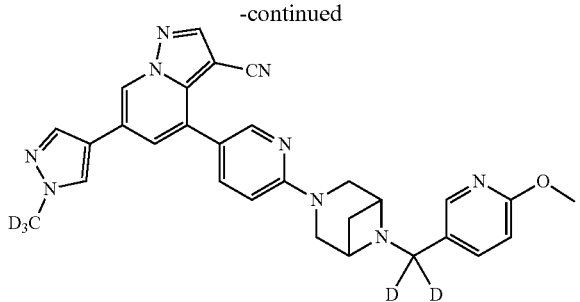

At room temperature, Cs₂CO₃ (1.6 g, 3.00 mmol) was added to intermediate P2 (400 mg, 1.00 mmol, purity 30%) and intermediate R2 (160 mg, 1.00 mmol) in anhydrous DMF (5 mL), and the reaction was stirred at 95° C. overnight. The reaction was cooled to room temperature, the reaction system was diluted by adding H₂O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 50 mg white solid, purity: 99.29% (HPLC). LC-MS (APCI): m/z=523.4 (M+1)⁺.

Example 6 4-(6-(6-((6-(methoxy-d₃)pyridin-3-yl)methyl-d₂)-3,6-diazabicyclo[3.1.1]heptan-3-yl)pyridin-3-yl)-6-(1-(methyl-d₃)-1H-pyrazol-4-yl)pyrazolo[1,5-a]pyridine-3-carbonitrile At room temperature, Cs₂CO₃ (196 mg, 0.60 mmol) was added to intermediate P2 (80 mg, 0.2 mmol) and intermediate R3 (40 mg, 0.24 mmol) in anhydrous DMF (3 mL), and the reaction was stirred at 95° C. overnight. The reaction was cooled to room temperature, the reaction system was diluted by adding H₂O, and extracted with EtOAc for 3 times. The organic layers were combined, washed with saturated brine, dried over anhydrous sodium sulfate, filtered, concentrated under reduced pressure, and the concentrate was purified by column chromatography (DCM/MeOH=6%) to give 33 mg white solid, Yield: 31.5%, purity: 98.95% (HPLC). LC-MS (APCI): m/z=526.4 (M+1)⁺.

Example 7 4-(6-(6-((6-methoxypyridin-3-yl)methyl)-3,6-diazabicyclo[3.1.1]heptan-3-yl)pyridin-3-yl)-6-(1-(methyl-d₃)-1H-pyrazol-4-yl)pyrazolo[1,5-a]pyridine-3-carbonitrile

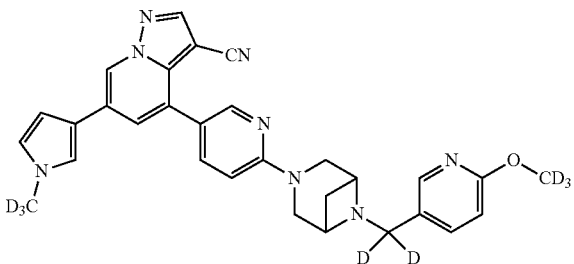 [SMILES: [2H]C([2H])([2H])Oc1ccc(C([2H])([2H])N2C3CC2CN(c2ccc(-c4cc(-c5ccn(C([2H])([2H])[2H])c5)cn5ncc(C#N)c45)cn2)C3)cn1]

The following route was used for the synthesis:

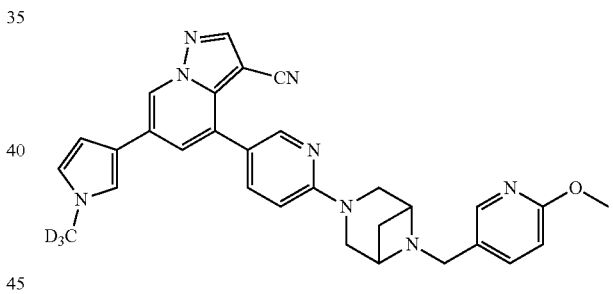

The following route was used for the synthesis:

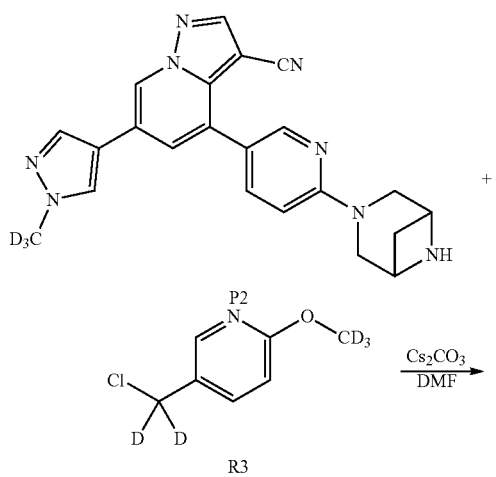

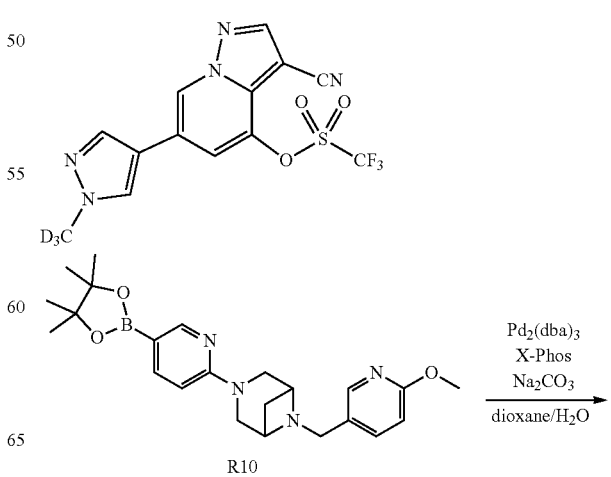

-continued

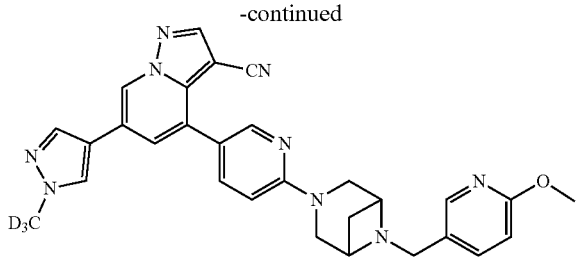

Under nitrogen protection, Pd₂(dba)₂ (37 mg) and X-phos (38 mg) was added to intermediate R10 (204 mg, 0.48 mmol), 3-cyano-6-(1-(methyl-d₃)-1H-pyrazol-4-yl)pyrazolo[1,5-a]pyridin-4-yl triflate (150 mg, 0.40 mmol) and sodium carbonate (216 mg, 2.06 mmol) in mixed solvent of dioxane (4 mL) and water (1 mL), and under nitrogen protection, the reaction was conducted at 85° C. overnight. The reaction was cooled to room temperature, filtered with diatomaceous earth, the filter cake was washed with DCM, the filtrate was concentrated under reduced pressure, and the concentrate was purified by column chromatography (DCM/ MeOH=6%) to give 140 mg white solid. purity: 93.99% (HPLC). LC-MS (APCI): m/z=521.4 (M+1)⁺.

Example 8 4-(5-(6-(((6-methoxypyridin-3-yl)methyl-d₂)-3,6-diazabicyclo[3.1.1]heptan-3-yl)pyrazin-2-yl)-6-(((R)-morpholin-2-yl)methoxy))pyrazolo[1,5-a]pyridine-3-carbonitrile The following route was used for the synthesis:

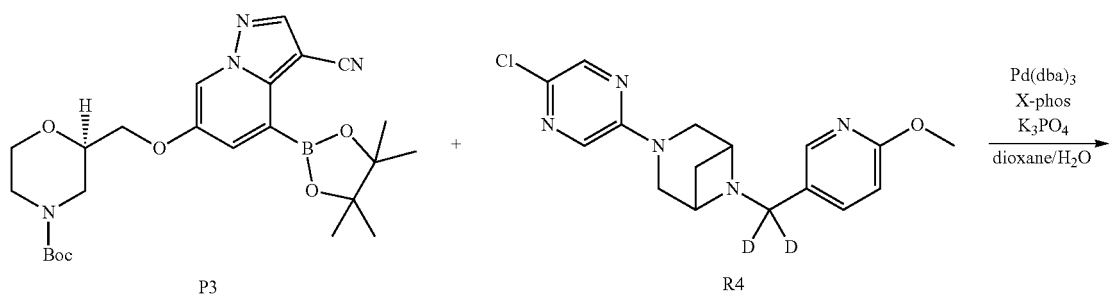

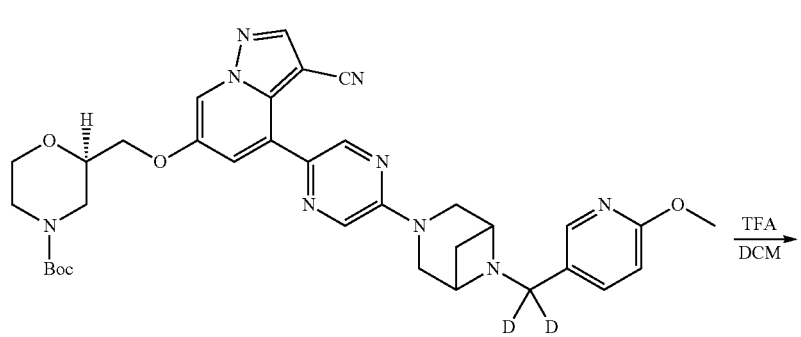

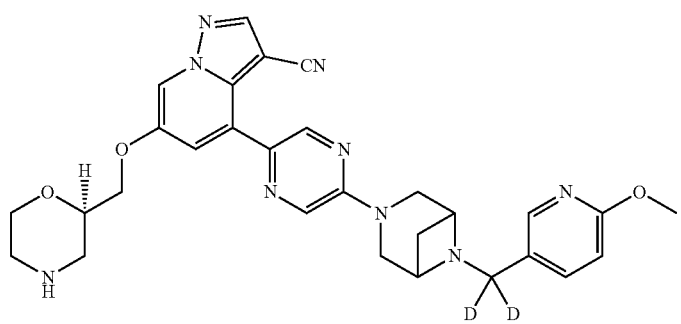

Step 1 The Synthesis of (2R)-tert-butyl 2-(((3-cyano-4-(5-(6-((6-methoxypyridin-3-yl)methyl-d₂)-3,6-diazabicyclo[3.1.1]heptan-3-yl)pyrazin-2-yl)pyrazole[1,5-a]pyridin-6-yl)oxy)methyl)morpholine-4-carboxylate Under nitrogen protection, Pd$_2$(dba)$_3$ (20 mg) and X-Phos (20 mg) was added to intermediate R4 (80 mg), intermediate P3 (100 mg) and K$_3$PO$_4$ (127 mg) in mixed solvent of dioxane (2 mL) and water (0.5 mL). Under nitrogen protection, the reaction was conducted at 80° C. in sealed tube overnight. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 45 mg light yellow solid. LC-MS (APCI): m/z=656.4 (M+1)⁺.

Step 2 The Synthesis of 4-(5-(6-((6-methoxypyridin-3-yl)methyl-d₂)-3,6-diazabicyclo[3.1.1]heptan-3-yl)pyrazin-2-yl)-6-(((R)-morpholin-2-yl)methoxy))pyrazolo[1,5-a]pyridine-3-carbonitrile In an ice bath, TFA (1 mL) was added to a solution of (2R)-tert-butyl 2-(((3-cyano-4-(5-(6-((6-methoxypyridin-3-yl)methyl-d₂)-3,6-diazabicyclo[3.1.1]heptan-3-yl)pyrazin-2-yl)pyrazole[1,5-a]pyridin-6-yl)oxy)methyl)morpholine-4-carboxylate (45 mg) in DCM (2 mL), and the reaction was conducted at room temperature for 2 hrs. The reaction solution was concentrated under reduced pressure, adjusted to a basic pH with ammonia-methanol solution, concentrated under reduced pressure, and the concentrate was purified by column chromatography (DCM/MeOH=10%) to give 30 mg gray solid. purity: 96.45% (HPLC). LC-MS (APCI): m/z=556.4 (M+1)⁺.

Example 9 4-(5-(6-((6-(methoxy-d₃)pyridin-3-yl)methyl)-3,6-diazabicyclo[3.1.1]heptan-3-yl)pyrazin-2-yl)-6-(((R)-morpholin-2-yl)methoxy))pyrazolo[1,5-a]pyridine-3-carbonitrile

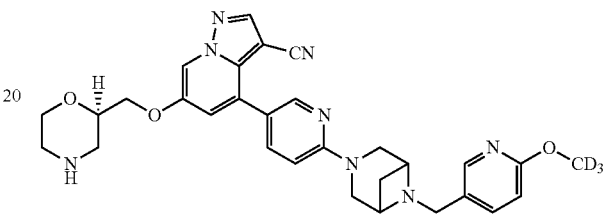

The following route was used for the synthesis:

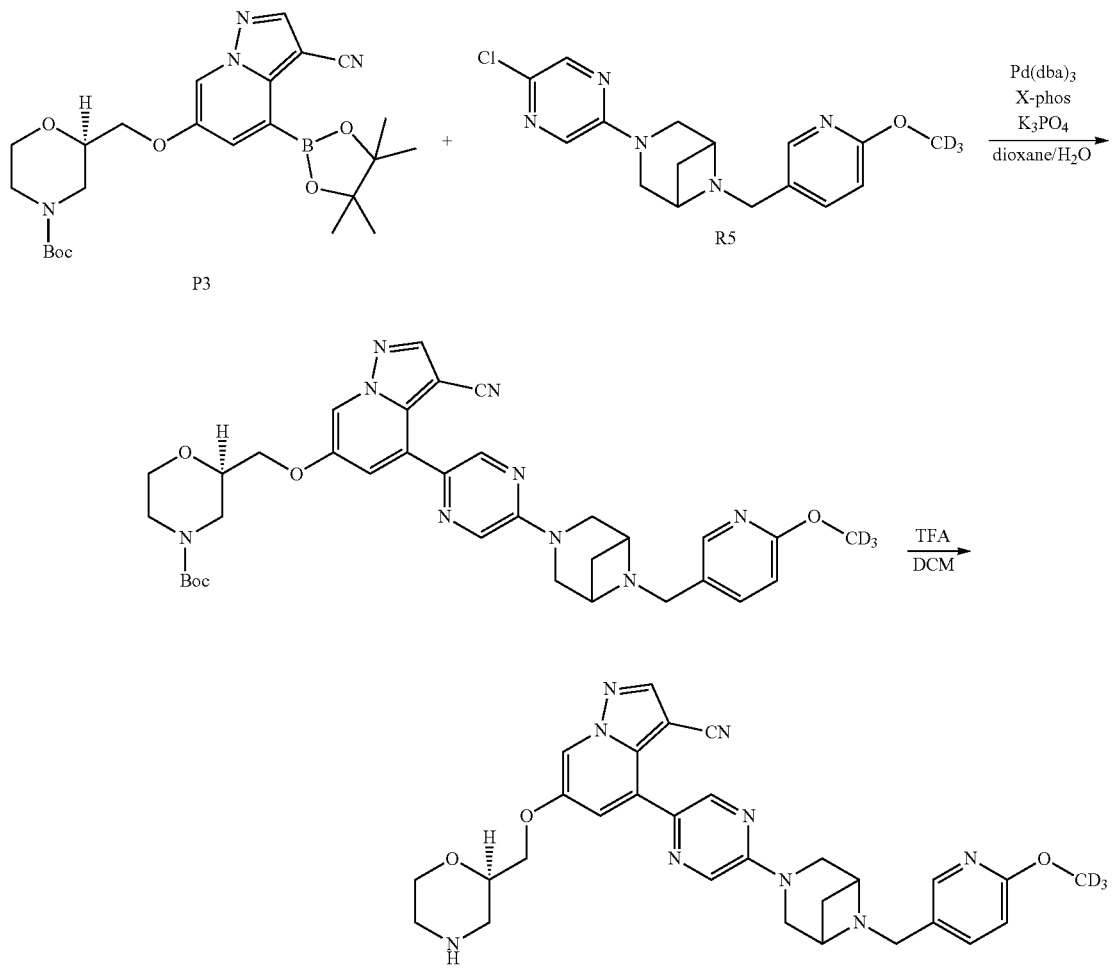

Step 1 The Synthesis of (2R)-tert-butyl 2-(((3-cyano-4-(5-(6-(((6-(methoxy-d₃)pyridin-3-yl)methyl)-3,6-diazabicyclo[3.1.1]heptan-3-yl)pyrazin-2-yl)pyrazole[1,5-a]pyridin-6-yl)oxy)methyl)morpholine-4-carboxylate Under nitrogen protection, Pd$_2$(dba)$_3$ (35 mg) and X-Phos (35 mg) were added to intermediate R5 (120 mg), intermediate P3 (150 mg) and K$_3$PO$_4$ (220 mg) in mixed solvent of dioxane (2 mL) and water (0.5 mL). Under nitrogen protection, the reaction was conducted at 80° C. in sealed tube overnight. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 60 mg light yellow solid. LC-MS (APCI): m/z=657.3 (M+1)$^+$.

Step 2 The Synthesis of 4-(5-(6-(((6-(methoxy-d₃)pyridin-3-yl)methyl)-3,6-diazabicyclo[3.1.1]heptan-3-yl)pyrazin-2-yl)-6-(((R)-morpholin-2-yl)methoxy))pyrazolo[1,5-a]pyridine-3-carbonitrile In an ice bath, TFA (1 mL) was added to a solution of (2R)-2-(((3-cyano-4-(5-(6-(((6-(methoxy-d₃)pyridin-3-yl)methyl)-3,6-diazabicyclo[3.1.1]heptan-3-yl)pyrazin-2-yl)pyrazole[1,5-a]pyridin-6-yl)oxy)methyl)morpholine-4-tert-butyl carboxylate (60 mg) in DCM (2 mL), and the reaction was conducted at room temperature for 2 hrs. The reaction solution was concentrated under reduced pressure, adjusting pH to alkaline with ammonia-methanol solution, concentrated under reduced pressure, and the concentrate was purified by column chromatography (DCM/MeOH=10%) to give 36 mg gray solid. purity: 98.00% (HPLC). LC-MS (APCI): m/z=557.2 (M+1)$^+$.

Example 10 4-(5-(6-(((6-(methoxy-d₃)pyridin-3-yl)methyl-d₂)-3,6-diazabicyclo[3.1.1]heptan-3-yl)pyrazin-2-yl)-6-(((R)-morpholin-2-yl)methoxy))pyrazolo[1,5-a]pyridine-3-carbonitrile

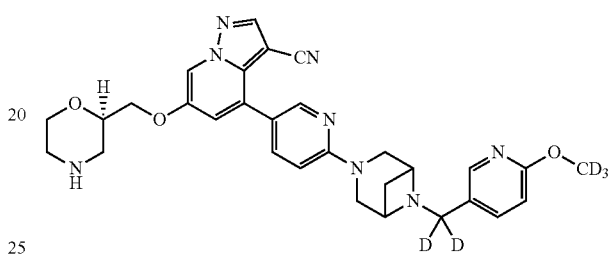

The following route was used for the synthesis:

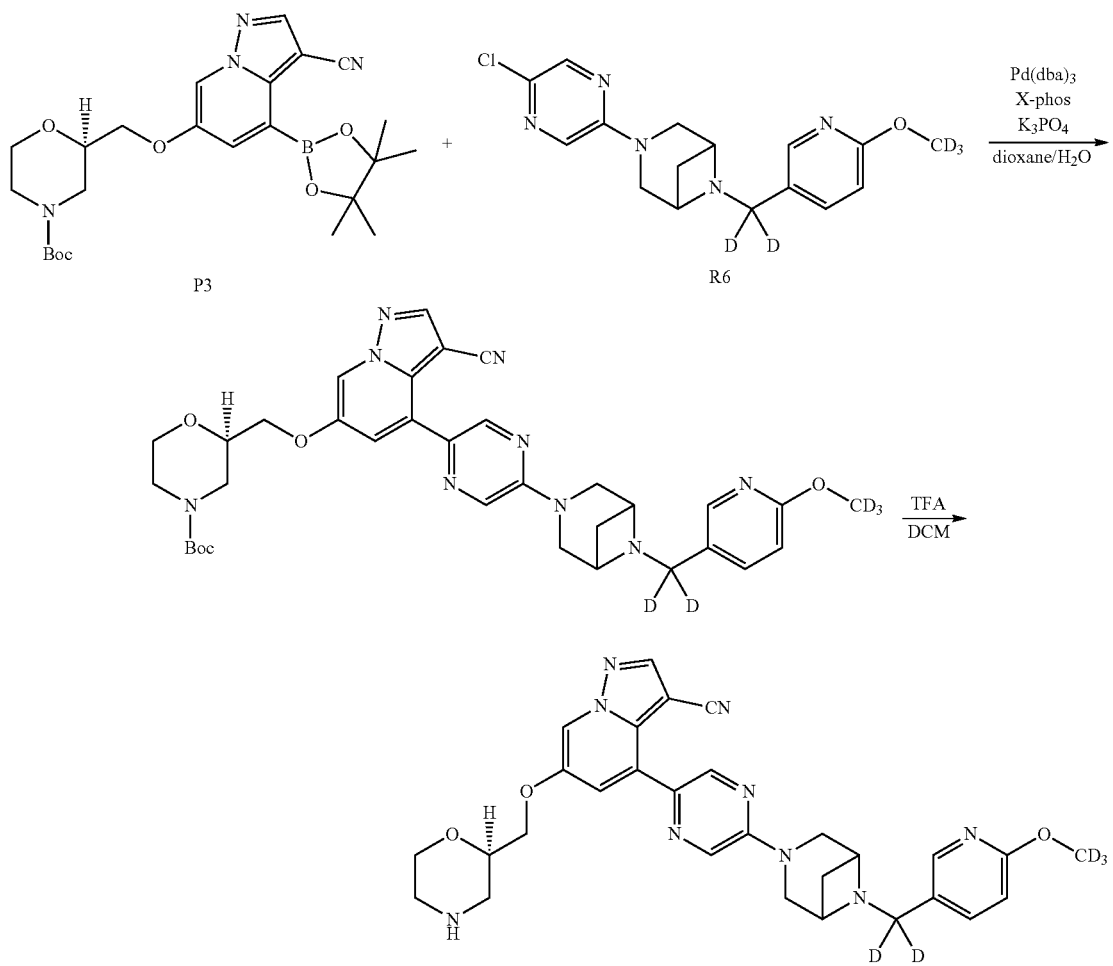

Step 1 The Synthesis of (2R)-tert-butyl 2-(((3-cyano-4-(5-(6-(((6-(methoxy-d₃)pyridin-3-yl)methyl-d₂)-3,6-diazabicyclo[3.1.1]heptan-3-yl)pyrazin-2-yl)pyrazole[1,5-a]pyridin-6-yl)oxy)methyl)morpholine-4-carboxylate Under nitrogen protection, Pd₂(dba)₃ (35 mg) and X-Phos (35 mg) were added to intermediate R6 (120 mg), intermediate P3 (150 mg) and K₃PO₄ (220 mg) in mixed solvent of dioxane (2 mL) and water (0.5 mL). Under nitrogen protection, the reaction was conducted at 80° C. in sealed tube overnight. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 98 mg light yellow solid. LC-MS (APCI): m/z=659.3 (M+1)⁺.

Step 2 The Synthesis of 4-(5-(6-(((6-(methoxy-d₃)pyridin-3-yl)methyl-d₂)-3,6-diazabicyclo[3.1.1]heptan-3-yl)pyrazin-2-yl)-6-(((R)-morpholin-2-yl)methoxy))pyrazolo[1,5-a]pyridine-3-carbonitrile In an ice bath, TFA (1 mL) was added to a solution of (2R)-tert-butyl 2-(((3-cyano-4-(5-(6-(((6-(methoxy-d₃)pyridin-3-yl)methyl-d₂)-3,6-diazabicyclo[3.1.1]heptan-3-yl)pyrazin-2-yl)pyrazole[1,5-a]pyridin-6-yl)oxy)methyl)morpholine-4-carboxylate (98 mg) in DCM (2 mL), and the reaction was conducted at room temperature for 2 hrs. The reaction solution was concentrated under reduced pressure, adjusted to a basic pH with ammonia-methanol solution, concentrated under reduced pressure, and the concentrate was purified by column chromatography (DCM/MeOH=10%) to give 35 mg gray solid. purity: 97.92% (HPLC). LC-MS (APCI): m/z=559.2 (M+1)⁺.

Example 11 6-(2-hydroxy-2-methylpropoxy)-4-(6-(6-(((6-methoxypyridin-3-yl)methyl-d₂)-3,6-diazabicyclo[3.1.1]heptan-3-yl)pyridin-3-yl)pyrazolo[1,5-a]pyridine-3-carbonitrile

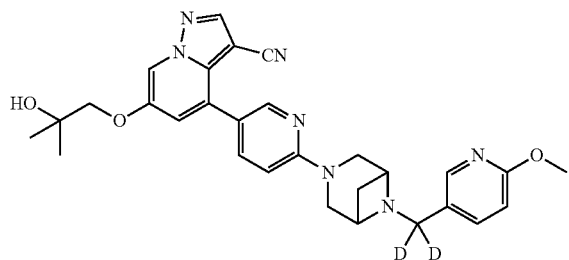 [SMILES: [2H]C([2H])(c1ccc(OC)nc1)N1C2CC1CN(c1ccc(-c3cc(OCC(C)(C)O)cn4ncc(C#N)c34)cn1)C2]

The following route was used for the synthesis:

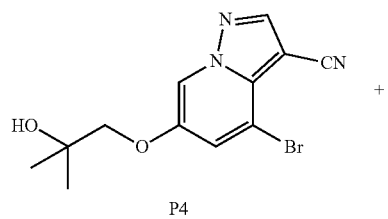

Under nitrogen protection, Pd(PPh₃)₄ (60 mg, 0.05 mmol) was added to intermediate R7 (250 mg, 0.59 mmol), intermediate P4 (150 mg, 0.48 mmol) and K₂CO₃ (166 mg, 1.2 mmol) in mixed solvent of dioxane (9 mL) and water (3 mL). Under nitrogen protection, the reaction was conducted at 85° C. overnight. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 110 mg light yellow solid. Yield: 43.5%. purity: 96.61% (HPLC). LC-MS (APCI): m/z=528.1 (M+1)⁺. ¹H NMR (500 MHz, DMSO) δ 8.70 (s, 1H), 8.61 (s, 1H), 8.47-8.38 (m, 1H), 8.09 (s, 1H), 7.86 (d, J=8.6 Hz, 1H), 7.70 (d, J=7.2 Hz, 1H), 7.32 (s, 1H), 6.87-6.73 (m, 2H), 4.74 (s, 1H), 3.90 (s, 2H), 3.84 (s, 3H), 3.79-3.65 (m, 4H), 3.63-3.50 (m, 2H), 2.50-2.44 (m, 1H), 1.65-1.54 (m, 1H), 1.25 (s, 6H).

Example 12 6-(2-hydroxy-2-methylpropoxy)-4-(6-(6-(((6-(methoxy-d₃)pyridin-3-yl)methyl)-3,6-diazabicyclo[3.1.1]heptan-3-yl)pyridin-3-yl)pyrazolo[1,5-a]pyridine-3-carbonitrile

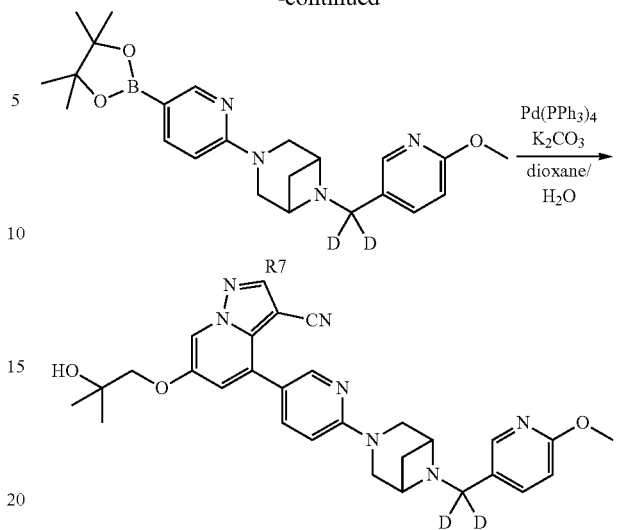

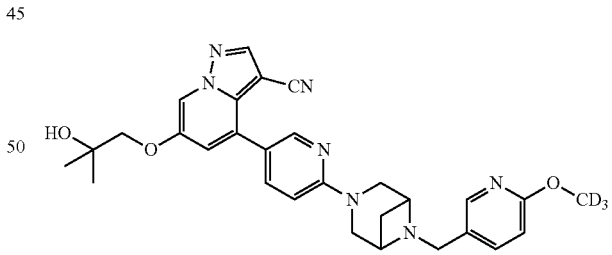

The following route was used for the synthesis:

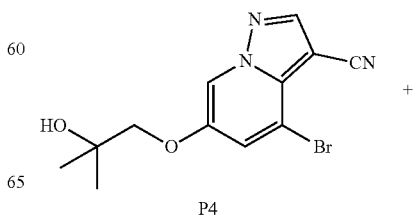

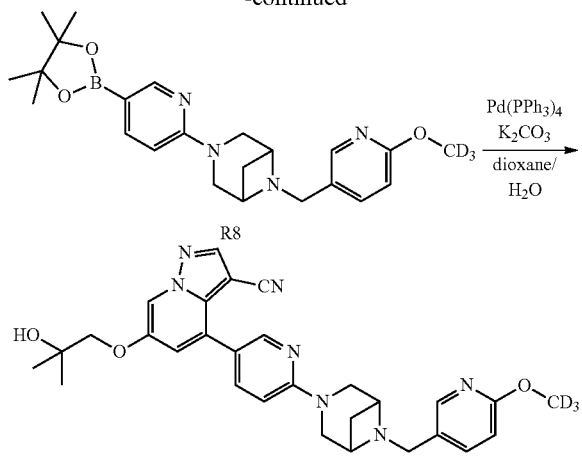

Under nitrogen protection, Pd(PPh₃)₄ (60 mg, 0.05 mmol) was added to intermediate R8 (270 mg, 0.63 mmol), intermediate P4 (150 mg, 0.48 mmol) and K₂CO₃ (170 mg, 1.2 mmol) in mixed solvent of dioxane (9 mL) and water (3 mL). Under nitrogen protection, the reaction was conducted at 85° C. overnight. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 70 mg light yellow solid. purity: 96.83% (HPLC). LC-MS (APCI): m/z=529.2 (M+1)⁺. ¹H NMR (500 MHz, DMSO) δ 8.69 (s, 1H), 8.61 (s, 1H), 8.48-8.36 (m, 1H), 8.08 (s, 1H), 7.86 (dd, J=8.8, 1.8 Hz, 1H), 7.69 (dd, J=8.2, 1.3 Hz, 1H), 7.32 (s, 1H), 6.86-6.72 (m, 2H), 4.74 (s, 1H), 3.90 (s, 2H), 3.79-3.66 (m, 4H), 3.61-3.46 (m, 4H), 2.53-2.43 (m, 1H), 1.63-1.57 (m, 1H), 1.25 (s, 6H).

Example 13 6-(2-hydroxy-2-methylpropoxy)-4-(6-(6-((6-(methoxy-d₃)pyridin-3-yl)methyl-d₂)-3,6-diazabicyclo[3.1.1]heptan-3-yl)pyridin-3-yl)pyrazolo[1,5-a]pyridine-3-carbonitrile

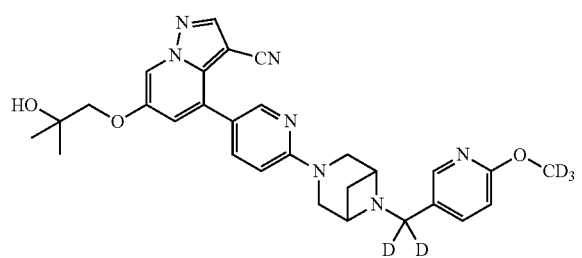 [SMILES: [2H]C([2H])([2H])Oc1ccc(C([2H])([2H])N2C3CC2CN(c2ccc(-c4cc(OCC(C)(C)O)cn5ncc(C#N)c45)cn2)C3)cn1]

The following route was used for the synthesis:

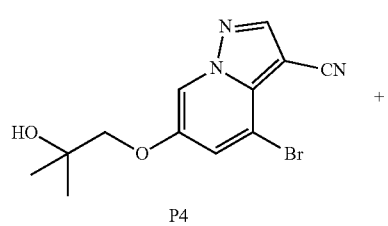

P4

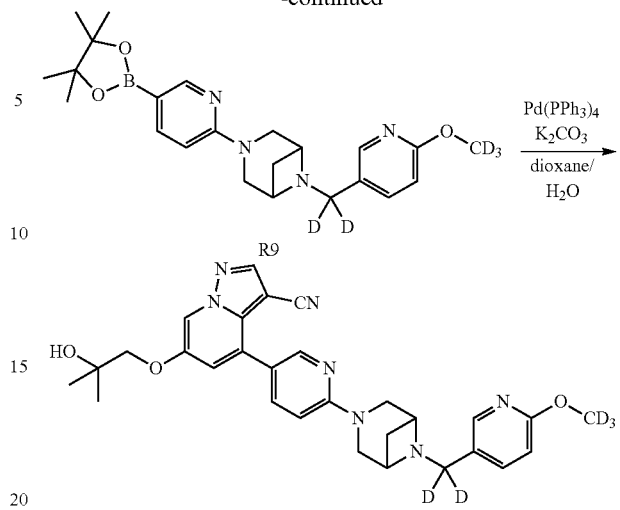

Under nitrogen protection, Pd(PPh₃)₄ (60 mg, 0.05 mmol) was added to intermediate R9 (236 mg, 0.55 mmol), intermediate P4 (150 mg, 0.48 mmol) and K₂CO₃ (166 mg, 1.2 mmol) in mixed solvent of dioxane (9 mL) and water (3 mL). Under nitrogen protection, the reaction was conducted at 85° C. overnight. The reaction was cooled to room temperature, filtered with diatomaceous earth, the filter cake was washed with DCM, the filtrate was concentrated under reduced pressure, and the concentrate was purified by column chromatography (DCM/MeOH=6%) to give 120 mg light yellow solid. Yield: 47.2%. purity: 96.12% (HPLC). LC-MS (APCI): m/z=531.2 (M+1)⁺. ¹H NMR (500 MHz, DMSO) δ 8.70 (s, 1H), 8.61 (s, 1H), 8.43 (s, 1H), 8.08 (s, 1H), 7.86 (d, J=8.5 Hz, 1H), 7.70 (d, J=7.9 Hz, 1H), 7.32 (s, 1H), 6.85-6.71 (m, 2H), 4.74 (s, 1H), 3.90 (s, 2H), 3.79-3.65 (m, 4H), 3.63-3.48 (m, 2H), 2.51-2.51 (m, 1H), 1.64-1.54 (m, J=8.3 Hz, 1H), 1.25 (s, 6H).

Biological Activity Assay.

(1) Metabolic Stability Evaluation

Microsome assay: human liver microsomes (HLM): 0.5 mg/mL, Xenotech; rat liver microsomes (RLM): 0.5 mg/mL, Xenotech; mice liver microsomes (MLM): 0.5 mg/mL, Xenotech; coenzyme (NADPH/NADH): 1 mM, Sigma Life Science; magnesium chloride: 5 mM, 100 mM phosphate buffer (pH is 7.4).

Preparation of stock solution: a certain amount of powder of the example compound and the reference compound were accurately weighed, and dissolved to 5 mM with DMSO, respectively.

Preparation of phosphate buffer (100 mM, pH7.4): Pre-formulated 150 mL 0.5 M potassium dihydrogen phosphate and 700 mL 0.5 M dipotassium hydrogen phosphate solution were mixed, then the pH of the mixture was adjusted to 7.4 with 0.5 M dipotassium hydrogen phosphate solution. Before use, 5-fold dilution was made with ultra-pure water, and magnesium chloride was added to afford phosphate buffer (100 mM), which containing 100 mM potassium phosphate, 3.3 mM magnesium chloride, pH is 7.4.

NADPH regeneration system solution (containing 6.5 mM NADP, 16.5 mM G-6-P, 3 U/mL G-6-P D, 3.3 mM magnesium chloride) was prepared and placed on wet ice before use.

Preparation of stop solution: Acetonitrile solution containing 50 ng/mL propranolol hydrochloride and 200 ng/mL tolbutamide (internal standard). 25057.5 μL phosphate buffer (pH 7.4) was taken into a 50 mL centrifuge tube, and 812.5 μL human liver microsome was added, mixed well to afford liver microsome diluent with a protein concentration of 0.625 mg/mL. 25057.5 μL phosphate buffer (pH 7.4) was taken into a 50 mL centrifuge tube, and 812.5 μL SD rat liver microsome was added, respectively, mixed well to afford liver microsome diluent with a protein concentration of 0.625 mg/mL. 25057.5 μL phosphate buffer (pH 7.4) was taken into a 50 mL centrifuge tube, and 812.5 μL mice liver microsome was added, respectively, mixed well to afford liver microsome diluent with a protein concentration of 0.625 mg/mL.

Incubation of the sample: The stock solutions of the corresponding compounds were diluted to 0.25 mM with an aqueous solution containing 70% acetonitrile as working solutions for use. 398 μL of human liver microsome or rat liver microsome or mice liver microsome diluent was taken and added to a 96-well incubation plate (N=2), respectively, and 2 μL of 0.25 mM working solution was then added respectively, and mixed well.

Determination of metabolic stability: 300 μL of pre-chilled stop solution was added to each well of a 96-well deep well plate and the plate was placed on ice as a stop plate. The 96-well incubation plate and NADPH regeneration system were placed in a 37° C. water bath box, shook at 100 rpm, and pre-incubated for 5 min. 80 μL of incubation solution was taken from each well of the incubation plate and added to the stop plate, mixed well, and 20 μL of NADPH regeneration system solution was supplemented, the resulted solution was considered as sample at 0 min. Then 80 μL of NADPH regeneration system solution was added to each well of the incubation plate to start the reaction and started timing. The reaction concentration of the corresponding compound is 1 μM, and the protein concentration is 0.5 mg/mL. 100 μL reaction solution was taken at 10, 30, 90 min of reaction, respectively, and added into stop plate, the reaction was stopped with 3 min vortex. The stop plate was centrifuged at 5000×g, 4° C. for 10 min. 100 μL of supernatant was taken to a 96-well plate where 100 μL of distilled water was added in advance, mixed well, sample analysis was subjected by LC-MS/MS.

Data analysis: LC-MS/MS system was used to detect peak area of corresponding compound and internal standard, peak area ratio of compound and internal standard was calculated. The slope was measured by plotting the natural logarithm of the remaining percentage of the compound against time, $t_{1/2}$ and $CL_{int}$ were calculated according to the following formula, wherein V/M equivalented to 1/protein concentration.

$$t_{1/2} = -\frac{0.693}{\text{Slope}}, \quad CL_{int} = \frac{0.693}{t_{1/2}} \cdot \frac{V}{M},$$

$t_{1/2}$(min); $CL_{int}$(μL/min/mg).

The compounds of the present disclosure were tested in the above in vitro stability assay, finding that the compounds of the present disclosure have excellent metabolic stability. The results of representative examples in the liver microsome experiments are summarized in Table 3 below.

TABLE 3

| Example No. | HLM | | RLM | | MLM | |
|---|---|---|---|---|---|---|
| | $t_{1/2}$ (min) | $CL_{int}$ (μL/min/mg) | $t_{1/2}$ (min) | $CL_{int}$ (μL/min/mg) | $t_{1/2}$ (min) | $CL_{int}$ (μL/min/mg) |
| 1 | 15.8 | 87.5 | 26.9 | 51.5 | 18.9 | 73.2 |
| 2 | 13.2 | 105.2 | 39.5 | 35.1 | 17.7 | 78.3 |
| 3 | 16.2 | 85.6 | 25.1 | 55.3 | 20.2 | 68.8 |
| 4 | 14.2 | 97.9 | 28.2 | 49.1 | 21.8 | 63.5 |
| 5 | 16.7 | 83.2 | 36.6 | 37.9 | 18.3 | 75.8 |
| 6 | 12.4 | 112.1 | 29.3 | 47.3 | 21.3 | 65.0 |
| 7 | 124.4 | 11.1 | 122.3 | 11.3 | 18.2 | 76.0 |
| 8 | 131.1 | 10.6 | 262.8 | 5.3 | 237.4 | 5.8 |
| 9 | 98.9 | 14.0 | 233.9 | 5.9 | 182.6 | 7.6 |
| 10 | 194.1 | 7.1 | 666.9 | 2.1 | 259.8 | 5.3 |
| 11 | 14.4 | 96.2 | 118.4 | 11.7 | 30.9 | 44.8 |
| 12 | 14.9 | 93.1 | 137.2 | 10.1 | 30.8 | 44.9 |
| 13 | 15.0 | 92.2 | 128.3 | 10.8 | 32.4 | 42.8 |

(2) Pharmacokinetic Experiment in Rats 6 male Sprague-Dawley rats (7-8 weeks old, and weighing approximately 210 g) were divided into 2 groups with 3 rats in each group. The rats were intravenously or orally administered a single dose of compounds (10 mg/kg orally) to compare pharmacokinetic differences.

The rats were fed on standard food and water. Fasting was started 16 hours before the test. The drug was dissolved in PEG400 and dimethyl sulfoxide. The blood samples were collected from eyelids at the time points of 0.083 hour, 0.25 hour, 0.5 hour, 1 hour, 2 hours, 4 hours, 6 hours, 8 hours, 12 hours, and 24 hours after administration.

Rats were briefly anesthetized after inhalation of diethyl ether and 300 μL of blood sample was collected from the eyelids into test tubes. There was 30 μL of 1% heparin salt solution in the test tube. Tubes were dried at 60° C. overnight before use. After the blood sample was collected at the last time point, the rats were sacrificed after ether anesthesia.

Immediately after the collection of the blood sample, the test tube was gently inverted at least 5 times to ensure sufficient mixing and then placed on ice. The blood sample was centrifuged at 5000 rpm at 4° C. for 5 minutes to separate the plasma from the red blood cells. 100 μL of plasma was aspirated into a clean plastic centrifuge tube with a pipette, marking with the name of the compound and time point. Plasma was stored at −80° C. prior to analysis. The concentration of the compound of the present disclosure in plasma was determined by LC-MS/MS. The pharmacokinetic parameters were calculated based on the blood concentration of the drug for each animal at different time points.

Experiments showed that the compounds of the present disclosure have better pharmacokinetic properties in vivo, and therefore have better pharmacodynamics and treatment effects.

(3) Kinase Inhibitory Effect

Reagents and materials: Ret wt (Carna, catalog No. 08-159-10 ug), RET (V804M), Active (Signalchem, catalog No. R02-12GG), HTRF KinEASE-TK kit (Cisbio, catalog No. 62TK0PEC), CEP-32496 (MCE, catalog No. HY-15200), ATP (Sigma, catalog No. A7699), DMSO (Sigma, catalog No. D8418-1L), DTT (Sigma, catalog No. D0632), MgCl$_2$ (Sigma, catalog No. M1028), 384-well plate (Labcyte, catalog No. P-05525-BC).

Specific Experimental Methods:

Compound formulation: The test compounds were dissolved in DMSO to prepare a 10 mM stock solution. Then, the stock solution was diluted 10 times with a 3-fold gradient. When dosing, 10-fold dilutions thereof were made with buffer solution.

Ret wt and RET V804M kinase assay: In 5× kinase buffer solution A, Ret wt or RET V804M kinase was mixed with pre-formulated and diluted compounds of different concentrations for 10 minutes in duplicate for each concentration. The corresponding substrate and ATP were added thereto, and reacted at room temperature for 20 minutes (both a negative and a positive control were set: the negative control is blank, the positive control is CEP-32496). Detection reagent (reagent in HTRF KinEASE-TK kit) was added after the reaction is complete, after 30 minutes of incubation at room temperature, Envision ELISA reader was used for detection of enzyme activities in the presence of compounds of the present disclosure with different concentrations, and the inhibitory activities of different concentrations of compounds on enzyme activity were calculated, Graphpad 5.0 software was used to fit the inhibitory activities on enzyme activity against different concentrations of compounds, and $IC_{50}$ values were calculated.

Compounds of the present disclosure were tested in the above kinase inhibition assay, finding that the compounds of the present disclosure have potent activity on Ret wt and RET V804M. Results of representative example compounds were summarized in Table 4 below.

TABLE 4

| Example No. | Ret wt IC50 (nM) | RET V804M IC50 (nM) |
|---|---|---|
| 1 | 0.06 | 0.17 |
| 2 | 0.16 | 0.16 |
| 3 | 0.17 | 0.29 |
| 4 | 0.12 | 0.33 |
| 5 | 0.11 | 0.23 |
| 6 | 0.07 | 0.36 |
| 7 | 0.18 | 0.21 |
| 8 | 0.36 | 7.32 |
| 9 | 0.37 | 4.30 |
| 10 | 0.23 | 4.91 |
| 11 | 0.15 | 3.20 |
| 12 | 0.17 | 3.25 |
| 13 | 0.06 | 0.27 |

(4) Cytotoxicity Assay

Inhibitory effects of example compounds on cell viabilities of $Ba/F_3$ parental, $Ba/F_3$ KIF5B-RET, $Ba/F_3$ KIF5B-RET$^{V804M}$ were tested.

Reagents and materials: Fetal bovine serum FBS (GIBCO, catalog No. 10099141), CellTiter-Glo® Luminescent Cell Viability Assay (Promega, Cat #G7572), 96-well transparent flat-bottomed black wall plate (Corning®, Cat #3603).

Experimental Methods:
Cell Culture and Inoculation:
1. The cells in the logarithmic growth phase were harvested and counted using platelet counter. The trypan blue exclusion method was used to detect the cell viability to ensure that the cell viability is above 90%;
2. The cell concentration was adjusted to 3000 cells/well; 90 μL of cell suspension was separately added to a 96-well plate;
3. Cells in the 96-well plate were placed at conditions of 37° C., 5% $CO_2$, 95% humidity overnight.

Drug Dilution and Dosing:
1. 10-fold drug solutions were formulated, with the highest concentration of 10 which was diluted into 9 concentrations with a 3.16 fold dilution, and 10 μL drug solutions were added to each well of 96-well plate seeded with cells in triplicate for each concentration;
2. After addition of drug, the cells in 96-well plate were placed under conditions of 37° C., 5% $CO_2$, 95% humidity, and incubated for 72 hours, followed by the CTG analysis.

Reading at End Point:
1. the CTG reagent was thawn and the cell plate was equilibrated to room temperature for 30 minutes;
2. an equal volume (10 μL) of the CTG solutions were added to each well;
3. the plate was vibrated on an orbital shaker for 5 minutes to lyse the cells;
4. the cell plate was placed at room temperature for 20 minutes to stabilize the luminescence signal;
5. the luminescence value was read.

Data Processing

GraphPad Prism 5.0 software was used to analyze data, nonlinear S-curve regression was used to fit the data to obtain a dose-response curve, and the $IC_{50}$ values were calculated therefrom.

Cell viability (%)=(Lum of drug to be tested–Lum of culture medium control)/(Lum of cell control–Lum of culture medium control)×100%.

The compounds of the present disclosure were tested in the above cytotoxic assay, finding that the compounds of the present disclosure have potent activity against cell lines $Ba/F_3$ KIF5B-RET and $Ba/F_3$ KIF5B-RET$^{V804M}$ and excellent selectivity over $Ba/F_3$ parental. The results of inhibitory effect of the compounds of the representative examples on the in vitro proliferation of cancer cells are summarized in Table 5 below.

TABLE 5

| | $IC_{50}$ (nM) | | |
|---|---|---|---|
| Example No. | $Ba/F_3$ parental | $Ba/F_3$ KIF5B-RET | $Ba/F_3$ KIF5B-RET$^{V804M}$ |
| 1 | 288.22 | 1.66 | 6.14 |
| 2 | 295.97 | 3.22 | 6.54 |
| 3 | 260.19 | 3.34 | 7.03 |
| 4 | 260.68 | 1.88 | 6.37 |
| 5 | 261.14 | 2.92 | 8.45 |
| 6 | 252.13 | 1.81 | 6.59 |
| 7 | 663.84 | 3.54 | 11.34 |
| 8 | 3360.90 | 69.56 | 387.98 |
| 9 | 2350.49 | 52.19 | 189.84 |
| 10 | 2308.28 | 43.85 | 218.95 |
| 11 | 3511.55 | 19.08 | 40.46 |
| 12 | 5934.87 | 16.04 | 45.24 |
| 13 | >10000 | 23.53 | 90.05 |

The above is detailed description of the present disclosure in conjunction with specific embodiments, and it cannot be assumed that the specific implementation of the present disclosure is limited to these descriptions. For ordinary person skilled in the technical field to which the present disclosure pertains, without deviating from the concept of the present disclosure, various simple deductions or substitutions may be made, which should be regarded as falling within the protection scope of the present disclosure.

What is claimed is:

1. A compound of formula (I), or a tautomer, stereoisomer, crystal form, pharmaceutically acceptable salt, hydrate or solvate thereof:

formula (I)

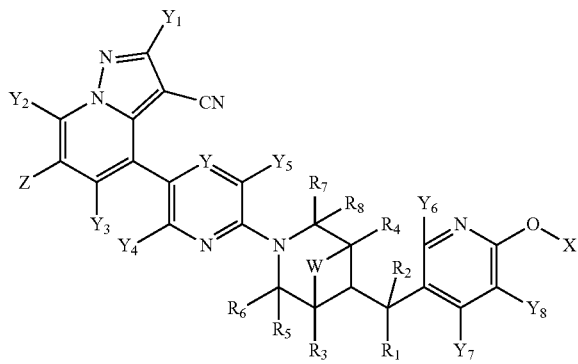

wherein,
Y is selected from the group consisting of CH and N, which is optionally substituted by deuterium, halogen or trifluoromethyl;
W is $CR_9R_{10}$;
$R_1$, $R_2$, $R_3$, $R_4$, $R_5$, $R_6$, $R_7$, $R_8$, $R_9$ and $R_{10}$ are each independently selected from the group consisting of hydrogen and deuterium;
$Y_1$, $Y_2$, $Y_3$, $Y_4$, $Y_5$, $Y_6$, $Y_7$ and $Y_8$ are each independently selected from the group consisting of hydrogen, deuterium, halogen and trifluoromethyl;
X is selected from the group consisting of $CH_3$, $CD_3$, $CHD_2$ and $CH_2D$;
Z is selected from the group consisting of:

(a)

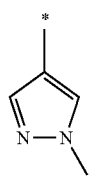

(b)

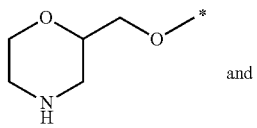

and (c)

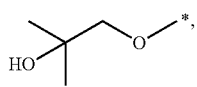

which is optionally substituted by 1, 2, 3, 4, 5, 6, 7, 8 or 9 deuterium;

*represents the bond connected to the core;

provided that the above compound has at least one deuterium atom.

2. The compound according to claim 1, which is the compound of formula (II-A):

formula (II-A)

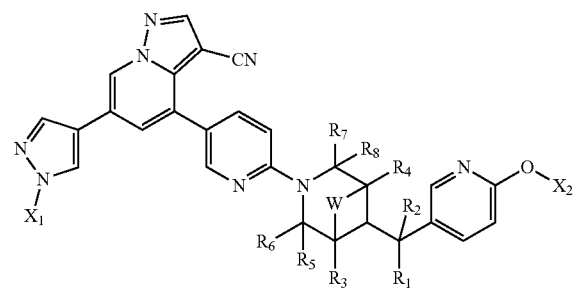

wherein,
W is $CR_9R_{10}$;
$R_1$, $R_2$, $R_3$, $R_4$, $R_5$, $R_6$, $R_7$, $R_8$, $R_9$ and $R_{10}$ are each independently selected from the group consisting of hydrogen and deuterium;
$X_1$ and $X_2$ are each independently selected from the group consisting of $CH_3$, $CD_3$, $CHD_2$ and $CH_2D$;
provided that the above compound has at least one deuterium atom;
or a tautomer, stereoisomer, crystal form, pharmaceutically acceptable salt, hydrate or solvate thereof.

3. The compound according to claim 1, which is the compound of formula (II-B):

formula (II-B)

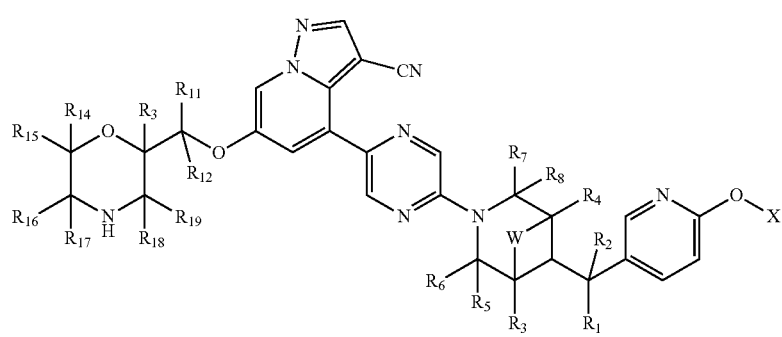

wherein,

W is $CR_9R_{10}$;

$R_1, R_2, R_3, R_4, R_5, R_6, R_7, R_8, R_9, R_{10}, R_{11}, R_{12}, R_{13}, R_{14}, R_{15}, R_{16}, R_{17}, R_{18}$ and $R_{19}$ are each independently selected from the group consisting of hydrogen and deuterium;

X is selected from the group consisting of $CH_3$, $CD_3$, $CHD_2$ and $CH_2D$;

provided that the above compound has at least one deuterium atom;

or a tautomer, stereoisomer, crystal form, pharmaceutically acceptable salt, hydrate or solvate thereof.

4. The compound according to claim 3, which is the compound of formula (II-B-a):

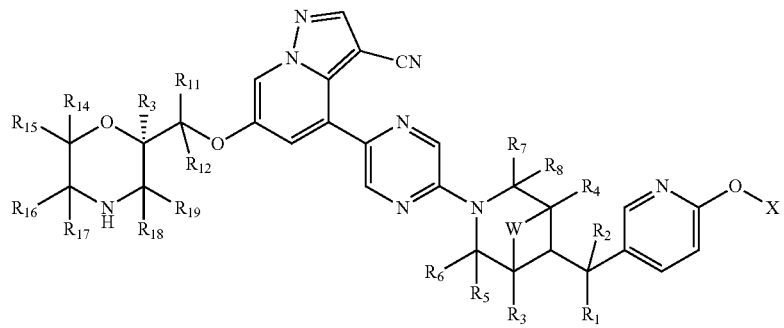

formula (II-B-a)

wherein,

W is $CR_9R_{10}$;

$R_1, R_2, R_3, R_4, R_5, R_6, R_7, R_8, R_9, R_{10}, R_{11}, R_{12}, R_{13}, R_{14}, R_{15}, R_{16}, R_{17}, R_{18}$ and $R_{19}$ are each independently selected from the group consisting of hydrogen and deuterium;

X is selected from the group consisting of $CH_3$, $CD_3$, $CHD_2$ and $CH_2D$;

provided that the above compound has at least one deuterium atom;

or a tautomer, stereoisomer, crystal form, pharmaceutically acceptable salt, hydrate or solvate thereof.

5. The compound according to claim 1, which is the compound of formula (II-C):

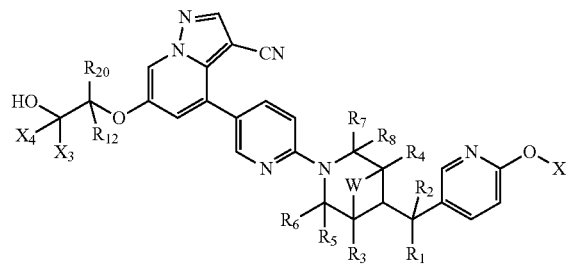

formula (II-C)

wherein,

W is $CR_9R_{10}$;

$R_1, R_2, R_3, R_4, R_5, R_6, R_7, R_8, R_9, R_{10}, R_{20}$ and $R_{21}$ are each independently selected from the group consisting of hydrogen and deuterium;

X, $X_3$ and $X_4$ are each independently selected from the group consisting of $CH_3$, $CD_3$, $CHD_2$ and $CH_2D$;

provided that the above compound has at least one deuterium atom;

or a tautomer, stereoisomer, crystal form, pharmaceutically acceptable salt, hydrate or solvate thereof.

6. The compound according to claim 1, which is selected from the following compounds:

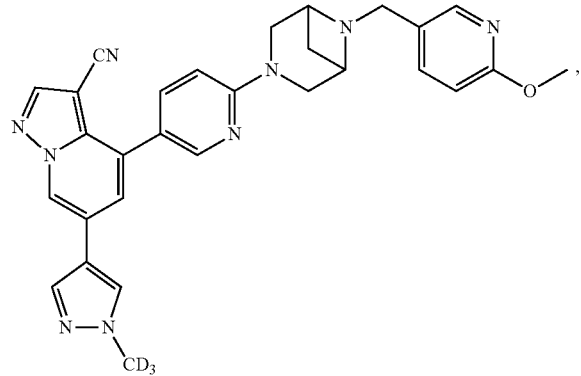

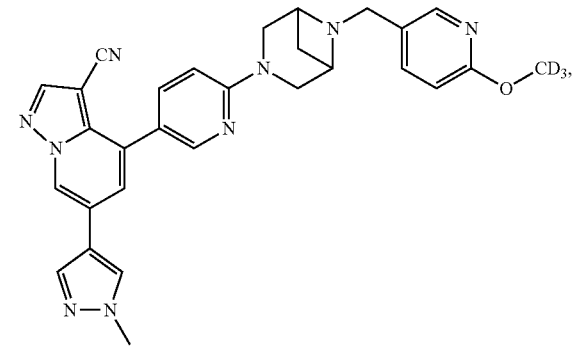

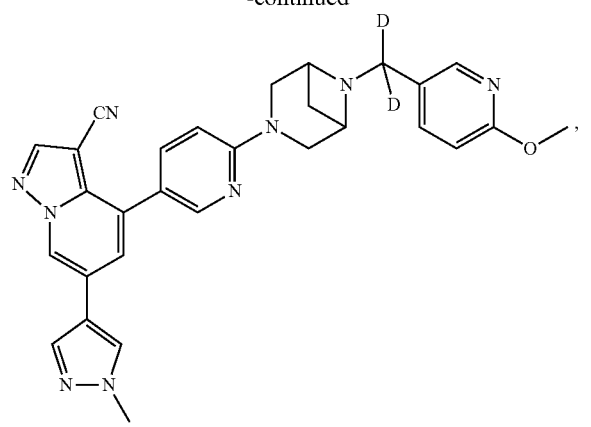
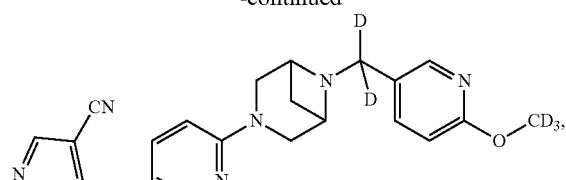
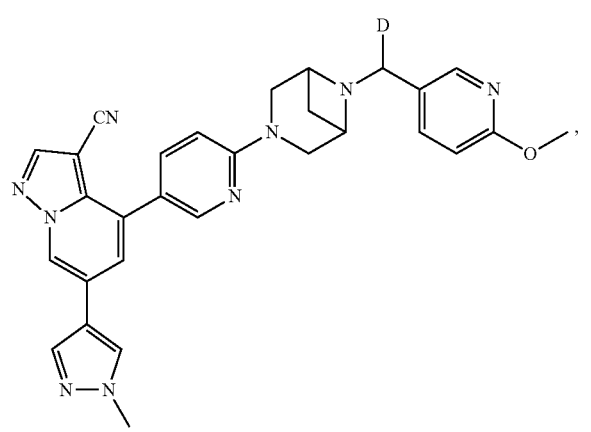
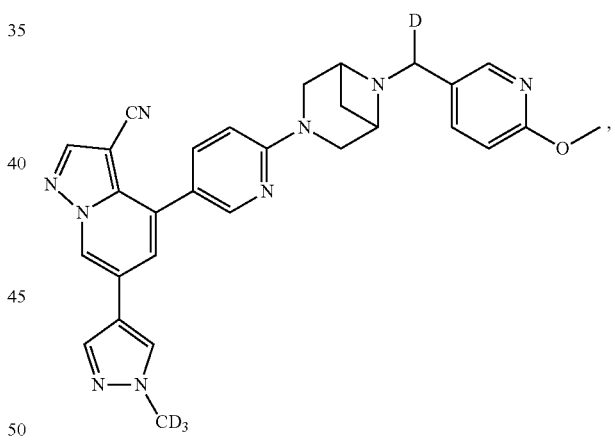
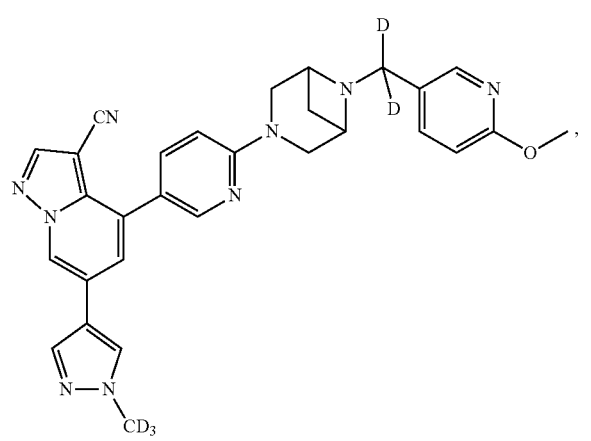
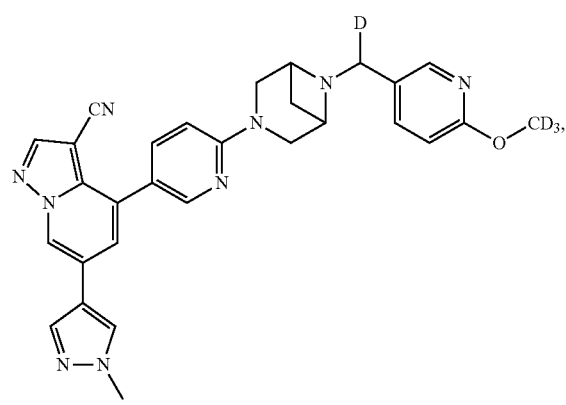

115
-continued
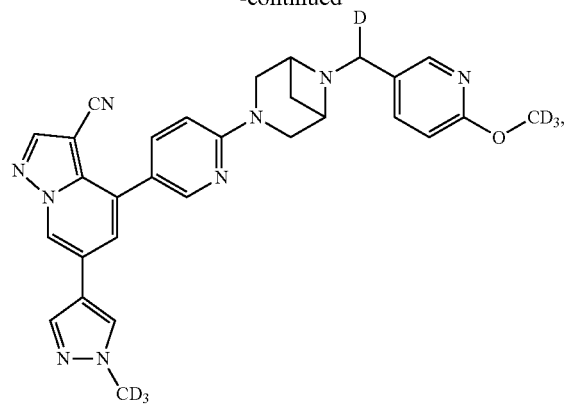
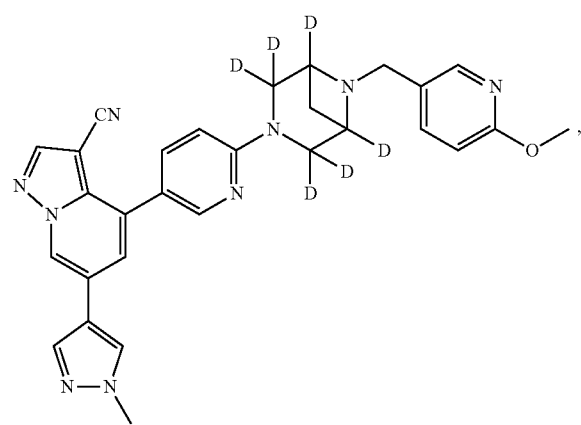
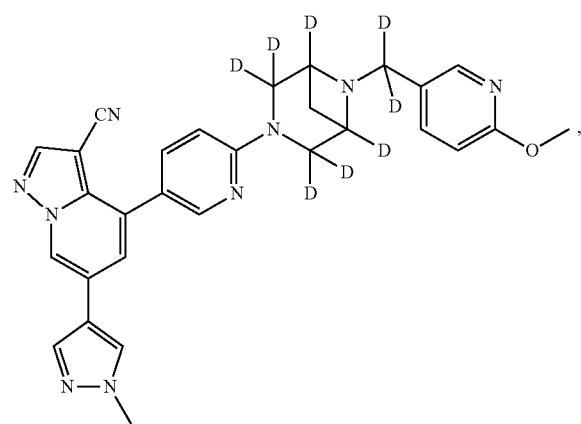
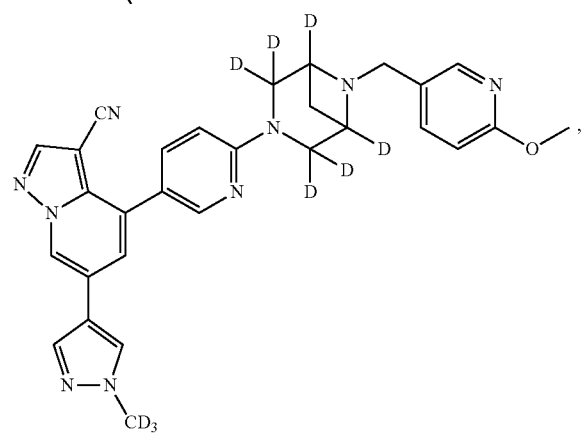
116
-continued
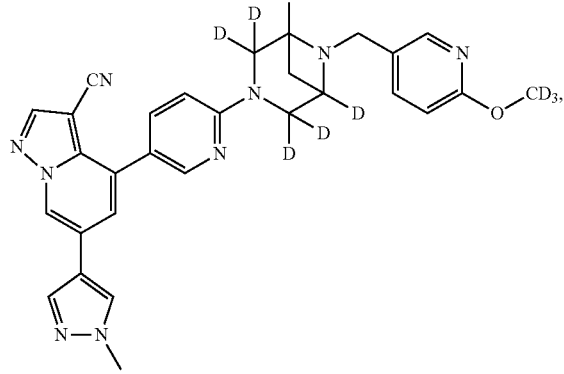
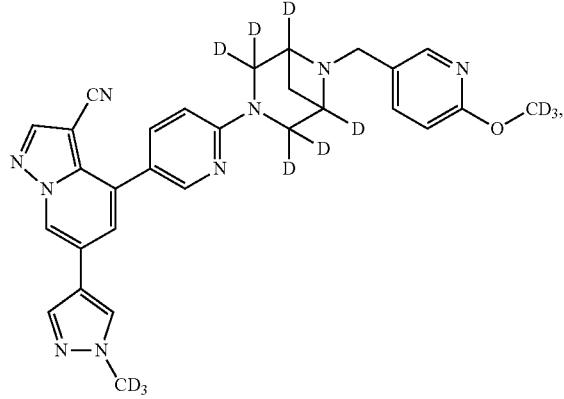
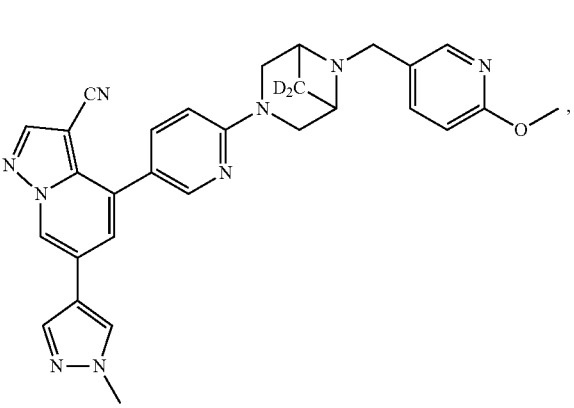
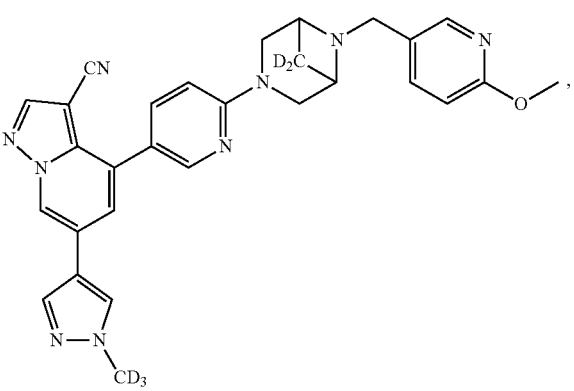

117
-continued
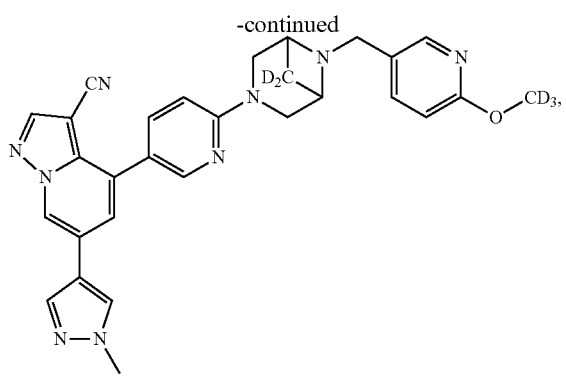
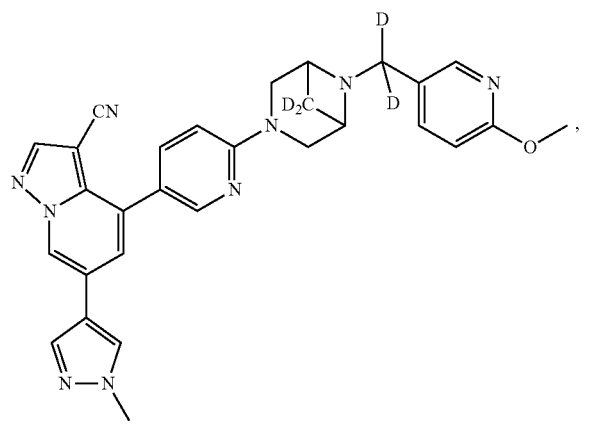
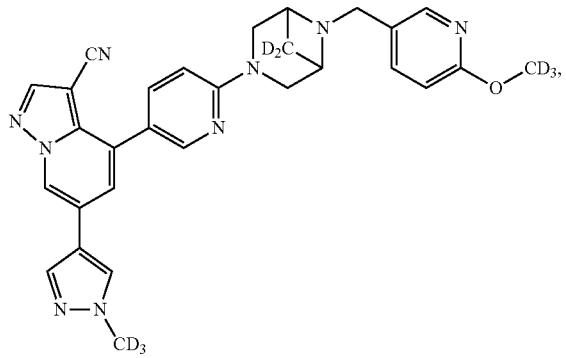
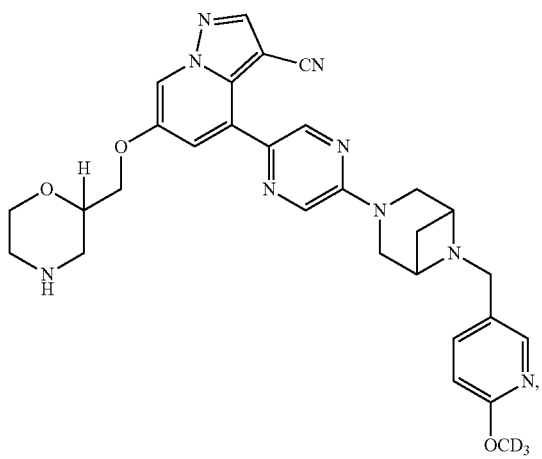
118
-continued
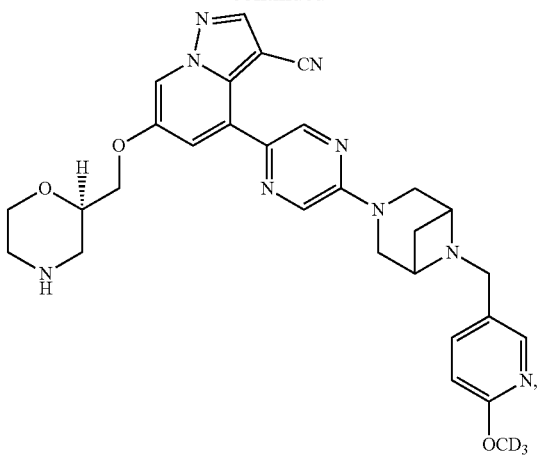
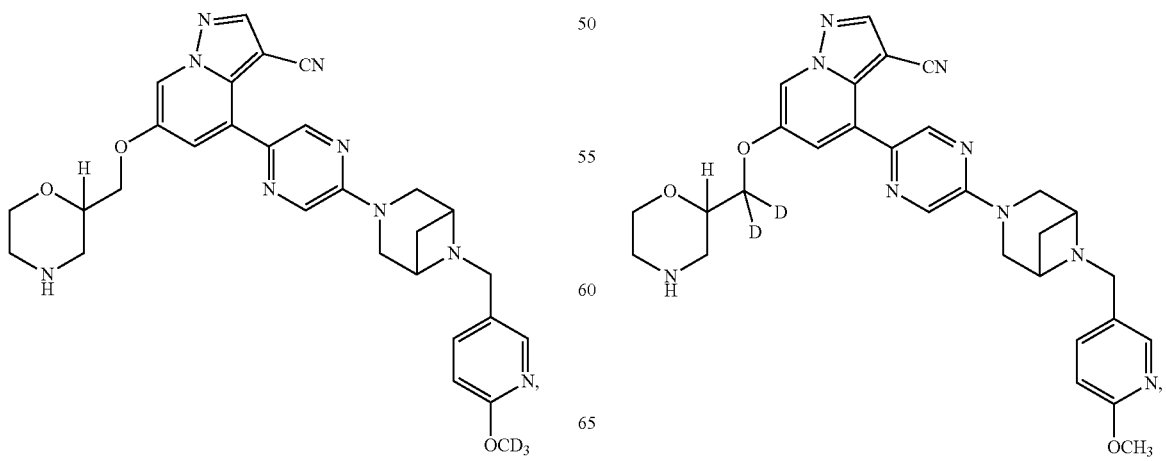

119
-continued
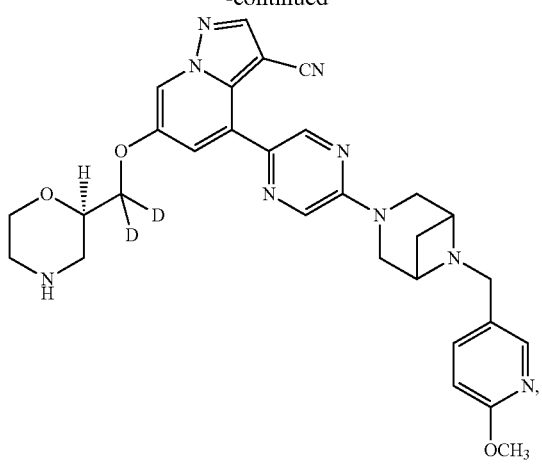
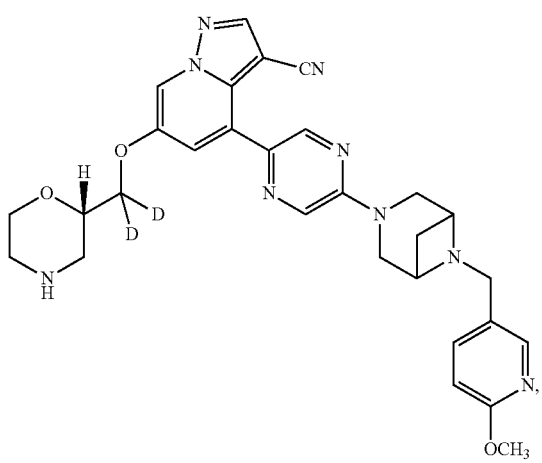
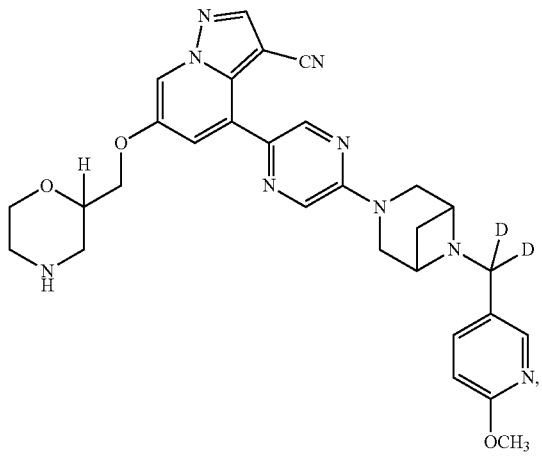
120
-continued
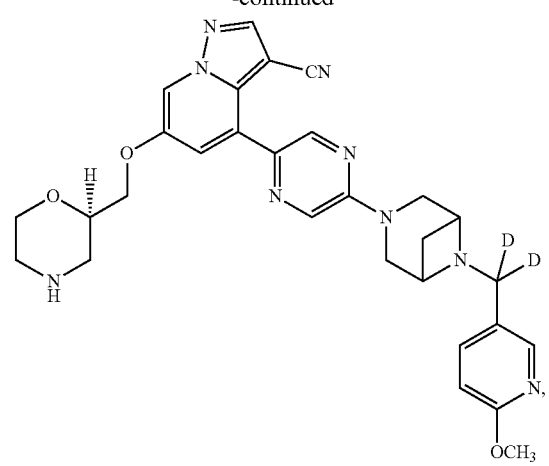
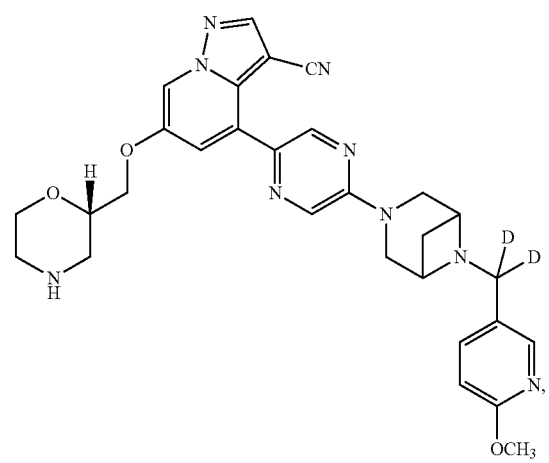
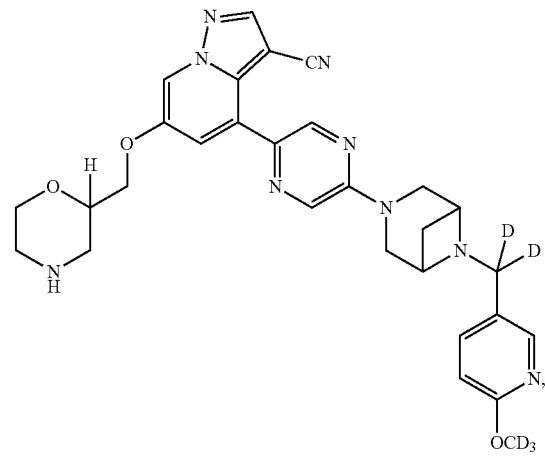

121
-continued
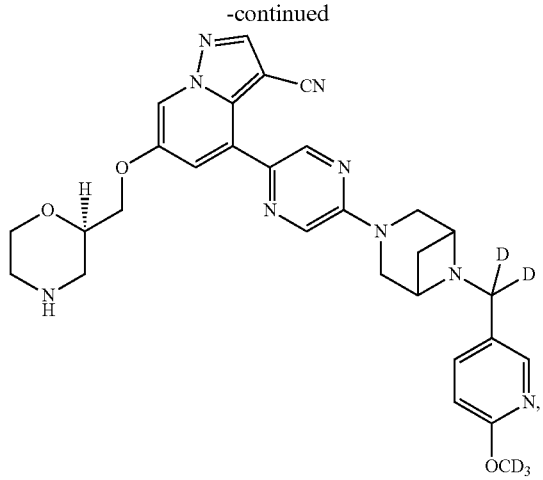
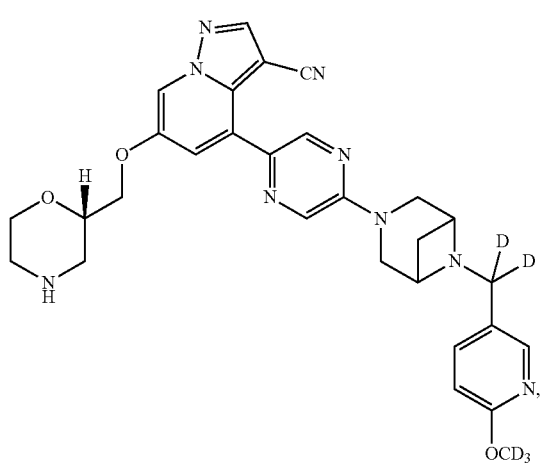
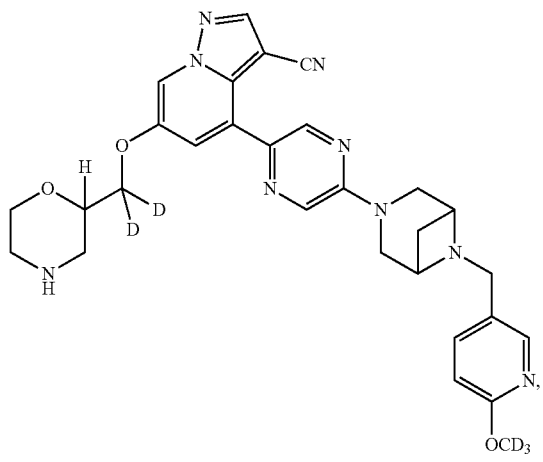
122
-continued
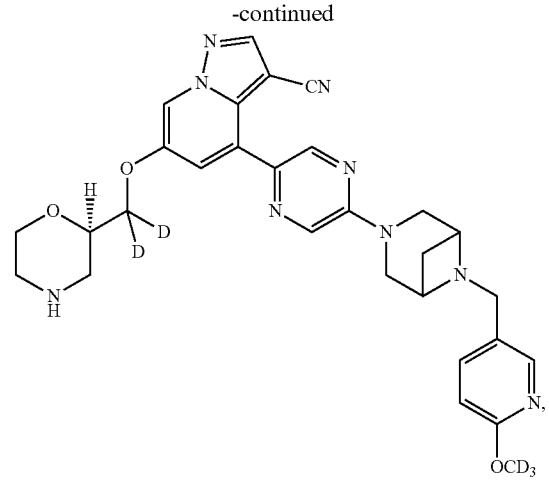
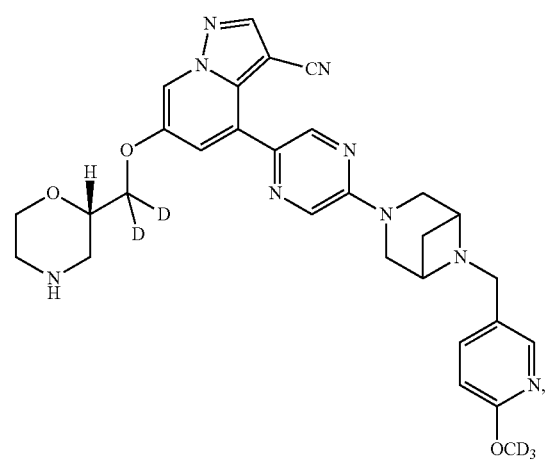
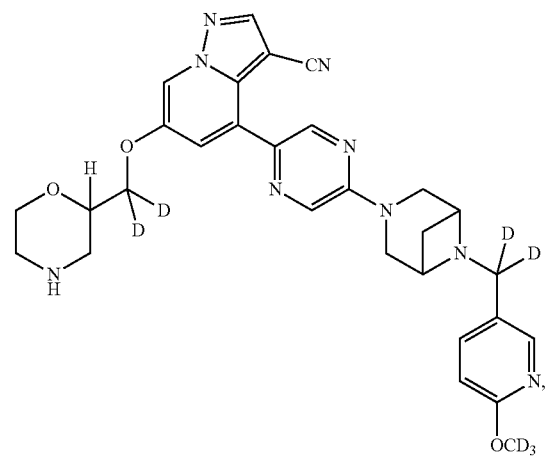

123
-continued
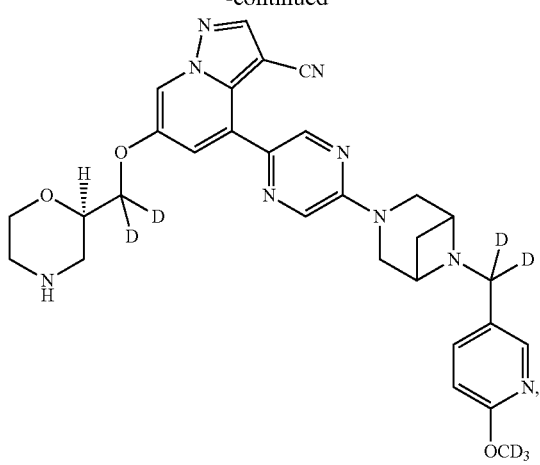
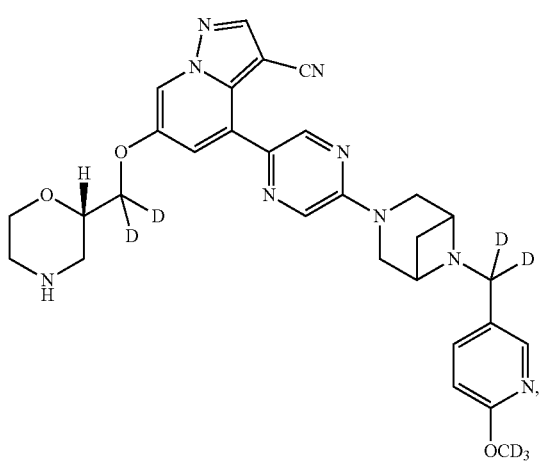
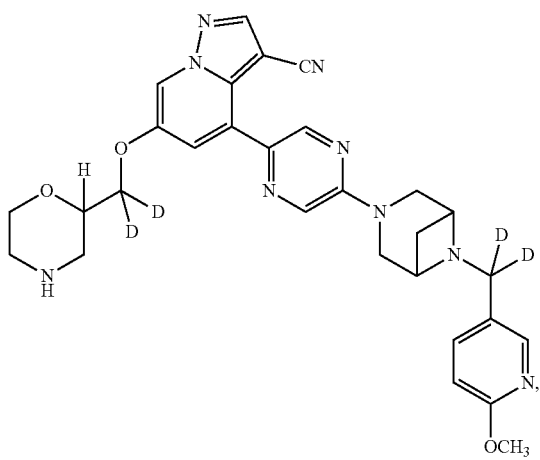
124
-continued
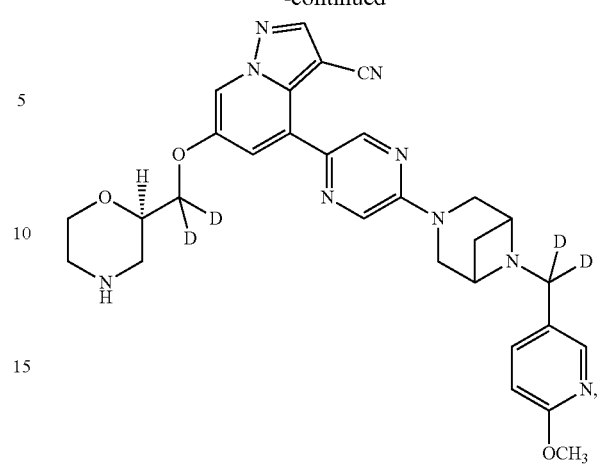
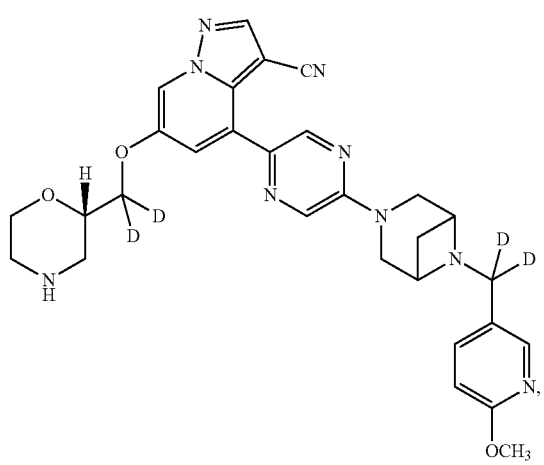

125
-continued
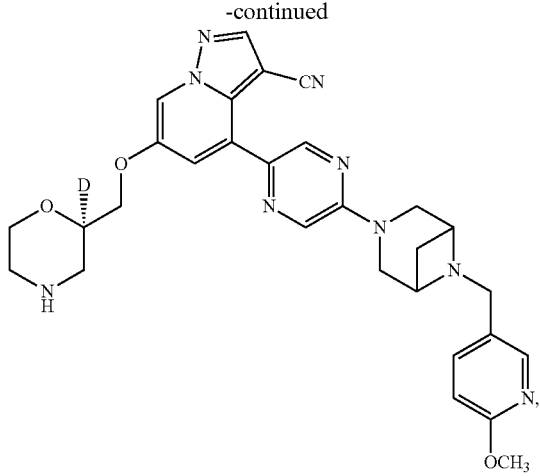
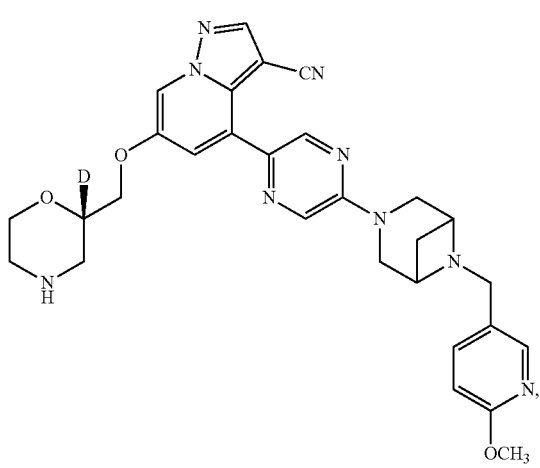
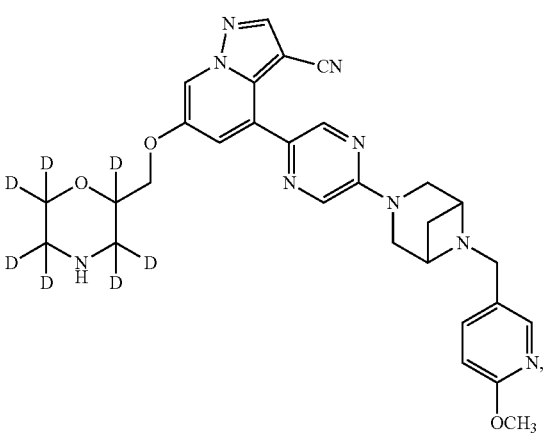
126
-continued
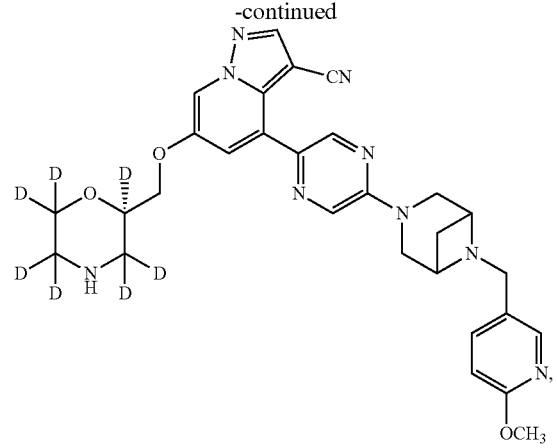
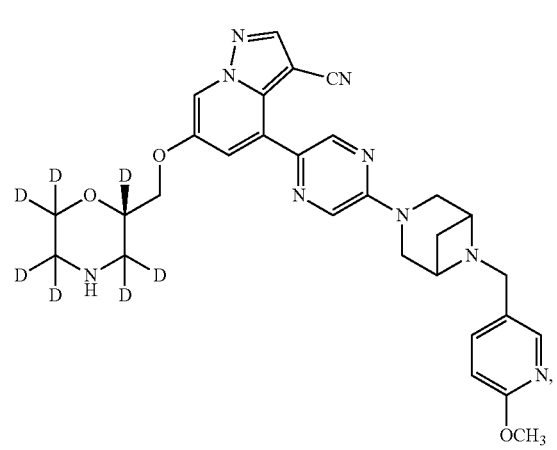
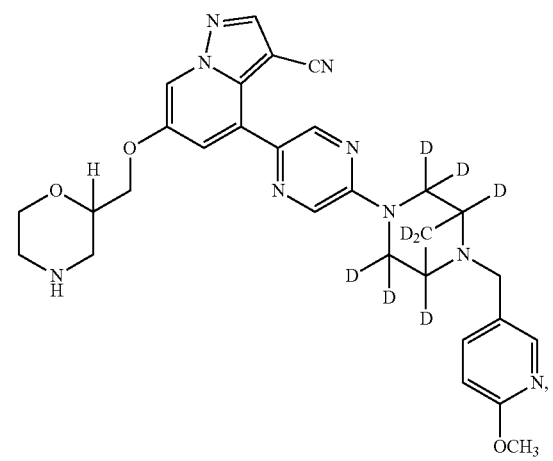

127
-continued
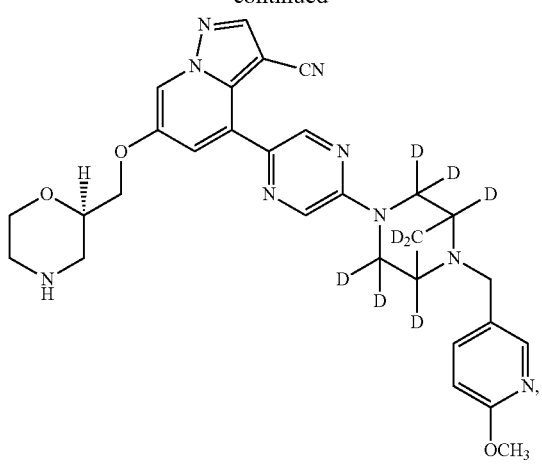
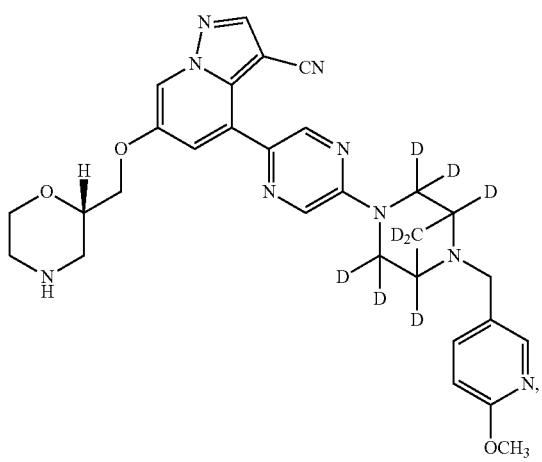
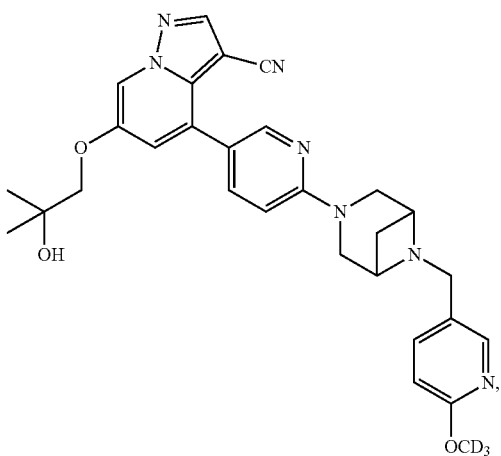
128
-continued
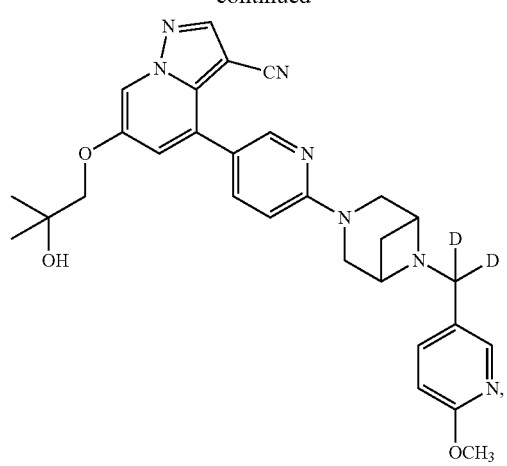
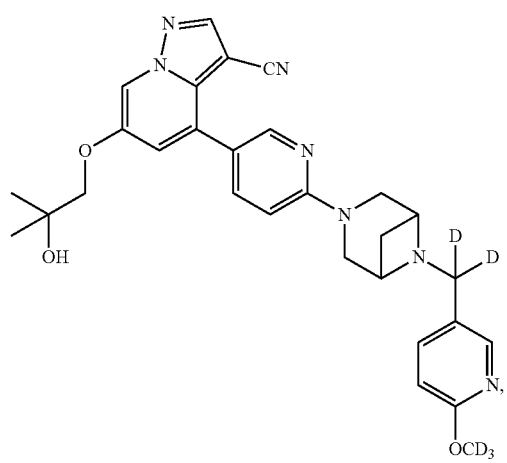
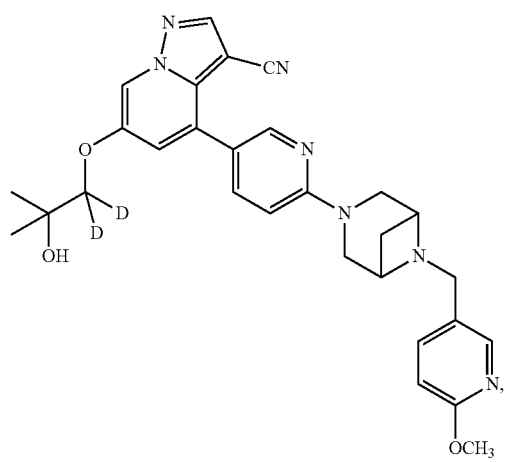

129
-continued
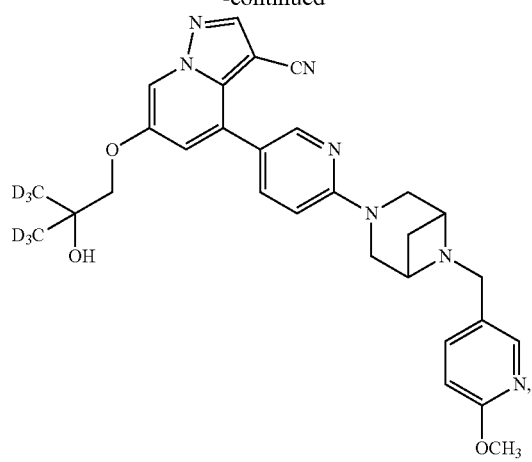
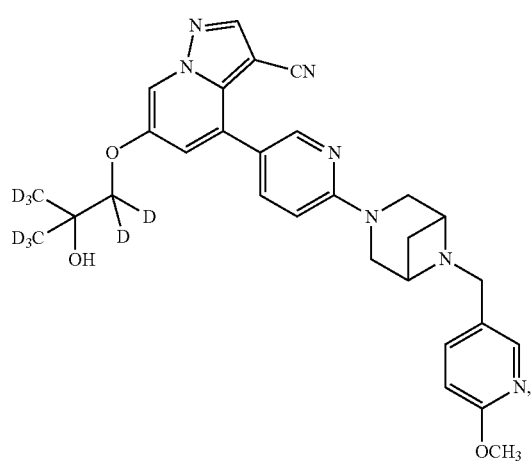
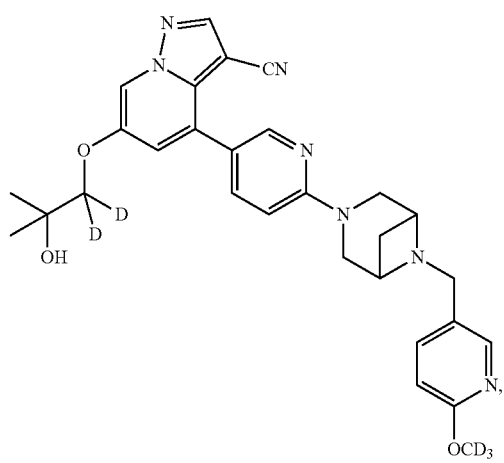
130
-continued
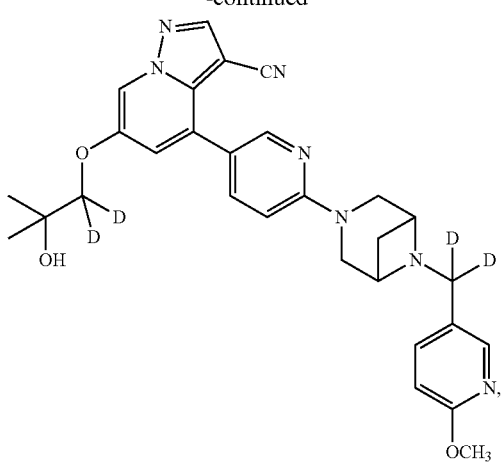
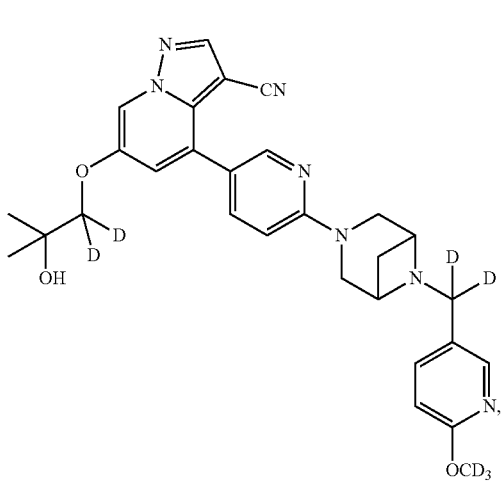
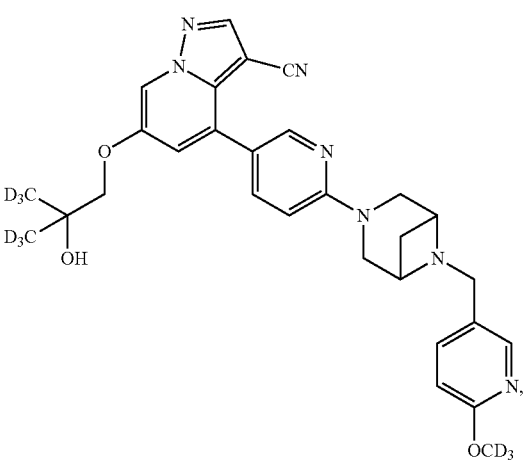

-continued
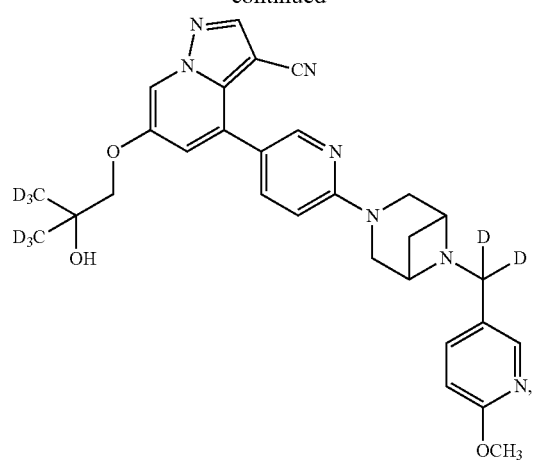
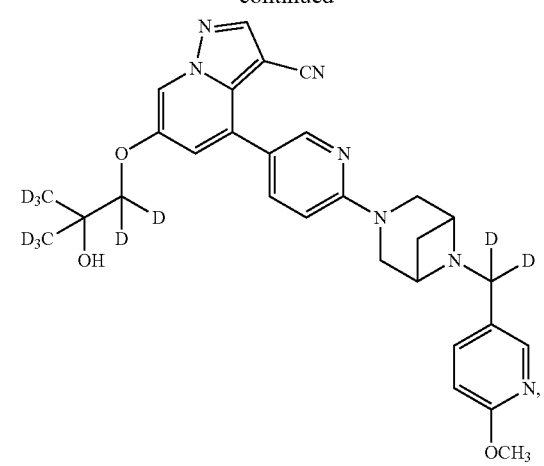
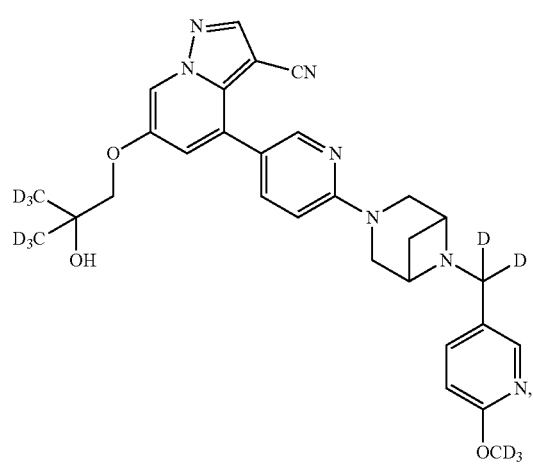
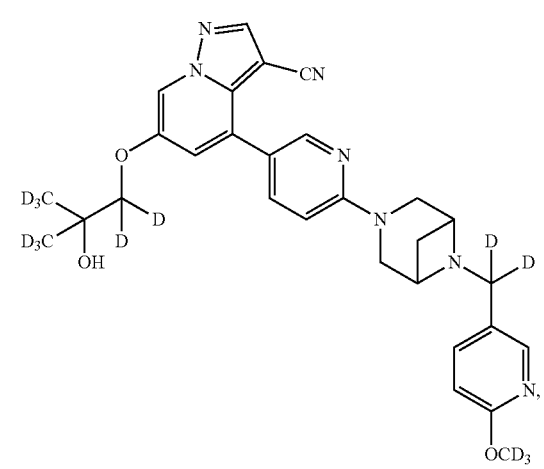
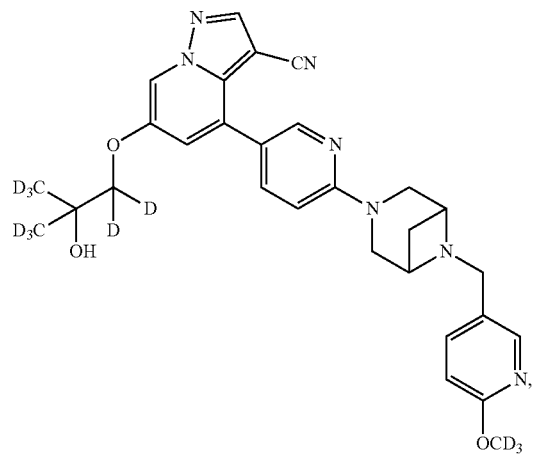
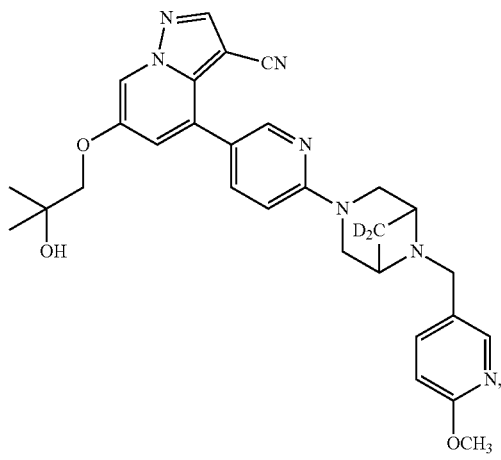

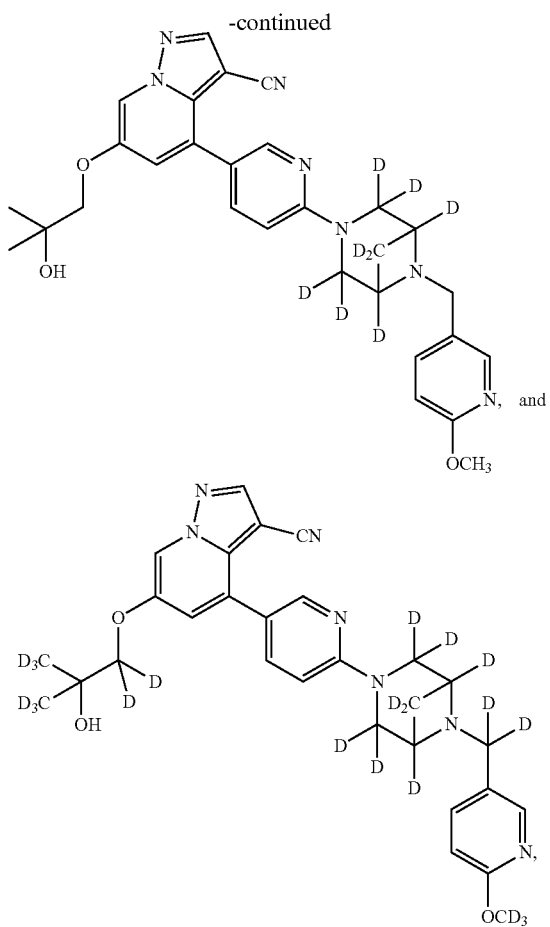

or a tautomer, stereoisomer, crystal form, pharmaceutically acceptable salt, hydrate or solvate thereof.

7. A pharmaceutical composition, comprising pharmaceutically acceptable excipient(s) and a compound according to claim 1, or a tautomer, stereoisomer, crystal form, pharmaceutically acceptable salt, hydrate or solvate thereof.

8. A method of treating a RET-associated cancer in a subject, comprising administering to the subject the compound according to claim 1 or a tautomer, stereoisomer, crystal form, pharmaceutically acceptable salt, hydrate or solvate thereof.

9. The method according to claim 8, wherein the RET-associated cancers are cancers in which a RET gene, a RET kinase protein, or the expression or activity or level of any of the same is dysregulated.

10. The method according to claim 8, wherein the RET-associated cancer is selected from the group consisting of lung cancer, papillary thyroid cancer, medullary thyroid cancer, differentiated thyroid cancer, recurrent thyroid cancer, refractory differentiated thyroid cancer, multiple endocrine tumors of type 2A or 2B (MEN2A or MEN2B, respectively), pheochromocytoma, parathyroid hyperplasia, breast cancer, pancreatic cancer, colorectal cancer, papillary renal cell carcinoma, gastrointestinal mucosal gangliocytoma and cervical cancer.

11. The compound according to claim 2, wherein, $X_1$ is $CD_3$.

12. The compound according to claim 2, wherein, $X_2$ is $CD_3$.

13. The compound according to claim 2, wherein, $R_1$ and $R_2$ are deuterium.

14. The compound according to claim 3, wherein, X is $CD_3$.

15. The compound according to claim 3, wherein, $R_1$ and $R_2$ are deuterium.

16. The compound according to claim 4, wherein, X is $CD_3$.

17. The compound according to claim 4, wherein, $R_1$ and $R_2$ are deuterium.

18. The compound according to claim 5, wherein, X is $CD_3$.

19. The compound according to claim 5, wherein, $R_1$ and $R_2$ are deuterium.

20. The method according to claim 10, wherein the cancer is selected from the group consisting of RET fusion lung cancer, RET fusion papillary thyroid cancer or medullary thyroid cancer; wherein the lung cancer is small cell lung cancer, non-small cell lung cancer, bronchiolocarcinoma and lung adenocarcinoma.

* * * * *